(12) United States Patent
Guan et al.

(10) Patent No.: US 12,077,591 B2
(45) Date of Patent: Sep. 3, 2024

(54) TrkA ANTIBODY AND APPLICATION THEREOF

(71) Applicant: 4B TECHNOLOGIES (SUZHOU) LIMITED, Jiangsu (CN)

(72) Inventors: Xiaoming Guan, Jiangsu (CN); Chen Lv, Jiangsu (CN); Bai Lu, Jiangsu (CN); Gang Lu, Jiangsu (CN); Jun Zhou, Jiangsu (CN); Dong Yang, Jiangsu (CN); Jie Xie, Jiangsu (CN); Jing Su, Jiangsu (CN)

(73) Assignee: 4B TECHNOLOGIES (SUZHOU) LIMITED, Suzhou (CN)

( * ) Notice: Subject to any disclaimer, the term of this patent is extended or adjusted under 35 U.S.C. 154(b) by 0 days.

(21) Appl. No.: 18/323,438

(22) Filed: May 25, 2023

(65) Prior Publication Data
US 2024/0002516 A1 Jan. 4, 2024

Related U.S. Application Data

(63) Continuation of application No. PCT/CN2022/142180, filed on Dec. 27, 2022.

(30) Foreign Application Priority Data

Dec. 28, 2021 (WO) ............... PCT/CN2021/142017

(51) Int. Cl.
*C07K 16/28* (2006.01)
*A61K 39/00* (2006.01)
*A61P 25/04* (2006.01)

(52) U.S. Cl.
CPC .......... *C07K 16/2863* (2013.01); *A61P 25/04* (2018.01); *A61K 2039/505* (2013.01); *C07K 2317/24* (2013.01); *C07K 2317/34* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | WO 2004/032870 | 4/2004 |
| WO | WO 2006/131952 | 12/2006 |
| WO | WO 2009/098238 | 8/2009 |
| WO | WO 2016/087677 | 6/2016 |
| WO | WO 2019/068730 | 4/2019 |

OTHER PUBLICATIONS

International Search Report issued Mar. 3, 2023, is International Application No. PCT/CN2022/142180.
He, L.Z. et al., "Role of NGF/TrKA Signal Axis in Osteoarthritis", *Orthopedic Journal of China*, Jun. 5, 2020, pp. 933-936.

*Primary Examiner* — Ruixiang Li
(74) *Attorney, Agent, or Firm* — Merchant & Gould P.C.

(57) ABSTRACT

The present disclosure provides TrkA antibodies, compositions comprising such antibodies, and methods of using such antibodies for the prevention and/or treatment of a disease or disorder associated with an inappropriate expression or function of TrkA, such as pain.

14 Claims, 33 Drawing Sheets
Specification includes a Sequence Listing.

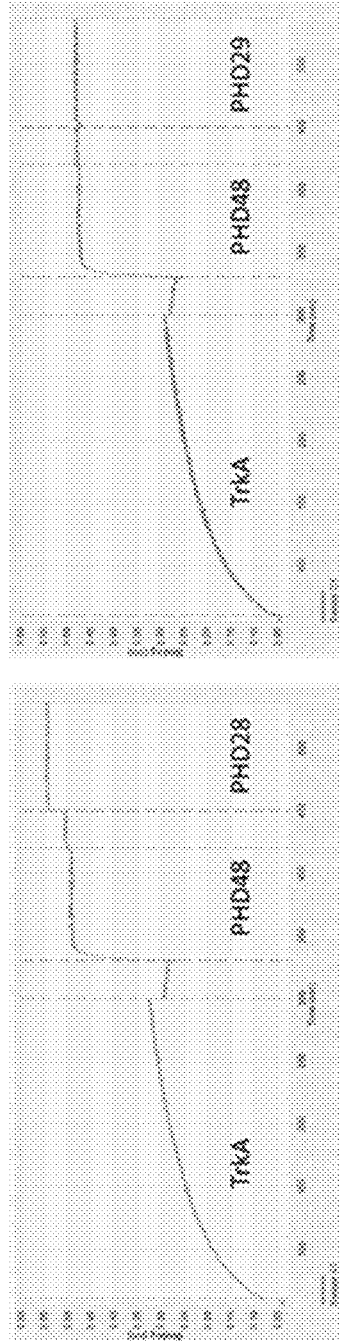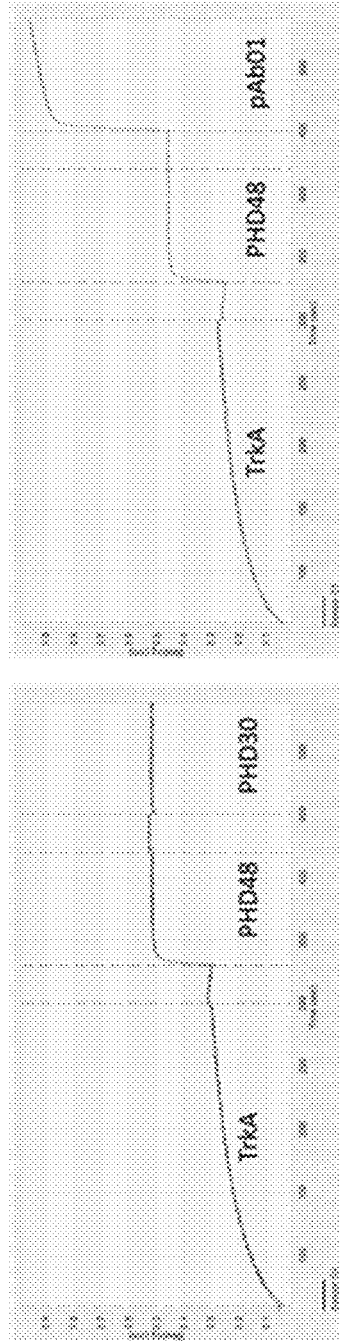
FIG. 7E
FIG. 7F
FIG. 7G
FIG. 7H

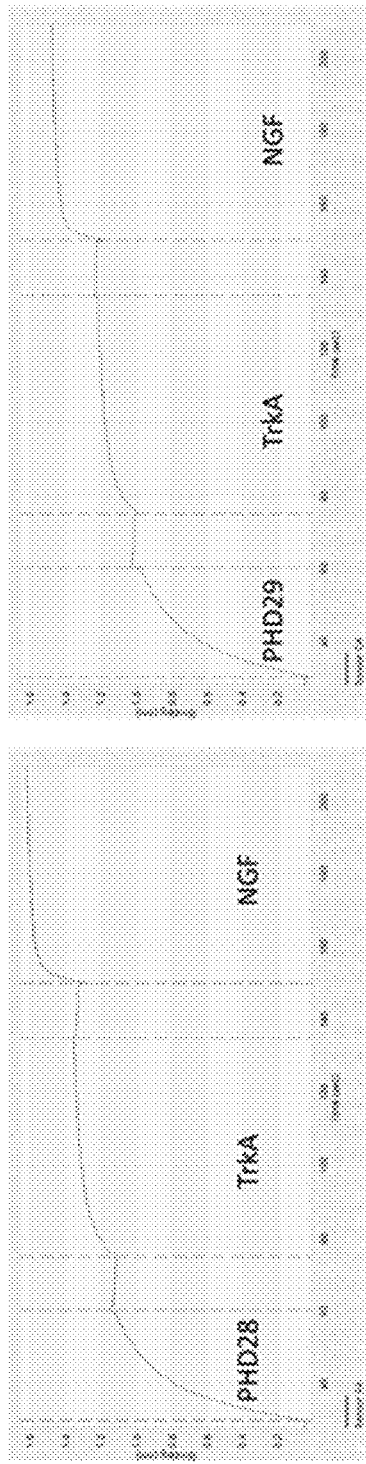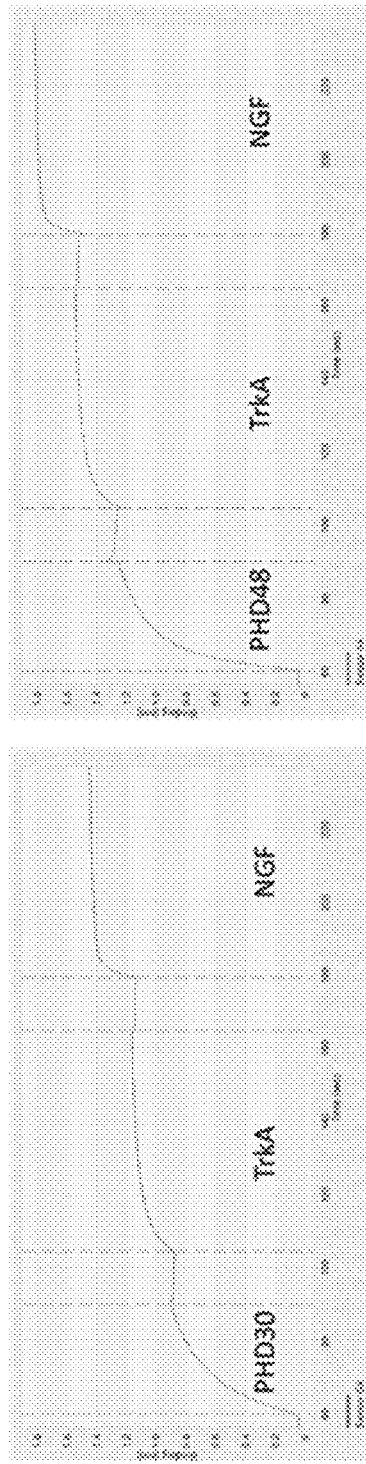

```
                        SEQUENCE LISTING

Sequence total quantity: 134
SEQ ID NO: 1            moltype = AA  length = 5
FEATURE                 Location/Qualifiers
REGION                  1..5
                        note = muPHD31 HCDR1-1
source                  1..5
                        mol_type = protein
                        organism = synthetic construct
SEQUENCE: 1
SYGVH                                                                     5

SEQ ID NO: 2            moltype = AA  length = 10
FEATURE                 Location/Qualifiers
REGION                  1..10
                        note = muPHD31 HCDR1-2
source                  1..10
                        mol_type = protein
                        organism = synthetic construct
SEQUENCE: 2
GFSLTSYGVH                                                               10

SEQ ID NO: 3            moltype = AA  length = 8
FEATURE                 Location/Qualifiers
REGION                  1..8
                        note = muPHD31 HCDR1-3
source                  1..8
                        mol_type = protein
                        organism = synthetic construct
SEQUENCE: 3
GFSLTSYG                                                                  8
```

-continued

```
SEQ ID NO: 4              moltype = AA  length = 16
FEATURE                   Location/Qualifiers
REGION                    1..16
                          note = muPHD31 HCDR2-1
source                    1..16
                          mol_type = protein
                          organism = synthetic construct
SEQUENCE: 4
VIWSGGSTDY NAAFIS                                                          16

SEQ ID NO: 5              moltype = AA  length = 9
FEATURE                   Location/Qualifiers
REGION                    1..9
                          note = muPHD31 HCDR2-2
source                    1..9
                          mol_type = protein
                          organism = synthetic construct
SEQUENCE: 5
VIWSGGSTD                                                                   9

SEQ ID NO: 6              moltype = AA  length = 7
FEATURE                   Location/Qualifiers
REGION                    1..7
                          note = muPHD31 HCDR2-3
source                    1..7
                          mol_type = protein
                          organism = synthetic construct
SEQUENCE: 6
IWSGGST                                                                     7

SEQ ID NO: 7              moltype = AA  length = 10
FEATURE                   Location/Qualifiers
REGION                    1..10
                          note = muPHD31 HCDR3-1; HCDR3-2
source                    1..10
                          mol_type = protein
                          organism = synthetic construct
SEQUENCE: 7
NNWDPWAMDY                                                                 10

SEQ ID NO: 8              moltype = AA  length = 12
FEATURE                   Location/Qualifiers
REGION                    1..12
                          note = muPHD31 HCDR3-3
source                    1..12
                          mol_type = protein
                          organism = synthetic construct
SEQUENCE: 8
ARNNWDPWAM DY                                                              12

SEQ ID NO: 9              moltype = AA  length = 14
FEATURE                   Location/Qualifiers
REGION                    1..14
                          note = muPHD31 LCDR1-1; LCDR1-2
source                    1..14
                          mol_type = protein
                          organism = synthetic construct
SEQUENCE: 9
RSSTGAVTTS NYAN                                                            14

SEQ ID NO: 10             moltype = AA  length = 9
FEATURE                   Location/Qualifiers
REGION                    1..9
                          note = muPHD31 LCDR1-3
source                    1..9
                          mol_type = protein
                          organism = synthetic construct
SEQUENCE: 10
TGAVTTSNY                                                                   9

SEQ ID NO: 11             moltype = AA  length = 7
FEATURE                   Location/Qualifiers
REGION                    1..7
                          note = muPHD31 LCDR2-1; LCDR2-2
source                    1..7
                          mol_type = protein
                          organism = synthetic construct
SEQUENCE: 11
```

```
GTNNRAP                                                                       7

SEQ ID NO: 12          moltype =    length =
SEQUENCE: 12
000

SEQ ID NO: 13          moltype = AA   length = 9
FEATURE                Location/Qualifiers
REGION                 1..9
                       note = muPHD31 LCDR3-1; LCDR3-2; LCDR3-3
source                 1..9
                       mol_type = protein
                       organism = synthetic construct
SEQUENCE: 13
ALWYSNHWV                                                                     9

SEQ ID NO: 14          moltype = AA   length = 118
FEATURE                Location/Qualifiers
REGION                 1..118
                       note = muPHD31 VH
source                 1..118
                       mol_type = protein
                       organism = synthetic construct
SEQUENCE: 14
QVQLKQSGPG LVQPSQSLSI TCTVSGFSLT SYGVHWVRQS PGKGLEWLGV IWSGGSTDYN      60
AAFISRLSIT KDNSKSQVFF KMNSLQANDT AIYYCARNNW DPWAMDYWGQ GTSVTVSS       118

SEQ ID NO: 15          moltype = AA   length = 109
FEATURE                Location/Qualifiers
REGION                 1..109
                       note = muPHD31 VL
source                 1..109
                       mol_type = protein
                       organism = synthetic construct
SEQUENCE: 15
QAVVTQESAL TTSPGETVTL TCRSSTGAVT TSNYANWVQE KPDHLFTGLI GGTNNRAPGV      60
PARFSDSLIG DKAALTITGA QTEDEAIYFC ALWYSNHWVF GGGTKLTVL                 109

SEQ ID NO: 16          moltype = AA   length = 119
FEATURE                Location/Qualifiers
REGION                 1..119
                       note = muPHD48 VH
source                 1..119
                       mol_type = protein
                       organism = synthetic construct
SEQUENCE: 16
EVQLQQSGTV LARPGASVKM SCKASGYSFT TYWMHWVKQR PGQGLEWIGT IYPGNSDSSN      60
NQKFKGKAKL TAVTSASTAY MELSSLTNED SAVYYCTRFY YEDWYFDVWG AGTTVTVSS      119

SEQ ID NO: 17          moltype = DNA   length = 357
FEATURE                Location/Qualifiers
misc_feature           1..357
                       note = muPHD48 VH Nucleic Acid
source                 1..357
                       mol_type = other DNA
                       organism = synthetic construct
SEQUENCE: 17
gaggttcagc tccagcagtc tgggactgtg ctggcaaggc ctggggcttc cgtgaagatg       60
tcctgcaagg cttctggcta cagctttacc acctactgga tgcactgggt aaaacagagg      120
cctggacagg gtctagaatg gattggtact atttatcctg gaaatagtga tagtagtaac      180
aaccagaagt tcaagggcaa ggccaaactg actgcagtca catccgccag cactgcctac      240
atggagctca gcagcctgac aaatgaggac tctgcggtct attactgtac aagatttac      300
tacgaagact ggtacttcga tgtctggggc cagggacca cggtcaccgt ctcctca         357

SEQ ID NO: 18          moltype = AA   length = 106
FEATURE                Location/Qualifiers
REGION                 1..106
                       note = muPHD48 VL
source                 1..106
                       mol_type = protein
                       organism = synthetic construct
SEQUENCE: 18
QIVLTQSPAI MSASPGEKVT ISCSASSSVS YMYWFQQKPG SSPKPWIYRT SNLASGVPAR      60
FSGSGSGTSY SLTISSMEAE DAATYYCQQY HSYPPTFGGG TKLEIK                    106

SEQ ID NO: 19          moltype = DNA   length = 318
FEATURE                Location/Qualifiers
misc_feature           1..318
                       note = muPHD48 VL Nucleic Acid
```

```
                        source              1..318
                                            mol_type = other DNA
                                            organism = synthetic construct
SEQUENCE: 19
caaattgttc tcacccagtc tccagcaatc atgtctgcat ctccagggga gaaggtcacc    60
atatcctgca gtgccagctc aagtgtaagt tacatgtact ggttccagca gaagccagga   120
tcctccccca aaccctggat ttatcgcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtat catagttacc caccgacgtt cggtggaggc   300
accaagctgg aaatcaaa                                                 318

SEQ ID NO: 20           moltype = AA  length = 5
FEATURE                 Location/Qualifiers
REGION                  1..5
                        note =
                        muPHD48/PHD48-01/PHD24/PHD28/PHD25/PHD29/PHD48/PHD48-08
                        HCDR1-1
source                  1..5
                        mol_type = protein
                        organism = synthetic construct
SEQUENCE: 20
TYWMH                                                                 5

SEQ ID NO: 21           moltype = AA  length = 10
FEATURE                 Location/Qualifiers
REGION                  1..10
                        note = muPHD48/PHD48-01 HCDR1-2
source                  1..10
                        mol_type = protein
                        organism = synthetic construct
SEQUENCE: 21
GYSFTTYWMH                                                           10

SEQ ID NO: 22           moltype = AA  length = 8
FEATURE                 Location/Qualifiers
REGION                  1..8
                        note = muPHD48/PHD48-01 HCDR1-3
source                  1..8
                        mol_type = protein
                        organism = synthetic construct
SEQUENCE: 22
GYSFTTYW                                                              8

SEQ ID NO: 23           moltype = AA  length = 17
FEATURE                 Location/Qualifiers
REGION                  1..17
                        note = muPHD48/PHD48-01 HCDR2-1
source                  1..17
                        mol_type = protein
                        organism = synthetic construct
SEQUENCE: 23
TIYPGNSDSS NNQKFKG                                                   17

SEQ ID NO: 24           moltype = AA  length = 10
FEATURE                 Location/Qualifiers
REGION                  1..10
                        note = muPHD48/PHD48-01/PHD30/PHD48/PHD48-08 HCDR2-2
source                  1..10
                        mol_type = protein
                        organism = synthetic construct
SEQUENCE: 24
TIYPGNSDSS                                                           10

SEQ ID NO: 25           moltype = AA  length = 8
FEATURE                 Location/Qualifiers
REGION                  1..8
                        note = muPHD48/PHD48-01/PHD30/PHD48/PHD48-08 HCDR2-3
source                  1..8
                        mol_type = protein
                        organism = synthetic construct
SEQUENCE: 25
IYPGNSDS                                                              8

SEQ ID NO: 26           moltype = AA  length = 10
FEATURE                 Location/Qualifiers
REGION                  1..10
                        note = muPHD48/PHD48-01/PHD30/PHD48/PHD48-08 HCDR3-1;
                        HCDR3-2
source                  1..10
```

```
SEQUENCE: 26
FYYEDWYFDV                                                              10

SEQ ID NO: 27         moltype = AA  length = 12
FEATURE               Location/Qualifiers
REGION                1..12
                      note = muPHD48/PHD48-01/PHD30/PHD48/PHD48-08 HCDR3-3
source                1..12
                      mol_type = protein
                      organism = synthetic construct
SEQUENCE: 27
TRFYYEDWYF DV                                                           12

SEQ ID NO: 28         moltype = AA  length = 10
FEATURE               Location/Qualifiers
REGION                1..10
                      note = muPHD48/PHD48-01/muPHD49/PHD49-01 LCDR1-1; LCDR1-2
source                1..10
                      mol_type = protein
                      organism = synthetic construct
SEQUENCE: 28
SASSSVSYMY                                                              10

SEQ ID NO: 29         moltype = AA  length = 5
FEATURE               Location/Qualifiers
REGION                1..5
                      note = muPHD48/PHD48-01/muPHD49/PHD48/PHD48-08 LCDR1-3
source                1..5
                      mol_type = protein
                      organism = synthetic construct
SEQUENCE: 29
SSVSY                                                                   5

SEQ ID NO: 30         moltype = AA  length = 7
FEATURE               Location/Qualifiers
REGION                1..7
                      note = muPHD48/PHD48-01/PHD48/PHD48-08 LCDR2-1; LCDR2-2
source                1..7
                      mol_type = protein
                      organism = synthetic construct
SEQUENCE: 30
RTSNLAS                                                                 7

SEQ ID NO: 31         moltype =     length =
SEQUENCE: 31
000

SEQ ID NO: 32         moltype = AA  length = 9
FEATURE               Location/Qualifiers
REGION                1..9
                      note = muPHD48/PHD48-01/PHD30/PHD48/PHD48-08 LCDR3-1;
                       LCDR3-2; LCDR3-3
source                1..9
                      mol_type = protein
                      organism = synthetic construct
SEQUENCE: 32
QQYHSYPPT                                                               9

SEQ ID NO: 33         moltype = AA  length = 10
FEATURE               Location/Qualifiers
REGION                1..10
                      note = muPHD49 HCDR1-2
source                1..10
                      mol_type = protein
                      organism = synthetic construct
SEQUENCE: 33
GYTFSSYWMQ                                                              10

SEQ ID NO: 34         moltype = AA  length = 8
FEATURE               Location/Qualifiers
REGION                1..8
                      note = muPHD49 HCDR1-3
source                1..8
                      mol_type = protein
                      organism = synthetic construct
SEQUENCE: 34
GYTFSSYW                                                                8
```

| | | |
|---|---|---|
| SEQ ID NO: 35<br>FEATURE<br>REGION<br><br>source | moltype = AA  length = 10<br>Location/Qualifiers<br>1..10<br>note = muPHD49 HCDR2-2<br>1..10<br>mol_type = protein<br>organism = synthetic construct | |
| SEQUENCE: 35<br>AIYPGDDDTI | | 10 |
| SEQ ID NO: 36<br>FEATURE<br>REGION<br><br>source | moltype = AA  length = 8<br>Location/Qualifiers<br>1..8<br>note = muPHD49 HCDR2-3<br>1..8<br>mol_type = protein<br>organism = synthetic construct | |
| SEQUENCE: 36<br>IYPGDDDT | | 8 |
| SEQ ID NO: 37<br>FEATURE<br>REGION<br><br><br>source | moltype = AA  length = 10<br>Location/Qualifiers<br>1..10<br>note = muPHD49 HCDR3-2; muPHD49/PHD49-01 HCDR3-1; PHD49-05<br> HCDR3; PHD49-11 HCDR3<br>1..10<br>mol_type = protein<br>organism = synthetic construct | |
| SEQUENCE: 37<br>NYDYQAWFAY | | 10 |
| SEQ ID NO: 38<br>FEATURE<br>REGION<br><br>source | moltype = AA  length = 12<br>Location/Qualifiers<br>1..12<br>note = muPHD49 HCDR3-3<br>1..12<br>mol_type = protein<br>organism = synthetic construct | |
| SEQUENCE: 38<br>ARNYDYQAWF AY | | 12 |
| SEQ ID NO: 39<br>FEATURE<br>REGION<br><br><br>source | moltype = AA  length = 7<br>Location/Qualifiers<br>1..7<br>note = muPHD49 LCDR2-2; muPHD49/PHD49-01 LCDR2-1; muPHD50<br> LCDR2; PHD49-11 LCDR2<br>1..7<br>mol_type = protein<br>organism = synthetic construct | |
| SEQUENCE: 39<br>LTSNLAS | | 7 |
| SEQ ID NO: 40<br>SEQUENCE: 40<br>000 | moltype =   length = | |
| SEQ ID NO: 41<br>FEATURE<br>REGION<br><br><br><br>source | moltype = AA  length = 9<br>Location/Qualifiers<br>1..9<br>note = muPHD49 LCDR3-2; muPHD49 LCDR3-3; muPHD49/PHD49-01<br> LCDR3-1; muPHD50 LCDR3; PHD49-05/PHD49 LCDR3; PHD49-11<br> LCDR3; PHD49-21 LCDR3<br>1..9<br>mol_type = protein<br>organism = synthetic construct | |
| SEQUENCE: 41<br>QQWSSNPLT | | 9 |
| SEQ ID NO: 42<br>FEATURE<br>REGION<br><br>source | moltype = AA  length = 119<br>Location/Qualifiers<br>1..119<br>note = muPHD49 VH<br>1..119<br>mol_type = protein<br>organism = synthetic construct | |
| SEQUENCE: 42<br>QVQLQQSGAE LARPGASVKL SCKASGYTFS SYWMQWVKQR PGQGLEWIGA IYPGDDDTIY<br>TQKFKGKATL TADKSSSTAY MQLSSLASED SAVYYCARNY DYQAWFAYWG QGTLVTVSA | | 60<br>119 |

```
SEQ ID NO: 43            moltype = DNA  length = 357
FEATURE                  Location/Qualifiers
misc_feature             1..357
                         note = muPHD49 VH Nucleic Acid
source                   1..357
                         mol_type = other DNA
                         organism = synthetic construct
SEQUENCE: 43
caggttcagc tccagcagtc tggggctgag ctggcaagac ctggggcttc agtgaagttg    60
tcctgcaagg cttctggcta caccttttct agctactgga tgcagtgggt aaaacagagg   120
cctggacagg gtctggaatg gattggggct atttatcctg gagatgatga ctactattac   180
actcagaagt tcaagggcaa ggccacattg actgcagata atcctccag cacagcctac    240
atgcaactca gcagcttggc atctgaggac tctgcggtct attactgtgc aagaaactat   300
gactaccagg gcctggtttg cttactgggc caagggactc tggtcactgt ctctgca      357

SEQ ID NO: 44            moltype = AA  length = 106
FEATURE                  Location/Qualifiers
REGION                   1..106
                         note = muPHD49 VL
source                   1..106
                         mol_type = protein
                         organism = synthetic construct
SEQUENCE: 44
QIVLTQSPAL MSASPGEKVT MTCSASSSVS YMYWYQQKPR SSPKPWIYLT SNLASGVPAR    60
FSGSGSGTSY SLTISSMEAE DAATYYCQQW SSNPLTFGAG TKLELK                  106

SEQ ID NO: 45            moltype = AA  length = 5
FEATURE                  Location/Qualifiers
REGION                   1..5
                         note = muPHD49/PHD49-01 HCDR1-1; PHD49-11 HCDR1
source                   1..5
                         mol_type = protein
                         organism = synthetic construct
SEQUENCE: 45
SYWMQ                                                                 5

SEQ ID NO: 46            moltype = AA  length = 17
FEATURE                  Location/Qualifiers
REGION                   1..17
                         note = muPHD49/PHD49-01 HCDR2-1; PHD49-11 HCDR2
source                   1..17
                         mol_type = protein
                         organism = synthetic construct
SEQUENCE: 46
AIYPGDDDTI YTQKFKG                                                   17

SEQ ID NO: 47            moltype = AA  length = 5
FEATURE                  Location/Qualifiers
REGION                   1..5
                         note = muPHD50 HCDR1
source                   1..5
                         mol_type = protein
                         organism = synthetic construct
SEQUENCE: 47
SYWMH                                                                 5

SEQ ID NO: 48            moltype = AA  length = 17
FEATURE                  Location/Qualifiers
REGION                   1..17
                         note = muPHD50 HCDR2
source                   1..17
                         mol_type = protein
                         organism = synthetic construct
SEQUENCE: 48
AIYPGDSDTN YNQKFKG                                                   17

SEQ ID NO: 49            moltype = AA  length = 12
FEATURE                  Location/Qualifiers
REGION                   1..12
                         note = muPHD50 HCDR3
source                   1..12
                         mol_type = protein
                         organism = synthetic construct
SEQUENCE: 49
YGNYAGYYHM DY                                                        12

SEQ ID NO: 50            moltype = AA  length = 10
FEATURE                  Location/Qualifiers
```

```
REGION                      1..10
                            note = muPHD50 LCDR1
source                      1..10
                            mol_type = protein
                            organism = synthetic construct
SEQUENCE: 50
SASSSVSYIY                                                                    10

SEQ ID NO: 51               moltype = AA  length = 121
FEATURE                     Location/Qualifiers
REGION                      1..121
                            note = muPHD50 VH
source                      1..121
                            mol_type = protein
                            organism = synthetic construct
SEQUENCE: 51
EVQLQQSGTV LARPGASVKM SCKASGYIFT SYWMHWVKQR PGQGLEWIGA IYPGDSDTNY              60
NQKFKGKAKL TAVTSASTAY MELSSLTNED SAVYYCTRYG NYAGYYHMDY WGQGTSVTVS              120
S                                                                             121

SEQ ID NO: 52               moltype = DNA  length = 363
FEATURE                     Location/Qualifiers
misc_feature                1..363
                            note = muPHD50 VH Nucleic Acid
source                      1..363
                            mol_type = other DNA
                            organism = synthetic construct
SEQUENCE: 52
gaggttcagc tccagcagtc tgggactgtg ctggcaaggc ctggggcttc cgtgaagatg              60
tcctgcaagg cttctggcta catctttacc agctactgga tgcactgggt aaaacagagg              120
cctggacagg gtctagaatg gattggtgct atttatcctg gagatagtga tactaactac              180
aaccagaaat tcaagggcaa ggccaaactg actgcagtca catccgccag cactgcctac              240
atggagctca gcagcctgac aaatgaggac tctgcggtct attactgtac aagatatggt              300
aactacgcgg gtactatca tatggactac tggggtcaag gaacctcagt caccgtctcc              360
tca                                                                           363

SEQ ID NO: 53               moltype = AA  length = 106
FEATURE                     Location/Qualifiers
REGION                      1..106
                            note = muPHD50 VL
source                      1..106
                            mol_type = protein
                            organism = synthetic construct
SEQUENCE: 53
QIVLTQSPAL MSASPGEKVT MTCSASSSVS YIYWYQQKPR SSPKPWIYLT SNLASGVPAR              60
FSGSGSGTSY SLTISSMEAE DAATYYCQQW SSNPLTFGAG TKLELK                            106

SEQ ID NO: 54               moltype = DNA  length = 318
FEATURE                     Location/Qualifiers
misc_feature                1..318
                            note = muPHD49 VL Nucleic Acid
source                      1..318
                            mol_type = other DNA
                            organism = synthetic construct
SEQUENCE: 54
caaattgttc tcacacagtc tccagcactc atgtctgcat ctccagggga gaaggtcacc              60
atgacctgca gtgccagttc aagtgtaagt tacatgtact ggtaccagca gaagccaaga              120
tcctccccca aaccctggat ttatctcaca tccaacctgg cttctggagt ccctgctcgc              180
ttcagtggca gtgggtctgg gacctcttac tctctcacaa tcagcagcat ggaggctgaa              240
gatgctgcca cttattactg ccagcagtgg agtagtaacc cactcacgtt cggtgctggg              300
accaagctgg agctgaaa                                                           318

SEQ ID NO: 55               moltype = DNA  length = 318
FEATURE                     Location/Qualifiers
misc_feature                1..318
                            note = muPHD50 VL Nucleic Acid
source                      1..318
                            mol_type = other DNA
                            organism = synthetic construct
SEQUENCE: 55
caaattgttc tcacccagtc tccagcactc atgtctgcat ctccagggga gaaggtcacc              60
atgacctgca gtgccagctc aagtgtaagt tacatatact ggtaccagca gaagccaaga              120
tcctccccca aaccctggat ttatctcaca tccaacctgg cttctggagt ccctgctcgc              180
ttcagtggca gtgggtctgg gacctcttac tctctcacaa tcagcagcat ggaggctgaa              240
gatgctgcca cttattactg ccagcagtgg agtagtaacc cgctcacgtt cggtgctggg              300
accaagctgg agctgaaa                                                           318

SEQ ID NO: 56               moltype = AA  length = 10
FEATURE                     Location/Qualifiers
```

```
REGION                  1..10
                        note = PHD22/PHD24/PHD25/PHD26/PHD28/PHD29 LCDR1-1; LCDR1-2
source                  1..10
                        mol_type = protein
                        organism = synthetic construct
SEQUENCE: 56
RASSSISWLY                                                                        10

SEQ ID NO: 57           moltype = AA  length = 5
FEATURE                 Location/Qualifiers
REGION                  1..5
                        note = PHD22/PHD24/PHD25/PHD26/PHD28/PHD29 LCDR1-3
source                  1..5
                        mol_type = protein
                        organism = synthetic construct
SEQUENCE: 57
SSISW                                                                              5

SEQ ID NO: 58           moltype = AA  length = 7
FEATURE                 Location/Qualifiers
REGION                  1..7
                        note = PHD22/PHD24/PHD25 LCDR2-1; LCDR2-2
source                  1..7
                        mol_type = protein
                        organism = synthetic construct
SEQUENCE: 58
YTSTLGS                                                                            7

SEQ ID NO: 59           moltype =     length =
SEQUENCE: 59
000

SEQ ID NO: 60           moltype = AA  length = 9
FEATURE                 Location/Qualifiers
REGION                  1..9
                        note = PHD22/PHD24/PHD25/PHD26/PHD28/PHD29 LCDR3-1;
                          LCDR3-2; LCDR3-3
source                  1..9
                        mol_type = protein
                        organism = synthetic construct
SEQUENCE: 60
QQWHSYPPT                                                                          9

SEQ ID NO: 61           moltype = AA  length = 106
FEATURE                 Location/Qualifiers
REGION                  1..106
                        note = PHD22/PHD24/PHD25 VL
source                  1..106
                        mol_type = protein
                        organism = synthetic construct
SEQUENCE: 61
DIQMTQSPSS LSASVGDRVT ITCRASSSIS WLYWFQQKPG KAPKPLIYYT STLGSGVPSR                  60
FSGSGSGTDY TLTISSLQPE DFATYYCQQW HSYPPTFGGG TKVEIK                                106

SEQ ID NO: 62           moltype = AA  length = 5
FEATURE                 Location/Qualifiers
REGION                  1..5
                        note = PHD22/PHD26/PHD30 HCDR1-1
source                  1..5
                        mol_type = protein
                        organism = synthetic construct
SEQUENCE: 62
EYWMH                                                                              5

SEQ ID NO: 63           moltype = AA  length = 10
FEATURE                 Location/Qualifiers
REGION                  1..10
                        note = PHD22/PHD26/PHD30 HCDR1-2
source                  1..10
                        mol_type = protein
                        organism = synthetic construct
SEQUENCE: 63
GYTFTEYWMH                                                                        10

SEQ ID NO: 64           moltype = AA  length = 8
FEATURE                 Location/Qualifiers
REGION                  1..8
                        note = PHD22/PHD26/PHD30 HCDR1-3
source                  1..8
```

```
                        mol_type = protein
                        organism = synthetic construct
SEQUENCE: 64
GYTFTEYW                                                                 8

SEQ ID NO: 65           moltype = AA   length = 17
FEATURE                 Location/Qualifiers
REGION                  1..17
                        note = PHD22/PHD26 HCDR2-1
source                  1..17
                        mol_type = protein
                        organism = synthetic construct
SEQUENCE: 65
TIYPGNSDTS YAQKFQG                                                       17

SEQ ID NO: 66           moltype = AA   length = 10
FEATURE                 Location/Qualifiers
REGION                  1..10
                        note = PHD22/PHD26/PHD24/PHD28/PHD25/PHD29 HCDR2-2
source                  1..10
                        mol_type = protein
                        organism = synthetic construct
SEQUENCE: 66
TIYPGNSDTS                                                               10

SEQ ID NO: 67           moltype = AA   length = 8
FEATURE                 Location/Qualifiers
REGION                  1..8
                        note = PHD22/PHD26/PHD24/PHD28/PHD25/PHD29 HCDR2-3
source                  1..8
                        mol_type = protein
                        organism = synthetic construct
SEQUENCE: 67
IYPGNSDT                                                                 8

SEQ ID NO: 68           moltype = AA   length = 10
FEATURE                 Location/Qualifiers
REGION                  1..10
                        note = PHD22/PHD26/PHD24/PHD28/PHD25/PHD29 HCDR3-1; HCDR3-2
source                  1..10
                        mol_type = protein
                        organism = synthetic construct
SEQUENCE: 68
FYFEDWYFDV                                                               10

SEQ ID NO: 69           moltype = AA   length = 12
FEATURE                 Location/Qualifiers
REGION                  1..12
                        note = PHD22/PHD26/PHD24/PHD28/PHD25/PHD29 HCDR3-3
source                  1..12
                        mol_type = protein
                        organism = synthetic construct
SEQUENCE: 69
TRFYFEDWYF DV                                                            12

SEQ ID NO: 70           moltype = AA   length = 119
FEATURE                 Location/Qualifiers
REGION                  1..119
                        note = PHD22/PHD26 VH
source                  1..119
                        mol_type = protein
                        organism = synthetic construct
SEQUENCE: 70
QVQLVQSGAE VKKPGASVKV SCKASGYTFT EYWMHWVRQA PGQGLEWIGT IYPGNSDTSY         60
AQKFQGRVTL TRDTSTSTAY MELSSLRSED TAVYYCTRFY FEDWYFDVWG QGTTVTVSS         119

SEQ ID NO: 71           moltype = AA   length = 10
FEATURE                 Location/Qualifiers
REGION                  1..10
                        note = PHD24/PHD28/PHD25/PHD29/PHD48/PHD48-08 HCDR1-2
source                  1..10
                        mol_type = protein
                        organism = synthetic construct
SEQUENCE: 71
GYTFTTYWMH                                                               10

SEQ ID NO: 72           moltype = AA   length = 8
FEATURE                 Location/Qualifiers
REGION                  1..8
```

```
                              note = PHD24/PHD28/PHD25/PHD29/PHD48/PHD48-08 HCDR1-3
source                        1..8
                              mol_type = protein
                              organism = synthetic construct
SEQUENCE: 72
GYTFTTYW                                                                          8

SEQ ID NO: 73             moltype = AA  length = 17
FEATURE                   Location/Qualifiers
REGION                    1..17
                          note = PHD24/PHD28 HCDR2-1
source                    1..17
                          mol_type = protein
                          organism = synthetic construct
SEQUENCE: 73
TIYPGNSDTS LAQKFQG                                                               17

SEQ ID NO: 74             moltype = AA  length = 119
FEATURE                   Location/Qualifiers
REGION                    1..119
                          note = PHD24/PHD28 VH
source                    1..119
                          mol_type = protein
                          organism = synthetic construct
SEQUENCE: 74
QVQLVQSGAE VKKPGASVKV SCKASGYTFT TYWMHWVRQA PGQGLEWIGT IYPGNSDTSL                 60
AQKFQGRVTL TRDTSTSTAY MELSSLRSED TAVYYCTRFY FEDWYFDVWG QGTTVTVSS                 119

SEQ ID NO: 75             moltype = AA  length = 17
FEATURE                   Location/Qualifiers
REGION                    1..17
                          note = PHD25/PHD29 HCDR2-1
source                    1..17
                          mol_type = protein
                          organism = synthetic construct
SEQUENCE: 75
TIYPGNSDTS FAQKFQG                                                               17

SEQ ID NO: 76             moltype = AA  length = 119
FEATURE                   Location/Qualifiers
REGION                    1..119
                          note = PHD25/PHD29 VH
source                    1..119
                          mol_type = protein
                          organism = synthetic construct
SEQUENCE: 76
QVQLVQSGAE VKKPGASVKV SCKASGYTFT TYWMHWVRQA PGQGLEWIGT IYPGNSDTSF                 60
AQKFQGRVTL TRDTSTSTAY MELSSLRSED TAVYYCTRFY FEDWYFDVWG QGTTVTVSS                 119

SEQ ID NO: 77             moltype = AA  length = 7
FEATURE                   Location/Qualifiers
REGION                    1..7
                          note = PHD26/PHD28/PHD29 LCDR2-1; LCDR2-2
source                    1..7
                          mol_type = protein
                          organism = synthetic construct
SEQUENCE: 77
YTSSLGS                                                                           7

SEQ ID NO: 78             moltype = AA  length = 106
FEATURE                   Location/Qualifiers
REGION                    1..106
                          note = PHD26/PHD28/PHD29 VL
source                    1..106
                          mol_type = protein
                          organism = synthetic construct
SEQUENCE: 78
DIQMTQSPSS LSASVGDRVT ITCRASSSIS WLYWFQQKPG KAPKPLIYYT SSLGSGVPSR                 60
FSGSGSGTDY TLTISSLQPE DFATYYCQQW HSYPPTFGGG TKVEIK                               106

SEQ ID NO: 79             moltype = AA  length = 17
FEATURE                   Location/Qualifiers
REGION                    1..17
                          note = PHD30 HCDR2-1
source                    1..17
                          mol_type = protein
                          organism = synthetic construct
SEQUENCE: 79
TIYPGNSDSS FAQKFQG                                                               17
```

```
SEQ ID NO: 80              moltype = AA  length = 10
FEATURE                    Location/Qualifiers
REGION                     1..10
                           note = PHD30 LCDR1-1; LCDR2-2
source                     1..10
                           mol_type = protein
                           organism = synthetic construct
SEQUENCE: 80
RASSSISYLY                                                          10

SEQ ID NO: 81              moltype = AA  length = 5
FEATURE                    Location/Qualifiers
REGION                     1..5
                           note = PHD30 LCDR1-3
source                     1..5
                           mol_type = protein
                           organism = synthetic construct
SEQUENCE: 81
SSISY                                                                5

SEQ ID NO: 82              moltype = AA  length = 7
FEATURE                    Location/Qualifiers
REGION                     1..7
                           note = PHD30 LCDR2-1; LCDR2-2
source                     1..7
                           mol_type = protein
                           organism = synthetic construct
SEQUENCE: 82
RTSSLGS                                                              7

SEQ ID NO: 83              moltype =     length =
SEQUENCE: 83
000

SEQ ID NO: 84              moltype = AA  length = 119
FEATURE                    Location/Qualifiers
REGION                     1..119
                           note = PHD30 VH
source                     1..119
                           mol_type = protein
                           organism = synthetic construct
SEQUENCE: 84
QVQLVQSGAE VKKPGASVKV SCKASGYTFT EYWMHWVRQA PGQGLEWIGT IYPGNSDSSF   60
AQKFQGRVTL TRDTSTSTAY MELSSLRSED TAVYYCTRFY YEDWYFDVWG QGTTVTVSS   119

SEQ ID NO: 85              moltype = AA  length = 106
FEATURE                    Location/Qualifiers
REGION                     1..106
                           note = PHD30 VL
source                     1..106
                           mol_type = protein
                           organism = synthetic construct
SEQUENCE: 85
DIQMTQSPSS LSASVGDRVT ITCRASSSIS YLYWFQQKPG KAPKPLIYRT SSLGSGVPSR   60
FSGSGSGTDY TLTISSLQPE DFATYYCQQY HSYPPTFGGG TKVEIK                106

SEQ ID NO: 86              moltype = AA  length = 119
FEATURE                    Location/Qualifiers
REGION                     1..119
                           note = PHD48 VH
source                     1..119
                           mol_type = protein
                           organism = synthetic construct
SEQUENCE: 86
QVQLVQSGAE VKKPGASVKV SCKASGYTFT TYWMHWVRQA PGQGLEWIGT IYPGNSDSSN   60
AQKFQGRVTL TRDTSTSTAY MELSSLRSED TAVYYCTRFY YEDWYFDVWG QGTTVTVSS   119

SEQ ID NO: 87              moltype = AA  length = 17
FEATURE                    Location/Qualifiers
REGION                     1..17
                           note = PHD48/PHD48-08 HCDR2-1
source                     1..17
                           mol_type = protein
                           organism = synthetic construct
SEQUENCE: 87
TIYPGNSDSS NAQKFQG                                                  17

SEQ ID NO: 88              moltype = AA  length = 10
```

```
FEATURE                 Location/Qualifiers
REGION                  1..10
                        note = PHD48/PHD48-08 LCDR1-1; PHD48/PHD48-08 LCDR1-2;
                        PHD49-05/PHD49 LCDR1; PHD49-11 LCDR1; PHD49-21 LCDR1
source                  1..10
                        mol_type = protein
                        organism = synthetic construct
SEQUENCE: 88
RASSSVSYLY                                                                      10

SEQ ID NO: 89           moltype = AA  length = 119
FEATURE                 Location/Qualifiers
REGION                  1..119
                        note = PHD48-01 VH
source                  1..119
                        mol_type = protein
                        organism = synthetic construct
SEQUENCE: 89
QVQLVQSGAE VKKPGASVKV SCKASGYSFT TYWMHWVRQA PGQGLEWIGT IYPGNSDSSN               60
NQKFKGRATL TADTSTSTAY MELSSLRSED TAVYYCTRFY YEDWYFDVWG QGTMVTVSS                119

SEQ ID NO: 90           moltype = AA  length = 106
FEATURE                 Location/Qualifiers
REGION                  1..106
                        note = PHD48-01 VL
source                  1..106
                        mol_type = protein
                        organism = synthetic construct
SEQUENCE: 90
DIQMTQSPSS LSASVGDRVT ITCSASSSVS YMYWFQQKPG KAPKPWIYRT SNLASGVPSR               60
FSGSGSGTDY TLTISSLQPE DFATYYCQQY HSYPPTFGGG TKVEIK                              106

SEQ ID NO: 91           moltype = AA  length = 106
FEATURE                 Location/Qualifiers
REGION                  1..106
                        note = PHD48-08/PHD48_VL
source                  1..106
                        mol_type = protein
                        organism = synthetic construct
SEQUENCE: 91
DIQMTQSPSS LSASVGDRVT ITCRASSSVS YLYWFQQKPG KAPKPLIYRT SNLASGVPSR               60
FSGSGSGTDY TLTISSLQPE DFATYYCQQY HSYPPTFGGG TKVEIK                              106

SEQ ID NO: 92           moltype = AA  length = 119
FEATURE                 Location/Qualifiers
REGION                  1..119
                        note = PHD48-08_VH
source                  1..119
                        mol_type = protein
                        organism = synthetic construct
SEQUENCE: 92
QVQLVQSGAE VKKPGASVKV SCKASGYTFT TYWMHWVRQA PGQGLEWIGT IYPGNSDSSN               60
AQKFQGRVTL TADTSTSTAY MELSSLRSED TAVYYCTRFY YEDWYFDVWG QGTTVTVSS                119

SEQ ID NO: 93           moltype = AA  length = 5
FEATURE                 Location/Qualifiers
REGION                  1..5
                        note = PHD48 related HCDR1 general formula
VARIANT                 1
                        note = misc_feature - Xaa = Glu or Thr
source                  1..5
                        mol_type = protein
                        organism = synthetic construct
SEQUENCE: 93
XYWMH                                                                           5

SEQ ID NO: 94           moltype = AA  length = 17
FEATURE                 Location/Qualifiers
REGION                  1..17
                        note = PHD48 related HCDR2 general formula
VARIANT                 9
                        note = misc_feature - Xaa = Ser or Thr
VARIANT                 11
                        note = misc_feature - Xaa = Phe, Leu, Asn or Tyr
VARIANT                 12
                        note = misc_feature - Xaa = Ala or Asn
VARIANT                 16
                        note = misc_feature - Xaa = Lys or Gln
source                  1..17
```

```
                        mol_type = protein
                        organism = synthetic construct
SEQUENCE: 94
TIYPGNSDXS XXQKFXG                                                  17

SEQ ID NO: 95           moltype = AA   length = 10
FEATURE                 Location/Qualifiers
REGION                  1..10
                        note = PHD48 related HCDR3 general formula
VARIANT                 3
                        note = misc_feature - Xaa = Phe or Tyr
source                  1..10
                        mol_type = protein
                        organism = synthetic construct
SEQUENCE: 95
FYXEDWYFDV                                                          10

SEQ ID NO: 96           moltype = AA   length = 10
FEATURE                 Location/Qualifiers
REGION                  1..10
                        note = PHD48 related LCDR1 general formula
VARIANT                 1
                        note = misc_feature - Xaa = Arg or Ser
VARIANT                 6
                        note = misc_feature - Xaa = Ile or Val
VARIANT                 8
                        note = misc_feature - Xaa = Trp or Tyr
VARIANT                 9
                        note = misc_feature - Xaa = Leu or Met
source                  1..10
                        mol_type = protein
                        organism = synthetic construct
SEQUENCE: 96
XASSSXSXXY                                                          10

SEQ ID NO: 97           moltype = AA   length = 7
FEATURE                 Location/Qualifiers
REGION                  1..7
                        note = PHD48 related LCDR2 general formula
VARIANT                 1
                        note = misc_feature - Xaa = Arg or Tyr
VARIANT                 4
                        note = misc_feature - Xaa = Asn, Ser or Thr
VARIANT                 6
                        note = misc_feature - Xaa = Ala or Gly
source                  1..7
                        mol_type = protein
                        organism = synthetic construct
SEQUENCE: 97
XTSXLXS                                                             7

SEQ ID NO: 98           moltype = AA   length = 9
FEATURE                 Location/Qualifiers
REGION                  1..9
                        note = PHD48 related LCDR3 general formula
VARIANT                 3
                        note = misc_feature - Xaa = Trp or Tyr
source                  1..9
                        mol_type = protein
                        organism = synthetic construct
SEQUENCE: 98
QQXHSYPPT                                                           9

SEQ ID NO: 99           moltype = AA   length = 119
FEATURE                 Location/Qualifiers
REGION                  1..119
                        note = PHD49-01 VH
source                  1..119
                        mol_type = protein
                        organism = synthetic construct
SEQUENCE: 99
QVQLVQSGAE VKKPGSSVKV SCKASGYTFS SYWMQWVRQA PGQGLEWIGA IYPGDDDTIY    60
TQKFKGRATL TADKSTSTAY MELSSLRSED TAVYYCARNY DYQAWFAYWG QGTLVTVSS    119

SEQ ID NO: 100          moltype = AA   length = 106
FEATURE                 Location/Qualifiers
REGION                  1..106
                        note = PHD49-01 VL
source                  1..106
```

```
                            mol_type = protein
                            organism = synthetic construct
SEQUENCE: 100
DIQMTQSPSS LSASVGDRVT ITCSASSSVS YMYWYQQKPG KAPKPWIYLT SNLASGVPSR   60
FSGSGSGTDY TLTISSLQPE DFATYYCQQW SSNPLTFGQG TKLEIK                 106

SEQ ID NO: 101              moltype = AA   length = 5
FEATURE                     Location/Qualifiers
REGION                      1..5
                            note = PHD49-05 HCDR1
source                      1..5
                            mol_type = protein
                            organism = synthetic construct
SEQUENCE: 101
SHWIQ                                                                5

SEQ ID NO: 102              moltype = AA   length = 17
FEATURE                     Location/Qualifiers
REGION                      1..17
                            note = PHD49-05 HCDR2
source                      1..17
                            mol_type = protein
                            organism = synthetic construct
SEQUENCE: 102
AIYPGDDDTI YTQKFQG                                                  17

SEQ ID NO: 103              moltype = AA   length = 7
FEATURE                     Location/Qualifiers
REGION                      1..7
                            note = PHD49-05/PHD49 LCDR2
source                      1..7
                            mol_type = protein
                            organism = synthetic construct
SEQUENCE: 103
LTSSLAS                                                              7

SEQ ID NO: 104              moltype = AA   length = 106
FEATURE                     Location/Qualifiers
REGION                      1..106
                            note = PHD49-05/PHD49_VL
source                      1..106
                            mol_type = protein
                            organism = synthetic construct
SEQUENCE: 104
DIQMTQSPSS LSASVGDRVT ITCRASSSVS YLYWYQQKPG KAPKPLIYLT SSLASGVPSR   60
FSGSGSGTDY TLTISSLQPE DFATYYCQQW SSNPLTFGQG TKLEIK                 106

SEQ ID NO: 105              moltype = AA   length = 119
FEATURE                     Location/Qualifiers
REGION                      1..119
                            note = PHD49-05_VH
source                      1..119
                            mol_type = protein
                            organism = synthetic construct
SEQUENCE: 105
QVQLVQSGAE VKKPGSSVKV SCKASGYTFS SHWIQWVRQA PGQGLEWIGA IYPGDDDTIY   60
TQKFQGRATI TTDKSTSTAY MELSSLRSED TAVYYCARNY DYQAWFAYWG QGTLVTVSS   119

SEQ ID NO: 106              moltype = AA   length = 119
FEATURE                     Location/Qualifiers
REGION                      1..119
                            note = PHD49-11_VH
source                      1..119
                            mol_type = protein
                            organism = synthetic construct
SEQUENCE: 106
QVQLVQSGAE VKKPGSSVKV SCKASGYTFS SYWMQWVRQA PGQGLEWIGA IYPGDDDTIY   60
TQKFKGRATI TADKSTSTAY MELSSLRSED TAVYYCARNY DYQAWFAYWG QGTLVTVSS   119

SEQ ID NO: 107              moltype = AA   length = 106
FEATURE                     Location/Qualifiers
REGION                      1..106
                            note = PHD49-11_VL
source                      1..106
                            mol_type = protein
                            organism = synthetic construct
SEQUENCE: 107
DIQMTQSPSS LSASVGDRVT ITCRASSSVS YLYWYQQKPG KAPKPWIYLT SNLASGVPSR   60
FSGSGSGTDY TLTISSLQPE DFATYYCQQW SSNPLTFGQG TKLEIK                 106
```

```
SEQ ID NO: 108          moltype = AA   length = 7
FEATURE                 Location/Qualifiers
REGION                  1..7
                        note = PHD49-21 LCDR2
source                  1..7
                        mol_type = protein
                        organism = synthetic construct
SEQUENCE: 108
LTSDLAS                                                                    7

SEQ ID NO: 109          moltype = AA   length = 5
FEATURE                 Location/Qualifiers
REGION                  1..5
                        note = PHD49-21/PHD49 HCDR1
source                  1..5
                        mol_type = protein
                        organism = synthetic construct
SEQUENCE: 109
SYWIQ                                                                      5

SEQ ID NO: 110          moltype = AA   length = 17
FEATURE                 Location/Qualifiers
REGION                  1..17
                        note = PHD49-21/PHD49 HCDR2
source                  1..17
                        mol_type = protein
                        organism = synthetic construct
SEQUENCE: 110
AIYTGDGDTI YTQKFQG                                                        17

SEQ ID NO: 111          moltype = AA   length = 10
FEATURE                 Location/Qualifiers
REGION                  1..10
                        note = PHD49-21/PHD49 HCDR3
source                  1..10
                        mol_type = protein
                        organism = synthetic construct
SEQUENCE: 111
NYHYQAWFDY                                                                10

SEQ ID NO: 112          moltype = AA   length = 119
FEATURE                 Location/Qualifiers
REGION                  1..119
                        note = PHD49-21/PHD49_VH
source                  1..119
                        mol_type = protein
                        organism = synthetic construct
SEQUENCE: 112
QVQLVQSGAE VKKPGSSVKV SCKASGFTFS SYWIQWVRQA PGQGLEWIGA IYTGDGDTIY          60
TQKFQGRATI TTDESTSTAY MELSSLRSED TAVYYCARNY HYQAWFDYWG QGTLVTVSS          119

SEQ ID NO: 113          moltype = AA   length = 106
FEATURE                 Location/Qualifiers
REGION                  1..106
                        note = PHD49-21_VL
source                  1..106
                        mol_type = protein
                        organism = synthetic construct
SEQUENCE: 113
DIQMTQSPSS LSASVGDRVT ITCRASSSVS YLYWYQQKPG KAPKPLIYLT SDLASGVPSR          60
FSGSGSGTDY TLTISSLQPE DFATYYCQQW SSNPLTFGQG TKLEIK                        106

SEQ ID NO: 114          moltype =      length =
SEQUENCE: 114
000

SEQ ID NO: 115          moltype = AA   length = 17
FEATURE                 Location/Qualifiers
REGION                  1..17
                        note = PHD49 related HCDR2 general formula
VARIANT                 4
                        note = misc_feature - Xaa = Pro or Thr
VARIANT                 7
                        note = misc_feature - Xaa = Asp or Gly
VARIANT                 16
                        note = misc_feature - Xaa = Lys or Gln
source                  1..17
                        mol_type = protein
```

```
                                  -continued
                        organism = synthetic construct
SEQUENCE: 115
AIYXGDXDTI YTQKFXG                                                       17

SEQ ID NO: 116          moltype = AA  length = 10
FEATURE                 Location/Qualifiers
REGION                  1..10
                        note = PHD49 related HCDR3 general formula
VARIANT                 3
                        note = misc_feature - Xaa = Asp or His
VARIANT                 9
                        note = misc_feature - Xaa = Ala or Asp
source                  1..10
                        mol_type = protein
                        organism = synthetic construct
SEQUENCE: 116
NYXYQAWFXY                                                               10

SEQ ID NO: 117          moltype = AA  length = 10
FEATURE                 Location/Qualifiers
REGION                  1..10
                        note = PHD49 related LCDR1 general formula
VARIANT                 1
                        note = misc_feature - Xaa = Arg or Ser
VARIANT                 9
                        note = misc_feature - Xaa = Leu or Met
source                  1..10
                        mol_type = protein
                        organism = synthetic construct
SEQUENCE: 117
XASSSVSYXY                                                               10

SEQ ID NO: 118          moltype = AA  length = 7
FEATURE                 Location/Qualifiers
REGION                  1..7
                        note = PHD49 related LCDR2 general formula
VARIANT                 4
                        note = misc_feature - Xaa = Asp, Asn or Ser
source                  1..7
                        mol_type = protein
                        organism = synthetic construct
SEQUENCE: 118
LTSXLAS                                                                  7

SEQ ID NO: 119          moltype = AA  length = 796
FEATURE                 Location/Qualifiers
source                  1..796
                        mol_type = protein
                        organism = Homo sapiens
SEQUENCE: 119
MLRGGRRGQL GWHSWAAGPG SLLAWLILAS AGAAPCPDAC CPHGSSGLRC TRDGALDSLH         60
HLPGAENLTE LYIENQQHLQ HLELRDLRGL GELRNLTIVK SGLRFVAPDA FHFTPRLSRL        120
NLSFNALESL SWKTVQGLSL QELVLSGNPL HCSCALRWLQ RWEEEGLGGV PEQKLQCHGQ        180
GPLAHMPNAS CGVPTLKVQV PNASVDVGDD VLLRCQVEGR GLEQAGWILT ELEQSATVMK        240
SGGLPSLGLT LANVTSDLNR KNVTCWAEND VGRAEVSVQV NVSFPASVQL HTAVEMHHWC        300
IPFSVDGQPA PSLRWLFNGS VLNETSFIFT EFLEPAANET VRHGCLRLNQ PTHVNNGNYT        360
LLAANPFGQA SASIMAAFMD NPFEFNPEDP IPVSFSPVDT NSTSGDPVEK KDETPFGVSV        420
AVGLAVFACL FLSTLLLVLN KCGRRNKFGI NRPAVLAPED GLAMSLHFMT LGGSSLSPTE        480
GKGSGLQGHI IENPQYFSDA CVHHIKRRDI VLKWELGEGA FGKVFLAECH NLLPEQDKML        540
VAVKALKEAS ESARQDFQRE AELLTMLQHQ HIVRFFGVCT EGRPLLMVFE YMRHGDLNRF        600
LRSHGPDAKL LAGGEDVAPG PLGLGQLLAV ASQVAAGMVY LAGLHFVHRD LATRNCLVGQ        660
GLVVKIGDFG MSRDIYSTDY YRVGGRTMLP IRWMPPESIL YRKFTTESDV WSFGVVLWEI        720
FTYGKQPWYQ LSNTEAIDCI TQGRELERPR ACPPEVYAIM RGCWQREPQQ RHSIKDVHAR        780
LQALAQAPPV YLDVLG                                                       796

SEQ ID NO: 120          moltype = AA  length = 391
FEATURE                 Location/Qualifiers
source                  1..391
                        mol_type = protein
                        organism = Homo sapiens
SEQUENCE: 120
AAPCPDACCP HGSSGLRCTR DGALDSLHHL PGAENLTELY IENQQHLQHL ELRDLRGLGE         60
LRNLTIVKSG LRFVAPDAFH FTPRLSRLNL SFNALESLSW KTVQGLSLQE LVLSGNPLHC        120
SCALRWLQRW EEEGLGGVPE QKLQCHGQGP LAHMPNASCG VPTLKVQVPN ASVDVGDDVL        180
LRCQVEGRGL EQAGWILTEL EQSATVMKSG GLPSLGLTLA NVTSDLNRKN VTCWAENDVG        240
RAEVSVQVNV SFPASVQLHT AVEMHHWCIP FSVDGQPAPS LRWLFNGSVL NETSFIFTEF        300
LEPAANETVR HGCLRLNQPT HVNNGNYTLL AANPFGQASA SIMAAFMDNP FEFNPEDPIP        360
VSFSPVDTNS TSGDPVEKKD ETPFGVSVAV G                                      391
```

```
SEQ ID NO: 121            moltype = AA  length = 107
FEATURE                   Location/Qualifiers
REGION                    1..107
                          note = light chain constant region (IgK)
source                    1..107
                          mol_type = protein
                          organism = synthetic construct
SEQUENCE: 121
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                  107

SEQ ID NO: 122            moltype = AA  length = 327
FEATURE                   Location/Qualifiers
REGION                    1..327
                          note = heavy chain constant regionIgG4
source                    1..327
                          mol_type = protein
                          organism = synthetic construct
SEQUENCE: 122
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEAAGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSKL TVDKSRWQEG    300
NVFSCSVMHE ALHNHYTQKS LSLSLGK                                        327

SEQ ID NO: 123            moltype = AA  length = 116
FEATURE                   Location/Qualifiers
REGION                    1..116
                          note = pAb01 VH
source                    1..116
                          mol_type = protein
                          organism = synthetic construct
SEQUENCE: 123
EVQLVESGGG LVKPGGSLRL SCAASGFTFS GVSINWVRQA PGKGLEWVSS ETTSSGTIYY     60
ADSVKGRFTI SRDNAKNSLY LQMNSLRAED TAVYYCARSY YYGMDVWGQG TTVTVS        116

SEQ ID NO: 124            moltype = AA  length = 112
FEATURE                   Location/Qualifiers
REGION                    1..112
                          note = pAb01 VL
source                    1..112
                          mol_type = protein
                          organism = synthetic construct
SEQUENCE: 124
DIVMTQTPLS SPVTLGQPAS ISCRSSQSLV HRNGNTYLSW LQQRPGQPPR LLIYKISNRF     60
SGVPDRFSGS GAGTDFTLKI SRVEAEDVGV YYCMQARQFP LTFGGGTKVE IK            112

SEQ ID NO: 125            moltype = AA  length = 119
FEATURE                   Location/Qualifiers
REGION                    1..119
                          note = Anti-TNP VH
source                    1..119
                          mol_type = protein
                          organism = synthetic construct
SEQUENCE: 125
QVQLQQSGPE LVKPGASVRI SCKASGYTFT SYYIHWVKQR PGQGLEWIGW IYPGNVNTKY     60
NEKFKGKATL TADKSSSTAY MQLSSLTSED SAVYFCARNY GSSYGLAYWG QGTTVTVSS    119

SEQ ID NO: 126            moltype = AA  length = 107
FEATURE                   Location/Qualifiers
REGION                    1..107
                          note = Anti-TNP VL
source                    1..107
                          mol_type = protein
                          organism = synthetic construct
SEQUENCE: 126
DIVMTQSPKF MSTSVGGRVS ITCKASQNVG TAVAWYQQKP GQSPKLLIYS ASNRYTGVPD     60
RFTGSGSGTD FTLTISNMQS EDLADYFCQQ YSSYPLTFGA GTKLEIK                 107

SEQ ID NO: 127            moltype = AA  length = 121
FEATURE                   Location/Qualifiers
REGION                    1..121
                          note = Tanezumab VH
source                    1..121
                          mol_type = protein
                          organism = synthetic construct
SEQUENCE: 127
QVQLQESGPG LVKPSETLSL TCTVSGFSLI GYDLNWIRQP PGKGLEWIGI IWGDGTTDYN     60
```

-continued

```
SAVKSRVTIS KDTSKNQFSL KLSSVTAADT AVYYCARGGY WYATSYYFDY WGQGTLVTVS    120
S                                                                  121

SEQ ID NO: 128          moltype = AA  length = 107
FEATURE                 Location/Qualifiers
REGION                  1..107
                        note = Tanezumab VL
source                  1..107
                        mol_type = protein
                        organism = synthetic construct
SEQUENCE: 128
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKLEIK                 107

SEQ ID NO: 129          moltype = AA  length = 119
FEATURE                 Location/Qualifiers
REGION                  1..119
                        note = Fasinumab VH
source                  1..119
                        mol_type = protein
                        organism = synthetic construct
SEQUENCE: 129
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIF GVVTNFDNWG QGTLVTVSS    119

SEQ ID NO: 130          moltype = AA  length = 107
FEATURE                 Location/Qualifiers
REGION                  1..107
                        note = Fasinumab VL
source                  1..107
                        mol_type = protein
                        organism = synthetic construct
SEQUENCE: 130
DIQMTQSPSS LSASAGDRVT ITCRASQAIR NDLGWYQQKP GKAPKRLIYA AFNLQSGVPS    60
RFSGSGSGTE FTLTISSLQP EDLASYYCQQ YNRYPWTFGQ GTKVEIK                 107

SEQ ID NO: 131          moltype = AA  length = 119
FEATURE                 Location/Qualifiers
REGION                  1..119
                        note = muPHD48 VH; PHD22/PHD26 VH; PHD24/PHD28 VH;
                         PHD25/PHD29 VH; PHD30 VH; PHD48 VH; PHD48-01 VH;
                         PHD48-08_VH general formula
VARIANT                 1
                        note = misc_feature - Xaa = Glu or Gln
VARIANT                 5
                        note = misc_feature - Xaa = Gln or Val
VARIANT                 9
                        note = misc_feature - Xaa = Ala or Thr
VARIANT                 10
                        note = misc_feature - Xaa = Glu or Val
VARIANT                 11
                        note = misc_feature - Xaa = Leu or Val
VARIANT                 12
                        note = misc_feature - Xaa = Ala or Lys
VARIANT                 13
                        note = misc_feature - Xaa = Lys or Arg
VARIANT                 20
                        note = misc_feature - Xaa = Met or Val
VARIANT                 28
                        note = misc_feature - Xaa = Ser or Thr
VARIANT                 31
                        note = misc_feature - Xaa = Glu or Thr
VARIANT                 38
                        note = misc_feature - Xaa = Lys or Arg
VARIANT                 40
                        note = misc_feature - Xaa = Ala or Arg
VARIANT                 58
                        note = misc_feature - Xaa = Ser or Thr
VARIANT                 60
                        note = misc_feature - Xaa = Phe, Leu, Asn or Tyr
VARIANT                 61
                        note = misc_feature - Xaa = Ala or Asn
VARIANT                 65
                        note = misc_feature - Xaa = Lys or Gln
VARIANT                 67
                        note = misc_feature - Xaa = Lys or Arg
VARIANT                 68
                        note = misc_feature - Xaa = Ala or Val
VARIANT                 69
```

```
                        note = misc_feature - Xaa = Lys or Thr
VARIANT                 72
                        note = misc_feature - Xaa = Ala or Arg
VARIANT                 73
                        note = misc_feature - Xaa = Asp or Val
VARIANT                 76
                        note = misc_feature - Xaa = Ala or Thr
VARIANT                 87
                        note = misc_feature - Xaa = Arg or Thr
VARIANT                 88
                        note = misc_feature - Xaa = Asn or Ser
VARIANT                 91
                        note = misc_feature - Xaa = Ser or Thr
VARIANT                 101
                        note = misc_feature - Xaa = Phe or Tyr
VARIANT                 111
                        note = misc_feature - Xaa = Ala or Gln
VARIANT                 114
                        note = misc_feature - Xaa = Met or Thr
source                  1..119
                        mol_type = protein
                        organism = synthetic construct
SEQUENCE: 131
XVQLXQSGXX XXXPGASVKX SCKASGYXFT XYWMHWVXQX PGQGLEWIGT IYPGNSDXSX    60
XQKFXGXXXL TXXTSXSTAY MELSSLXXED XAVYYCTRFY XEDWYFDVWG XGTXVTVSS    119

SEQ ID NO: 132          moltype = AA  length = 106
FEATURE                 Location/Qualifiers
REGION                  1..106
                        note = muPHD48 VL; PHD26/PHD28/PHD29 VL; PHD30 VL;
                        PHD22/PHD24/PHD25 VL; PHD48-01 VL; PHD48-08/PHD48_VL
                        general formula
VARIANT                 1
                        note = misc_feature - Xaa = Asp or Gln
VARIANT                 3
                        note = misc_feature - Xaa = Gln or Val
VARIANT                 4
                        note = misc_feature - Xaa = Leu or Met
VARIANT                 9
                        note = misc_feature - Xaa = Ala or Ser
VARIANT                 10
                        note = misc_feature - Xaa = Ile or Ser
VARIANT                 11
                        note = misc_feature - Xaa = Leu or Met
VARIANT                 15
                        note = misc_feature - Xaa = Pro or Val
VARIANT                 17
                        note = misc_feature - Xaa = Asp or Glu
VARIANT                 18
                        note = misc_feature - Xaa = Lys or Arg
VARIANT                 22
                        note = misc_feature - Xaa = Ser or Thr
VARIANT                 24
                        note = misc_feature - Xaa = Arg or Ser
VARIANT                 29
                        note = misc_feature - Xaa = Ile or Val
VARIANT                 31
                        note = misc_feature - Xaa = Trp or Tyr
VARIANT                 32
                        note = misc_feature - Xaa = Leu or Met
VARIANT                 41
                        note = misc_feature- Xaa = Lys or Ser
VARIANT                 42
                        note = misc_feature - Xaa = Ala or Ser
VARIANT                 46
                        note = misc_feature - Xaa = Lue or Trp
VARIANT                 49
                        note = misc_feature - Xaa = Arg or Tyr
VARIANT                 52
                        note = misc_feature - Xaa = Asn, Ser or Thr
VARIANT                 54
                        note = misc_feature - Xaa = Ala or Gly
VARIANT                 59
                        note = misc_feature - Xaa = Ala or Ser
VARIANT                 69
                        note = misc_feature - Xaa = Asp or Ser
VARIANT                 71
                        note = misc_feature - Xaa = Ser or Thr
VARIANT                 77
```

-continued

```
                         note = misc_feature - Xaa = Leu or Met
VARIANT                  78
                         note = misc_feature - Xaa = Glu or Gln
VARIANT                  79
                         note = misc_feature - Xaa = Ala or Pro
VARIANT                  82
                         note = misc_feature - Xaa = Ala or Phe
VARIANT                  90
                         note = misc_feature - Xaa = Trp or Tyr
VARIANT                  103
                         note = misc_feature - Xaa = Leu or Val
source                   1..106
                         mol_type = protein
                         organism = synthetic construct
SEQUENCE: 132
XIXXTQSPXX XSASXGXXVT IXCXASSSXS XXYWFQQKPG XXPKPXIYXT SXLXSGVPXR  60
FSGSGSGTXY XLTISSXXXE DXATYYCQQX HSYPPTFGGG TKXEIK                 106

SEQ ID NO: 133           moltype = AA  length = 119
FEATURE                  Location/Qualifiers
REGION                   1..119
                         note = muPHD49 VH; PHD49-01 VH; PHD49-05_VH; PHD49-11_VH;
                          PHD49-21/PHD49_VH general formula
VARIANT                  5
                         note = misc_feature - Xaa = Gln or Val
VARIANT                  11
                         note = misc_feature - Xaa = Leu or Val
VARIANT                  12
                         note = misc_feature - Xaa = Ala or Lys
VARIANT                  13
                         note = misc_feature - Xaa = Lys or Arg
VARIANT                  16
                         note = misc_feature - Xaa = Ala or Ser
VARIANT                  20
                         note = misc_feature - Xaa = Leu or Val
VARIANT                  27
                         note = misc_feature - Xaa = Phe or Tyr
VARIANT                  32
                         note = misc_feature - Xaa = His or Tyr
VARIANT                  34
                         note = misc_feature - Xaa = Ile or Met
VARIANT                  38
                         note = misc_feature - Xaa = Lys or Arg
VARIANT                  40
                         note = misc_feature - Xaa = Ala or Arg
VARIANT                  53
                         note = misc_feature - Xaa = Pro or Thr
VARIANT                  56
                         note = misc_feature - Xaa = Asp or Gly
VARIANT                  65
                         note = misc_feature - Xaa = Lys or Gln
VARIANT                  67
                         note = misc_feature - Xaa = Lys or Arg
VARIANT                  70
                         note = misc_feature - Xaa = Ile or Leu
VARIANT                  72
                         note = misc_feature - Xaa = Ala or Thr
VARIANT                  74
                         note = misc_feature - Xaa = Glu or Lys
VARIANT                  76
                         note = misc_feature - Xaa = Ser or Thr
VARIANT                  82
                         note = misc_feature - Xaa = Glu or Gln
VARIANT                  87
                         note = misc_feature - Xaa = Ala or Arg
VARIANT                  91
                         note = misc_feature - Xaa = Ser or Thr
VARIANT                  101
                         note = misc_feature - Xaa = Asp or His
VARIANT                  107
                         note = misc_feature - Xaa = Ala or Asp
VARIANT                  119
                         note = misc_feature - Xaa = Ala or Ser
source                   1..119
                         mol_type = protein
                         organism = synthetic construct
SEQUENCE: 133
QVQLXQSGAE XXXPGXSVKX SCKASGXTFS SXWXQWVXQX PGQGLEWIGA IYXGDXDTIY  60
TQKFXGXATX TXDXSXSTAY MXLSSLXSED XAVYYCARNY XYQAWFXYWG QGTLVTVSX   119
```

```
SEQ ID NO: 134         moltype = AA  length = 106
FEATURE                Location/Qualifiers
REGION                 1..106
                       note = muPHD49 VL; PHD49-01 VL; PHD49-05/PHD49_VL;
                        PHD49-11_VL; PHD49-21_VL general formula
VARIANT                1
                       note = misc_feature - Xaa = Asp or Gln
VARIANT                3
                       note = misc_feature - Xaa = Gln or Val
VARIANT                4
                       note = misc_feature - Xaa = Leu or Met
VAR_SEQ                9
                       note = misc_feature - Xaa = Ala or Ser
VARIANT                10
                       note = misc_feature - Xaa = Leu or Ser
VARIANT                11
                       note = misc_feature - Xaa = Leu or Met
VARIANT                15
                       note = misc_feature - Xaa = Pro or Val
VARIANT                17
                       note = misc_feature - Xaa = Asp or Glu
VARIANT                18
                       note = misc_feature - Xaa =Lys or Arg
VARIANT                21
                       note = misc_feature - Xaa = Ile or Met
VARIANT                24
                       note = misc_feature - Xaa = Arg or Ser
VARIANT                32
                       note = misc_feature - Xaa = Leu or Met
VARIANT                40
                       note = misc_feature - Xaa = Gly or Arg
VARIANT                41
                       note = misc_feature - Xaa = Lys or Ser
VARIANT                42
                       note = misc_feature - Xaa = Ala or Ser
VARIANT                46
                       note = misc_feature - Xaa = Leu or Trp
VARIANT                52
                       note = misc_feature - Xaa = Asp, Asn or Ser
VARIANT                59
                       note = misc_feature - Xaa = Ala or Ser
VARIANT                69
                       note = misc_feature - Xaa = Asp or Ser
VARIANT                71
                       note = misc_feature - Xaa = Ser or Thr
VARIANT                77
                       note = misc_feature - Xaa = Leu or Met
VARIANT                78
                       note = misc_feature - Xaa = Glu or Gln
VARIANT                79
                       note = misc_feature - Xaa = Ala or Pro
VARIANT                82
                       note = misc_feature - Xaa = Ala or Phe
VARIANT                99
                       note = misc_feature - Xaa = Ala or Gln
VARIANT                105
                       note = misc_feature - Xaa = Ile or Leu
source                 1..106
                       mol_type = protein
                       organism = synthetic construct
SEQUENCE: 134
XIXXTQSPXX XSASXGXXVT XTCXASSSVS YXYWYQQKPX XXPKPXIYLT SXLASGVPXR   60
FSGSGSGTXY XLTISSXXXE DXATYYCQQW SSNPLTFGXG TKLEXK                 106
```

TrkA ANTIBODY AND APPLICATION THEREOF

REFERENCE TO SEQUENCE LISTING

In accordance with 37 CFR § 1.52(e)(5) and with 37 CFR § 1.831, the specification makes reference to a Sequence Listing submitted electronically as a .xml file named "548003US_ST26_XMLL_corrected.xml". The .xml file was generated on Sep. 20, 2023 and is 220,464 bytes in size. The entire contents of the Sequence Listing are hereby incorporated by reference.

BACKGROUND OF THE INVENTION

This application is a National Stage Application and claims priority under 35 U.S.C. § 371 to Patent Cooperation Treaty application PCT/CN2022/142180, filed Dec. 27, 2022, which claims the benefit of Patent Cooperation Treaty application PCT/CN2021/142017, filed Dec. 28, 2021. Priority is claimed to these applications and the disclosures of these prior applications are considered part of the disclosure of this application and to the extent allowed the entire contents of the aforementioned applications are incorporated herein.

Neurotrophins are a family of peptide growth factors, structurally related to the first member of the family, NGF (Nerve Growth Factor). Neurotrophins modulate neuronal differentiation and survival, as well the synaptic transmission, both of peripheral neurons and of the central nervous system. Furthermore, NGF acts on various non-neuronal tissues and cells, as immune system cells.

NGF acts through two membrane receptors present in the target cells, the low affinity p75 receptor, and the 140 kDa high affinity transmembrane glycoprotein TrkA (Tropomyosin receptor kinase A) having a tyrosine kinase activity. TrkA is expressed in neural-crest neurons, in sympathetic neurons as well as in cholinergic neurons of the basal forebrain and corpus striatum, where it represents the crucial mediator of NGF activities. TrkA is also expressed in some non-neuronal tissues and cells, including B lymphocytes.

Studies showed a direct relationship between pain and the TrkA system, demonstrating, in four unrelated cases of type 4 pain chronic insensitivity, the presence of mutations of the TrkA gene and consequently the absence of functional NGF receptors. Accordingly, the NGF-TrkA system provides a potential target to design therapies against pain, i.e. treatments able to antagonize the pain associated neuropathic syndrome via TrkA-effective antagonists.

The reported anti-TrkA antibodies often block the binding between NGF and TrkA, which could lead to undesired side effects.

Accordingly, it is highly needed to develop TrkA antagonists that do not result in such side effects while being therapeutically effective.

SUMMARY OF THE INVENTION

The present disclosure provides a TrkA antibody and use thereof. Particularly, the present disclosure provides anti-TrkA antibodies, compositions comprising such antibodies, and methods of using such antibodies for the treatment of pain, such as chronic pain of nociceptive, non-nociceptive, inflammatory, traumatic, neuropathic, nociplastic, or mixed etiologies.

In one aspect, the present disclosure provides an antibody or an antigen binding fragment thereof, which is capable of specifically binding to TrkA and exhibits one or more properties selected from the group consisting of: being capable of binding to TrkA with a $K_D$ of less than about $5*10^{-8}$ M, as measured by Octet or by SPR; being capable of inhibiting the activation of TrkA induced by NGF; does not substantially block the binding between TrkA and NGF; does not substantially compete with NGF for binding to TrkA; and being capable of mitigating NGF mediated pain sensitization. In particular, the antibody or an antigen binding fragment thereof of the present disclosure could mitigate NGF mediated pain sensitization without substantially compromise NGF's effect on neuronal growth and survival, i.e., it could selectively mitigate NGF mediated pain sensitization.

In some embodiments, the antibody or the antigen binding fragment thereof is capable of recognizing an epitope of TrkA extracellular domain (ECD), the epitope comprises amino acid residues Q176, H178, G179, Q180, and P187 of SEQ ID NO: 119.

In some embodiments, the antibody or the antigen binding fragment thereof is capable of specifically binding to Q176, H178, G179, Q180 and/or P187 of SEQ ID NO: 119.

In some embodiments, the antibody is selected from the group consisting of: a monoclonal antibody, a chimeric antibody, a humanized antibody, a fully human antibody and a multi-specific antibody (such as a bispecific antibody, or a tri-specific antibody).

In some embodiments, the antigen binding fragment is selected from the group consisting of: a Fab fragment, a Fab' fragment, a F(ab)$_2$ fragment, a Fv fragment, a VHH and an ScFv.

In some embodiments, the TrkA is human TrkA.

In some embodiments, the antibody or the antigen binding fragment thereof is capable of competing with a reference antibody for binding to the TrkA, wherein the reference antibody comprises light chain CDR1-3 and heavy chain CDR1-3, the light chain CDR1-3 comprises the amino acid sequence as set forth in SEQ ID NOs: 96-98 respectively, and the heavy chain CDR1-3 comprises the amino acid sequence as set forth in SEQ ID NOs: 93-95 respectively.

In some embodiments, the antibody or the antigen binding fragment thereof comprises at least one of light chain CDRs 1-3 of a light chain variable region, and the light chain variable region comprises an amino acid sequence as set forth in any one of SEQ ID NOs: 132, 134, 15, and 53.

In some embodiments, the antibody or the antigen binding fragment thereof comprises at least one of heavy chain CDRs 1-3 of a heavy chain variable region, and the heavy chain variable region comprises an amino acid sequence as set forth in any one of SEQ ID NOs: 131, 133, 14 and 51.

In some embodiments, the antibody or the antigen binding fragment thereof comprises a light chain CDR1, and the light chain CDR1 comprises an amino acid sequence as set forth in any one of SEQ ID NOs: 96, 117, 9, and 50.

In some embodiments, the antibody or the antigen binding fragment thereof comprises a light chain CDR1, and the light chain CDR1 comprises an amino acid sequence as set forth in any one of SEQ ID NOs: 9, 28, 50, 56, 80, and 88.

In some embodiments, the antibody or the antigen binding fragment thereof comprises a light chain CDR2, and the light chain CDR2 comprises an amino acid sequence as set forth in any one of SEQ ID NOs: 97, 118, and 11.

In some embodiments, the antibody or the antigen binding fragment thereof comprises a light chain CDR2, and the light chain CDR2 comprises an amino acid sequence as set forth in any one of SEQ ID NOs: 11, 30, 39, 58, 77, 82, 103, and 108.

In some embodiments, the antibody or the antigen binding fragment thereof comprises a light chain CDR3, and the light chain CDR3 comprises an amino acid sequence as set forth in any one of SEQ ID NOs: 98, 13, and 41.

In some embodiments, the antibody or the antigen binding fragment thereof comprises a light chain CDR3, and the light chain CDR3 comprises an amino acid sequence as set forth in any one of SEQ ID NOs: 13, 32, 41, 60.

In some embodiments, the antibody or the antigen binding fragment thereof comprises a light chain variable region, and the light chain variable region comprises an amino acid sequence as set forth in any one of SEQ ID NOs: 132, 134, 15, and 53.

In some embodiments, the antibody or the antigen binding fragment thereof comprises a light chain variable region, and the light chain variable region comprises an amino acid sequence as set forth in any one of SEQ ID NOs: 15, 18, 44, 53, 61, 78, 85, 90, 91, 100, 104, 107, and 113.

In some embodiments, the antibody or the antigen binding fragment thereof comprises a light chain constant region, and the light chain constant region comprises a human Igκ constant region or a human Igλ constant region.

In some embodiments, the antibody or the antigen binding fragment thereof comprises a heavy chain CDR1, and the heavy chain CDR1 comprises an amino acid sequence as set forth in any one of SEQ ID NOs: 93, 114 ($SX_1WX_2Q$, wherein $X_1$ is H or Y, $X_2$ is I or M), 1, and 47.

In some embodiments, the antibody or the antigen binding fragment thereof comprises a heavy chain CDR1, and the heavy chain CDR1 comprises an amino acid sequence as set forth in any one of SEQ ID NOs: 1, 20, 45, 47, 62, 101, and 109.

In some embodiments, the antibody or the antigen binding fragment thereof comprises a heavy chain CDR2, and the heavy chain CDR2 comprises an amino acid sequence as set forth in any one of SEQ ID NOs: 94, 115, 4, and 48.

In some embodiments, the antibody or the antigen binding fragment thereof comprises a heavy chain CDR2, and the heavy chain CDR2 comprises an amino acid sequence as set forth in any one of SEQ ID NOs: 4, 23, 46, 48, 65, 73, 75, 87, 102, and 110.

In some embodiments, the antibody or the antigen binding fragment thereof comprises a heavy chain CDR3, and the heavy chain CDR3 comprises an amino acid sequence as set forth in any one of SEQ ID NOs: 95, 116, 7, and 49.

In some embodiments, the antibody or the antigen binding fragment thereof comprises a heavy chain CDR3, and the heavy chain CDR3 comprises an amino acid sequence as set forth in any one of SEQ ID NOs: 7, 26, 37, 49, 68, and 111.

In some embodiments, the antibody or the antigen binding fragment thereof comprises a heavy chain variable region, and the heavy chain variable region comprises an amino acid sequence as set forth in any one of SEQ ID NOs: 131, 133, 14, and 51.

In some embodiments, the antibody or the antigen binding fragment thereof comprises a heavy chain variable region, and the heavy chain variable region comprises an amino acid sequence as set forth in any one of SEQ ID NOs: 14, 16, 42, 51, 70, 74, 76, 84, 86, 89, 92, 99, 105, 106, and 112.

In some embodiments, the antibody or the antigen binding fragment thereof comprises a heavy chain constant region, and the heavy chain constant region comprises a human IgG constant region.

In some embodiments, the antibody or the antigen binding fragment thereof comprises: 1) light chain CDR1-3 comprising the amino acid sequence as set forth in SEQ ID NOs: 96, 97, and 98 respectively, and heavy chain CDR1-3 comprising the amino acid sequence as set forth in SEQ ID NOs: 93, 94, and 95 respectively; 2) light chain CDR1-3 comprising the amino acid sequence as set forth in SEQ ID NOs: 117, 118, and 41 respectively, and heavy chain CDR1-3 comprising the amino acid sequence as set forth in SEQ ID NOs: 114 ($SX_1WX_2Q$, wherein $X_1$ is H or Y, $X_2$ is I or M), 115, and 116 respectively; 3) light chain CDR1-3 comprising the amino acid sequence as set forth in SEQ ID NOs: 9, 11, and 13 respectively, and heavy chain CDR1-3 comprising the amino acid sequence as set forth in SEQ ID NOs: 1, 4, and 7 respectively; 4) light chain CDR1-3 comprising the amino acid sequence as set forth in SEQ ID NOs: 28, 30, and 32 respectively, and heavy chain CDR1-3 comprising the amino acid sequence as set forth in SEQ ID NOs: 20, 23, and 26 respectively; 5) light chain CDR1-3 comprising the amino acid sequence as set forth in SEQ ID NOs: 56, 58, and 60 respectively, and heavy chain CDR1-3 comprising the amino acid sequence as set forth in SEQ ID NOs: 62, 65, and 68 respectively; 6) light chain CDR1-3 comprising the amino acid sequence as set forth in SEQ ID NOs: 56, 58, and 60 respectively, and heavy chain CDR1-3 comprising the amino acid sequence as set forth in SEQ ID NOs: 20, 73, and 68 respectively; 7) light chain CDR1-3 comprising the amino acid sequence as set forth in SEQ ID NOs: 56, 58, and 60 respectively, and heavy chain CDR1-3 comprising the amino acid sequence as set forth in SEQ ID NOs: 20, 75, and 68 respectively; 8) light chain CDR1-3 comprising the amino acid sequence as set forth in SEQ ID NOs: 56, 77, and 60 respectively, and heavy chain CDR1-3 comprising the amino acid sequence as set forth in SEQ ID NOs: 62, 65, and 68 respectively; 9) light chain CDR1-3 comprising the amino acid sequence as set forth in SEQ ID NOs: 56, 77, and 60 respectively, and heavy chain CDR1-3 comprising the amino acid sequence as set forth in SEQ ID NOs: 20, 73, and 68 respectively; 10) light chain CDR1-3 comprising the amino acid sequence as set forth in SEQ ID NOs: 56, 77, and 60 respectively, and heavy chain CDR1-3 comprising the amino acid sequence as set forth in SEQ ID NOs: 20, 75, and 68 respectively; 11) light chain CDR1-3 comprising the amino acid sequence as set forth in SEQ ID NOs: 80, 82, and 32 respectively, and heavy chain CDR1-3 comprising the amino acid sequence as set forth in SEQ ID NOs: 62, 79 and 26 respectively; 12) light chain CDR1-3 comprising the amino acid sequence as set forth in SEQ ID NOs: 88, 30, and 32 respectively, and heavy chain CDR1-3 comprising the amino acid sequence as set forth in SEQ ID NOs: 20, 87, and 26 respectively; 13) light chain CDR1-3 comprising the amino acid sequence as set forth in SEQ ID NOs: 28, 39, and 41 respectively, and heavy chain CDR1-3 comprising the amino acid sequence as set forth in SEQ ID NOs: 45, 46, and 37 respectively; 14) light chain CDR1-3 comprising the amino acid sequence as set forth in SEQ ID NOs: 88, 103, and 41 respectively, and heavy chain CDR1-3 comprising the amino acid sequence as set forth in SEQ ID NOs: 101, 102, and 37 respectively; 15) light chain CDR1-3 comprising the amino acid sequence as set forth in SEQ ID NOs: 88, 103, and 41 respectively, and heavy chain CDR1-3 comprising the amino acid sequence as set forth in SEQ ID NOs: 109, 110, and 111 respectively; 16) light chain CDR1-3 comprising the amino acid sequence as set forth in SEQ ID NOs: 88, 39, and 41 respectively, and heavy chain CDR1-3 comprising the amino acid sequence as set forth in SEQ ID NOs: 45, 46, and 37 respectively; 17) light chain CDR1-3 comprising the amino acid sequence as set forth in SEQ ID NOs: 39, 108 and 41 respectively, and heavy chain CDR1-3 comprising the amino acid sequence as set forth in SEQ ID NOs: 109, 110, and 111 respectively; or 18) light chain CDR1-3 comprising the amino acid sequence as set forth in SEQ ID NOs: 50, 39, and 41 respectively, and heavy chain CDR1-3 comprising the amino acid sequence as set forth in SEQ ID NOs: 47, 48, and 49 respectively.

In some embodiments, the antibody or the antigen binding fragment thereof comprises: 1) a light chain variable region comprising the amino acid sequence as set forth in SEQ ID NO: 132, and a heavy chain variable region comprising the amino acid sequence as set forth in SEQ ID NO: 131; 2) a light chain variable region comprising the amino acid sequence as set forth in SEQ ID NO: 134, and a heavy chain variable region comprising the amino acid sequence as set forth in SEQ ID NO: 133; 3) a light chain variable region comprising the amino acid sequence as set forth in SEQ ID NO: 15, and a heavy chain variable region comprising the amino acid sequence as set forth in SEQ ID NO: 14; 4) a light chain variable region comprising the amino acid sequence as set forth in SEQ ID NO: 18, and a heavy chain variable region comprising the amino acid sequence as set forth in SEQ ID NO: 16; 5) a light chain variable region comprising the amino acid sequence as set forth in SEQ ID NO: 90, and a heavy chain variable region comprising the amino acid sequence as set forth in SEQ ID NO: 89; 6) a light chain variable region comprising the amino acid sequence as set forth in SEQ ID NO: 91, and a heavy chain variable region comprising the amino acid sequence as set forth in SEQ ID NO: 86; 7) a light chain variable region comprising the amino acid sequence as set forth in SEQ ID NO: 91, and a heavy chain variable region comprising the amino acid sequence as set forth in SEQ ID NO: 92; 8) a light chain variable region comprising the amino acid sequence as set forth in SEQ ID NO: 61, and a heavy chain variable region comprising the amino acid sequence as set forth in SEQ ID NO: 70; 9) a light chain variable region comprising the amino acid sequence as set forth in SEQ ID NO: 61, and a heavy chain variable region comprising the amino acid sequence as set forth in SEQ ID NO: 74; 10) a light chain variable region comprising the amino acid sequence as set forth in SEQ ID NO: 61, and a heavy chain variable region comprising the amino acid sequence as set forth in SEQ ID NO: 76; 11) a light chain variable region comprising the amino acid sequence as set forth in SEQ ID NO: 78, and a heavy chain variable region comprising the amino acid sequence as set forth in SEQ ID NO: 70; 12) a light chain variable region comprising the amino acid sequence as set forth in SEQ ID NO: 78, and a heavy chain variable region comprising the amino acid sequence as set forth in SEQ ID NO: 74; 13) a light chain variable region comprising the amino acid sequence as set forth in SEQ ID NO: 78, and a heavy chain variable region comprising the amino acid sequence as set forth in SEQ ID NO: 76; 14) a light chain variable region comprising the amino acid sequence as set forth in SEQ ID NO: 85, and a heavy chain variable region comprising the amino acid sequence as set forth in SEQ ID NO: 84; 15) a light chain variable region comprising the amino acid sequence as set forth in SEQ ID NO: 44, and a heavy chain variable region comprising the amino acid sequence as set forth in SEQ ID NO: 42; 16) a light chain variable region comprising the amino acid sequence as set forth in SEQ ID NO: 100, and a heavy chain variable region comprising the amino acid sequence as set forth in SEQ ID NO: 99; 17) a light chain variable region comprising the amino acid sequence as set forth in SEQ ID NO: 104, and a heavy chain variable region comprising the amino acid sequence as set forth in SEQ ID NO: 105; 18) a light chain variable region comprising the amino acid sequence as set forth in SEQ ID NO: 104, and a heavy chain variable region comprising the amino acid sequence as set forth in SEQ ID NO: 112; 19) a light chain variable region comprising the amino acid sequence as set forth in SEQ ID NO: 107, and a heavy chain variable region comprising the amino acid sequence as set forth in SEQ ID NO: 106; 20) a light chain variable region comprising the amino acid sequence as set forth in SEQ ID NO: 113, and a heavy chain variable region comprising the amino acid sequence as set forth in SEQ ID NO: 112 or 21) a light chain variable region comprising the amino acid sequence as set forth in SEQ ID NO: 53, and a heavy chain variable region comprising the amino acid sequence as set forth in SEQ ID NO: 51.

In another aspect, the present disclosure provides a fusion protein comprising the antibody or the antigen binding fragment of the present disclosure.

In another aspect, the present disclosure provides a protein conjugate, comprising the antibody or the antigen binding fragment of the present disclosure, or the fusion protein of the present disclosure.

In another aspect, the present disclosure provides one or more isolated nucleic acid molecule or molecules, encoding for the antibody or the antigen binding fragment of the present disclosure, or the fusion protein of the present disclosure.

In another aspect, the present disclosure provides one or more vector or vectors, comprising the one or more isolated nucleic acid molecule or molecules of the present disclosure.

In another aspect, the present disclosure provides a cell, comprising the isolated nucleic acid molecule or molecules or the vector or vectors of the present disclosure.

In another aspect, the present disclosure provides a composition, comprising the antibody or the antigen binding fragment, the fusion protein, the protein conjugate, the isolated nucleic acid molecule or molecules, the vector or vectors, and/or the cell of the present disclosure, and optionally a pharmaceutically acceptable excipient.

In some embodiments, the pharmaceutically acceptable excipient in the composition comprises a buffer.

In some embodiments, the pH of the composition is about 1-13.

In another aspect, the present disclosure provides use of the antibody or the antigen binding fragment thereof, the fusion protein, the protein conjugate, the isolated nucleic acid molecule or molecules, the vector or vectors, the cell, and/or the composition of the present disclosure in the manufacture of a medicament for preventing and/or treating a disease or disorder associated with an inappropriate expression or function of TrkA.

In some embodiments, the disease or disorder comprises pain.

In some embodiments, the pain comprises chronic pain.

In some embodiments, the disease or disorder comprises chronic pain of nociceptive, inflammatory, neuropathic, proliferative or mixed etiology.

In some embodiments, the disease or disorder comprises chronic pain of musculoskeletal or neuropathic origin.

In some embodiments, the disease or disorder comprises post-operative pain, rheumatoid arthritis pain, neuropathic pain and/or osteoarthritis pain.

In another aspect, the present disclosure provides use of the antibody or the antigen binding fragment thereof, the fusion protein, or the protein conjugate in the manufacture of an agent for determining the presence and/or amount of TrkA in a sample.

In another aspect, the present disclosure provides a method for producing the antibody or the antigen binding fragment thereof, or the fusion protein of the present disclosure, comprising culturing the cell of the present disclosure under conditions enabling expression of the antibody or the antigen binding fragment, or the fusion protein.

In another aspect, the present disclosure provides a method for preventing and/or treating a disease or disorder in a subject in need thereof, comprising administering to the subject an effective amount of the antibody or the antigen binding fragment the fusion protein, the protein conjugate, the isolated nucleic acid molecule or molecules, the vector or vectors, the cell, and/or the composition of the present disclosure, wherein the disease or disorder is a disease or disorder associated with an inappropriate expression or function of TrkA.

In some embodiments of the method, the disease or disorder comprises pain.

In some embodiments of the method, the pain comprises chronic pain.

In some embodiments of the method, the disease or disorder comprises chronic pain of nociceptive, inflammatory, neuropathic, proliferative or mixed etiology.

In some embodiments of the method, the disease or disorder comprises chronic pain of musculoskeletal or neuropathic origin.

In some embodiments of the method, the disease or disorder comprises post-operative pain, rheumatoid arthritis pain, neuropathic pain and/or osteoarthritis pain.

In another aspect, the present disclosure provides a method for determining the presence and/or amount of TrkA in a sample, comprising: a) contacting the sample with the antibody or the antigen binding fragment, the fusion protein, or the protein conjugate of the present disclosure; and b) determining the presence and/or amount of the antibody or the antigen binding fragment, of the fusion protein, or of the protein conjugate bound to the sample.

In another aspect, the present disclosure provides the antibody or the antigen binding fragment thereof, the fusion protein, the protein conjugate, the isolated nucleic acid molecule or molecules, the vector or vectors, the cell, or the composition of the present disclosure, for: a) preventing and/or treating a disease or disorder, and/or b) determining the presence and/or amount of TrkA in a sample, wherein the disease or disorder is a disease or disorder associated with an inappropriate expression or function of TrkA.

In another aspect, the present disclosure provides a method for screening for or obtaining a TrkA antibody which does not substantially block the binding between TrkA and NGF, comprising using an epitope of TrkA extracellular domain (ECD) comprising amino acid residues: Q176, H178, G179, Q180, and P187 of SEQ ID NO: 119

In some embodiments of the method, the TrkA antibody exhibits one or more properties selected from the group consisting of: is capable of binding to TrkA with a KD of less than about $5*10^{-8}$ M, as measured by Octet or SPR; is capable of inhibiting the activation of TrkA induced by NGF; does not substantially compete with NGF for binding to TrkA; and is capable of mitigating pain sensitization, such as NGF mediated pain sensitization, e.g., is capable of selectively mitigating NGF mediated pain sensitization without substantially compromising NGF's effect on neuronal growth and survival.

In some embodiments, the method is an in vitro or ex vivo method.

In another aspect, the present disclosure provides use of an epitope of TrkA extracellular domain (ECD) in the manufacture of an agent for obtaining or screening for a TrkA antibody which does not substantially block the binding between TrkA and NGF, wherein the epitope comprises amino acid residues: Q176, H178, G179, Q180, and P187 of SEQ ID NO: 119.

In some embodiments of the use, the TrkA antibody exhibits one or more properties selected from the group consisting of: is capable of binding to TrkA with a KD of less than about $5*10-8$ M, as measured by Octet or SPR; is capable of inhibiting the activation of TrkA induced by NGF; does not substantially compete with NGF for binding to TrkA; and is capable of mitigating pain sensitization, such as NGF mediated pain sensitization, e.g., is capable of selectively mitigating NGF mediated pain sensitization without substantially compromising NGF's effect on neuronal growth and survival.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present application will be obtained by reference to the following detailed description that sets forth illustrative embodiments, in which the principles of the invention are employed, and the accompanying drawings (also "figure" and "FIG." herein), of which:

FIG. 8A-8J demonstrate that the antibodies of the present disclosure do not block the binding between TrkA and NGF.

DETAILED DESCRIPTION

Figure 1:
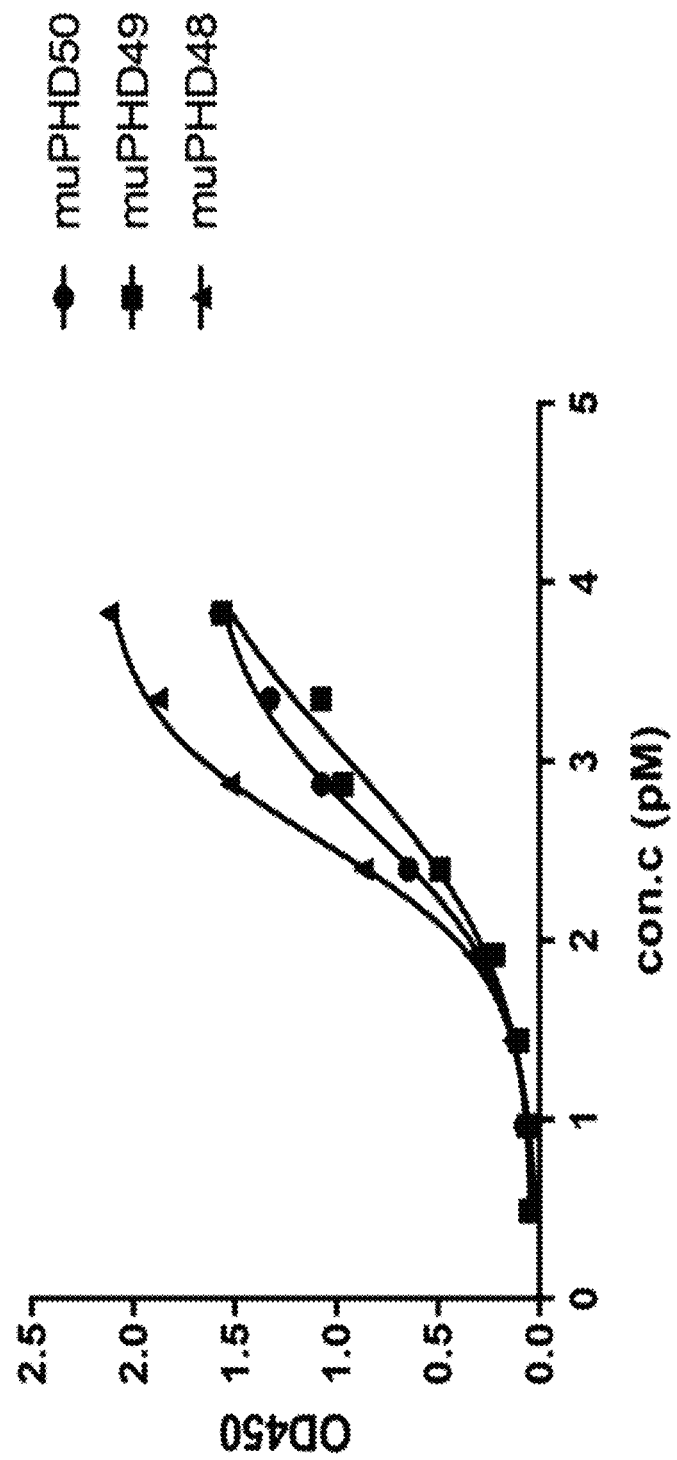
FIG. 1 illustrates the results of ELISA binding analysis of exemplary antibodies of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "antibody", as used herein, generally refers to an immunoglobulin or an immunoglobulin-like molecule capable of specifically recognizing or binding to an antigen. An antibody may comprise a light chain (L) and a heavy chain (H). The light chains of an antibody can be classified as κ and λ light chains. The heavy chains can be classified as μ, δ, γ, α or ε, and the isotypes of an antibody are defined as IgM, IgD, IgG (e.g., IgG1, IgG2, IgG3 or IgG4 subtype), IgA and IgE, respectively. Each heavy chain may comprise a heavy chain variable region (VH) and a heavy chain constant region (CH). The heavy chain constant region may comprise three domains (CH1, CH2 and CH3). Each light chain may comprise a light chain variable region (VL) and a light chain constant region (CL). The light chain constant region may comprise a CL domain. The VH and VL regions can also be subdivided into regions with high variability known as complementarity determining regions (CDRs) interspersed with more conserved regions known as framework regions (FRs). Each VH and VL consists of 3 CDRs and 4 FRs arranged from N-terminal to C-terminal in the following order: FR1, CDR1, FR2, CDR2, FR3, CDR3, FR4. The variable regions (VH and VL) of each heavy/light chain pair form the antibody binding site, respectively. Distribution of amino acids to regions or domains follows the definition of Kabat Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883. The term "antibody" is not limited by any antibody-producing method. For example, it includes recombinant antibodies, monoclonal antibodies, and other forms of antibodies. In some cases, an antibody of the present disclosure is an isolated antibody.

The term "antigen binding fragment", as used herein, generally refers to one or more fragments of a full-length antibody that retain the ability to bind the same antigen to which the antibody binds (e.g., TrkA) and/or competes against an intact antibody for an antigen-specific binding. Antigen binding fragment can be produced by recombinant DNA techniques or by enzymatic or chemical cleavage of intact antibodies. In some cases, the antigen binding fragment includes Fab, Fab', F (ab')$_2$, F(ab)$_2$, VHH, Fd, Fv, dAb and complementarity determining region (CDR) fragments, single chain antibodies (e.g., ScFv), chimeric antibodies, diabodies, and polypeptides that comprise at least a portion of an antibody that is sufficient to confer specific antigen-binding ability to the polypeptide.

The term "TrkA", as used herein, generally refers to high affinity nerve growth factor receptor or neurotrophic tyrosine kinase receptor type 1 or TRK1-transforming tyrosine kinase protein or Tropomyosin-related kinase A or Tyrosine kinase receptor or Tyrosine kinase receptor A or Trk-A or gp140trk or p140-TrkA or MTC or TRK. TrkA is a receptor tyrosine kinase involved in the development and the maturation of the central and peripheral nervous systems through regulation of proliferation, differentiation, and survival of sympathetic and nervous neurons. TrkA is the high affinity receptor for NGF which is its primary ligand; it may also bind and be activated by NTF3/neurotrophin-3. TrkA as used herein may comprise functional fragments, variants, isoforms, and species homologs of human TrkA. Accordingly, antibodies of this disclosure may, in certain cases, cross-react with TrkA from species other than human. In certain embodiments, the antibodies may be completely specific for one or more human TrkA proteins and may not exhibit species or other types of non-human cross-reactivity. The complete amino acid sequence of the four known human TrkA isoforms are found under the UniProt/Swiss-Prot accession number P04629 (Consortium TU, (2012) Nucleic Acids Res. 40(D1):D71-D5). The four isoforms are produced by alternative splicing: isoform TrkA-I is found in most non-neuronal tissues (UniProt/Swiss-Prot accession number P04629-2), while isoform TrkA-II is primarily expressed in neuronal cells (UniProt/Swiss-Prot accession number P04629-1), and isoform TrkA-III is specifically expressed by pluripotent neural stem and neural crest progenitors (UniProt/Swiss-Prot accession number P04629-4). A fourth isoform which differs from isoform TrkA-II at residues 1-71 and lacks residues 393 to 398 is known as isoform 3 (UniProt/Swiss-Prot accession number P04629-3). TrkA-II isoform is the major known isoform of TrkA. Isoform TrkA-I has enhanced responsiveness to NTF3 neurotrophin whereas isoform TrkA-III is constitutively active and does not bind NGF.

The term "biological activities of TrkA" or "TrkA biological activities", as used herein, generally refers to any one or more of the following: the ability to bind NGF or other neurotrophins; the ability to activate an NGF induced signaling pathway; the ability to promote cell differentiation, proliferation, survival, growth, migration and other changes in cell physiology, including (in the case of neurons, including peripheral and central neuron) change in neuronal morphology, synaptogenesis, synaptic function, neurotransmitter and/or neuropeptide release and regeneration following damage; and the ability to mediate pain and cancer pain associated with bone metastasis.

The term "TrkA/NGF signaling pathway", as used herein, generally refers to the signaling pathway relating to Nerve Growth Factor (NGF) and Tyrosine Kinase A (TrkA). The NGF peptides may engage the NGF pathway through TrkA phosphorylation, and activation of ShcC/PI3K and Plc-7/MAPK signaling, promoting AKT-dependent survival and CREB-driven neuronal activity. The TrkA/NGF signaling pathway may promote survival and innervation of sympathetic and sensory neurons, for example, may relate to the endocytosis and retrograde transport of NGF/TrkA-containing endosomes from the axon terminal to the cell body for activation of NGF-inducible gene expression responsible for neuronal survival and development.

The term "binding specificity", as used herein, generally refers to an ability of one substance to bind another substance specifically, and not substantially bind to any other substance at random. For example, one protein may bind to another protein specifically due to their specific structures. Binding specificity may be measured by, e.g., cross-competing assays or other binding assays known in the art.

The term "$K_D$", as used herein, generally refers to the dissociation constant, a specific type of equilibrium constant that measures the propensity of a larger object to separate (dissociate) reversibly into smaller components, as when a complex falls apart into its component molecules. The dissociation constant is the inverse of the association constant. In the specific case of antibodies (Ab) binding to antigen (Ag), usually the term affinity constant refers to the association constant.

The term "$K_{on}$", as used herein, generally refers to on rate constant for association of a binding protein (e.g., an antibody or an antigen binding fragment thereof) to the antigen to form a bound complex (e.g., an antibody/antigen complex). The term "$K_{on}$" also means "association rate constant", or "ka", as is used interchangeably herein. This value indicates the binding rate of a binding protein to its target antigen or the rate of complex formation between a binding protein, (e.g., an antibody) and the corresponding antigen.

The term "$IC_{50}$", as used herein, generally refers to the half maximal inhibitory concentration ($IC_{50}$) which is a measure of the effectiveness of a compound in inhibiting a biological function, e.g. the ability of a TrkA antibody to inhibit NGF induced TrkA activation.

The term "monoclonal antibody", as used herein, generally refers to antibodies that are made by identical immune cells that are all clones of a unique parent cell. Monoclonal antibodies can have a monovalent affinity, in that they bind to the same epitope (the part of an antigen that is recognized by the antibody). Sometimes, monoclonal antibodies may also be multi specific, such as bispecific or tri specific. It has become an important tool in biochemistry, molecular biology, and medicine. Several monoclonal antibody technologies had been developed recently, such as phage display, single B cell culture, single cell amplification from various B cell populations and single plasma cell interrogation technologies.

The term "chimeric antibody", as used herein, generally refers to an antibody in which the Variable (V) region of light and heavy chains is of mouse origin, while the Constant (C) region is of human origin. In general, the chimeric antibody may retain the specificity and affinity of the original mouse monoclonal antibody, but HAMA response may be significantly reduced.

The term "humanized antibody", as used herein, generally refers to antibodies from non-human species whose protein sequences have been modified to increase their similarity to antibody variants produced naturally in humans. The amino acid sequence of a humanized antibody may be essentially identical to that of a human variant, despite the non-human origin of some of its complementarity determining region (CDR) segments responsible for the ability of the antibody to bind to its target antigen.

The term "fully human antibody" and "human antibody" are used interchangeably herein, and generally refers to an antibody that comprises a human variable region and, most preferably a human constant region. In specific embodiments, the terms refer to an antibody that comprises a variable region and constant region of human origin. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242).

The term "Fab fragment", as used herein, generally refers to a portion (such as an antigen-binding fragment) of an immunoglobulin molecule. A Fab fragment may comprise one light chain and part of a heavy chain with a single antigen-binding site. A Fab fragment may be obtained by papain digestion of an immunoglobulin molecule. For example, a Fab fragment may be composed of one constant and one variable domain of each of the heavy and the light chain. The variable domain may contain the paratope (the antigen-binding site), comprising a set of the complementarity determining regions, at the amino-terminal end of the immunoglobulin molecule. The enzyme papain may be used to cleave an immunoglobulin molecule into two Fab fragments and one Fc fragment. The enzyme pepsin cleaves below the hinge region, so a $F(ab')_2$ fragment and a pFc' fragment is formed. Divalent $F(ab)_2$ or $F(ab')_2$ fragments have two antigen binding regions that are linked by disulfide bonds. Reduction of $F(ab)_2$ or $F(ab')_2$ fragments produce 2 monovalent Fab or Fab' fragments, which have a free sulfhydryl group that is useful for conjugation to other molecules.

The term "Fv fragment", as used herein, generally refers to the smallest fragment made from enzymatic cleavage of IgG and IgM class antibodies. Fv fragments have the antigen-binding site made of the VH and VL regions, but they lack the CH1 and CL regions. The VH and VL chains may be held together in Fv fragments by non-covalent interactions.

The term "ScFv", as used herein, generally refers to a single-chain antibody fragment. An ScFv may be a recombinant single chain polypeptide molecule in which light and heavy chain variable regions of an antibody are connected, either directly or via a peptide linker. Single chain antibodies (ScFv) generally do not include portions of the Fc region of antibody, although methods are known for adding such regions to known ScFv molecules if desired. See Helfrich et al., A rapid and versatile method for harnessing ScFv antibody fragments with various biological functions. J Immunol Methods 237:131-145 (2000) and de Haard et al., Creating and engineering human antibodies for immunotherapy. Advanced Drug Delivery Reviews 31:5-31 (1998).

The term "fusion protein", as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide of a different origin, sequence or structure).

The term "protein conjugate", as used herein, generally refers to a conjugate comprising a protein (e.g., an antibody or a functional fragment thereof) conjugated to one or more additional moieties, such as cytotoxic agents, e.g., a chemotherapeutic agent, a drug, a growth inhibitory agent, a toxin (e.g., a protein toxin, an enzymatically active toxin of bacterial, fungal, plant, or animal origin, or fragments thereof), a label (e.g., a fluorescent label) and/or a radioactive isotope (i.e., a radio-conjugate).

A number of CDR definitions are in use and are encompassed herein. The Kabat definition is based on sequence variability and is the most commonly used (Kabat E A et al., ibid.). Chothia definition is based on the location of the structural loops (Chothia & Lesk J. (1987) Mol. Biol. 196:901-917). The AbM definition is a compromise between the Kabat and the Chothia definitions and is used by Oxford Molecular's AbM antibody modelling software (Martin A C R et al., (1989) PNAS USA 86:9268-9272; Martin A C R et al., (1991) Methods Enzymol. 203:121-153; Pedersen J T et al., (1992) Immunomethods 1:126-136; Rees A R et al., (1996) In Sternberg M. J. E. (ed.), Protein Structure Prediction. Oxford University Press, Oxford, 141-172). The contact definition has been recently introduced (MacCallum R M et al., (1996) J. Mol. Biol. 262:732-745) and is based on an analysis of the available complex structures available in the Protein Databank. The definition of the CDR by IMGT®, the international ImMunoGeneTics information System® (http://www.imgt.org) is based on the IMGT numbering for all immunoglobulin and T cell receptor V-REGIONs of all species (IMGT®, the international ImMunoGeneTics information System®; Lefranc M P et al., (1999) Nucleic Acids Res. 27(1):209-12; Ruiz M et al., (2000) Nucleic Acids Res. 28(1):219-21; Lefranc M P (2001) Nucleic Acids Res. 29(1):207-9; Lefranc M P (2003) Nucleic Acids Res. 31(1):307-10; Lefranc M P et al., (2005) Dev. Comp. Immunol. 29(3):185-203; Kaas Q et al., (2007) Briefings in Functional Genomics & Proteomics, 6(4):253-64).

The term "isolated nucleic acid molecule or molecules" as used herein, generally refers to a polymeric form of nucleotides of any length, either deoxyribonucleotides or ribonucleotides, or analogs thereof, isolated from its native environment, or that is artificially synthesized.

The term "vector or vectors" as used herein, generally refers to a nucleic acid vehicle into which a polynucleotide encoding a protein can be inserted and expressed. The genetic material elements carried in the vector can be expressed in a host cell by transforming, transducing, or transfecting the host cell with the vector. A vector may contain a variety of elements that control expression, including promoter sequences, transcriptional initiation sequences, enhancer sequences, selection elements, and reporter genes. In addition, the vector may also contain an origin of replication. It is also possible that the vector may include components that assist its entry into the cell, such as viral particles, liposomes or protein shells, but not only these substances.

The term "cell" as used herein, generally refers to a cell that may be used to carry the vector or vectors of the present disclosure, or be used to express or produce the antibody, the antigen binding fragment of the present disclosure. A cell of the present disclosure may be a host cell.

The terms "disease" and "disorder" may be used interchangeably herein, and generally refer to any condition that impairs the normal functioning of the body. Disease is often construed as a medical condition associated with specific symptoms and signs. It may be caused by external factors such as pathogens or by internal dysfunctions, particularly of the immune system, such as an immunodeficiency, or by a hypersensitivity, including allergies and autoimmunity.

As used herein, the term "subject" includes any human or non-human animal. The term "non-human animal" includes all vertebrates, e.g., mammals and non-mammals, such as primates, sheep, dogs, cats, horses, cows, chickens, amphibians, reptiles, etc. For example, the subject may be human.

The term "effective amount", as used herein, generally refers to a dose sufficient to provide concentrations high enough to impart a beneficial effect on the recipient thereof. The specific therapeutically effective dose level for any particular subject will depend upon a variety of factors including the disease or disorder being treated, the severity of the disease or disorder, the activity of the specific component, the route of administration, the rate of clearance, the duration of treatment, the age, body weight, sex, diet, and general health of the subject, and other related factors.

The term "pharmaceutically acceptable excipient", as used herein, generally refers to any and all solvents, dispersion media, coatings, isotonic and absorption delaying agents, etc., that are compatible with pharmaceutical administration.

The term "about", as used herein, generally refers to an approximation to a given value that would reasonably be inferred based on the ordinary skill in the art, including equivalents and approximations due to the experimental and/or measurement conditions for such given value. For example, it may refer to a value that is no more than 10% above or below the value being modified by the term.

The terms "polypeptide" or "protein", as used herein, generally refers to macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally occurring amino acid and polymers. The terms "polypeptide" and "protein" specifically encompass TrkA antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 1 10, 150, 200, 250, 300, 350, 400, or 450 amino acids long. Useful polypeptide fragments include immunologically functional fragments of antibodies, including binding domains. In the case of a TrkA-binding antibody, useful fragments include but are not limited to a CDR region, a variable domain of a heavy and/or light chain, a portion of an antibody chain or just its variable region including two CDRs, and the like.

The term "isolated protein" (such as isolated antibody), as used herein, generally refers to a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "identity", as used herein, generally refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, WI). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al, 1978, Atlas of Protein Sequence and Structure 5:345-352 for the PAM 250 comparison matrix; Henikoff et ah, 1992, Proc. Natl. Acad. ScL U.S.A. 89:10915-10919 for the BLOSUM 62 comparison matrix) is also used by the algorithm.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

An "Fc" region comprises two heavy chain fragments comprising the $C_{H1}$ and $C_{H2}$ domains of an antibody. The two heavy chain fragments are held together by two or more disulfide bonds and by hydrophobic interactions of the $C_{H3}$ domains.

A "multispecific antigen binding protein" or "multispecific antibody" is one that targets more than one antigen or epitope.

A "bispecific", "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al, 1992, J. Immunol. 148:1547-1553. The two binding sites of a bispecific antigen binding protein or antibody will bind to two different epitopes, which can reside on the same or different protein targets.

An antigen binding protein is said to "specifically bind" its target antigen when the dissociation constant (Ka) is $<10^{-7}$ M. The antigen binding protein specifically binds antigen with "high affinity" when the $K_D$ is $<5\times10^{-8}$ M, and with "very high affinity" when the $K_D$ is $<1\times10^{-8}$ M.

An antigen binding protein is "selective" when it binds to one target more tightly than it binds to a second target.

"Antigen binding region" or "antigen binding fragment" means a protein, or a portion of a protein, that specifically binds a specified antigen {e.g., a paratope). For example, that portion of an antigen binding protein that contains the amino acid residues that interact with an antigen and confer on the antigen binding protein its specificity and affinity for the antigen is referred to as "antigen binding region". An antigen binding region typically includes one or more "complementary binding regions" ("CDRs"). A "CDR" is an amino acid sequence that contributes to antigen binding specificity and affinity.

Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The term "compete", when used in the context of antigen binding proteins (e.g., antigen binding proteins or antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., TrkA or a fragment thereof, such as the ECD thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al, 1983, Methods in Enzymology 9:242-253); solid phase direct biotin-avidin EIA (see, e.g., Kirkland et al, 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al, 1988, Molec. Immunol. 25:7-15); solid phase direct biotin-avidin EIA (see, e.g., Cheung, et al, 1990, Virology 176:546-552); and direct labeled RIA (Moldenhauer et al, 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually, the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "antigen", as used herein, generally refers to a molecule or a portion of a molecule capable of being bound by a selective binding agent, such as an antigen binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen binding proteins, e.g., antibodies.

The term "epitope" includes any determinant capable of being bound by an antigen binding protein, such as an antibody or to a T-cell receptor. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies specific for a particular target antigen will preferentially recognize an epitope on the target antigen in a complex mixture of proteins and/or macromolecules.

As used herein, "substantially" or "substantial" generally means to a great or significant extent (e.g., to an extent of at least 50%, at least 60%, at least 70%, at least 80%, at least 85%, at least 90%, at least 95%, or at least 99% or more).

The term "agent" is used herein to denote a chemical compound, a mixture of chemical compounds, a biological macromolecule, or an extract made from biological materials.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al, Molecular Cloning: A Laboratory Manual (2d ed., Cold Spring Harbor Laboratory Press, Cold Spring Harbor, N. Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

Antibody or an Antigen Binding Fragment Thereof

In one aspect, the present disclosure provides an antibody or an antigen binding fragment thereof, which binds to TrkA.

The antibody, or the antigen binding fragment thereof may specifically bind to TrkA, and does not substantially bind to Tropomyosin receptor kinase B (TrkB), Tropomyosin receptor kinase C (TrkC), or p75 receptor.

The antibody, or the antigen binding fragment thereof may bind to TrkA with a $K_D$ of less than about $5.0\times10^{-8}$M, as measured by Octet or SPR. For example, with a $K_D$ of less than about $4.5\times10^{-8}$M, less than about $4\times10^{-8}$M, less than about $3.5\times10^{-8}$M, less that about $3\times10^{-8}$M, less than about $2.8\times10^{-8}$M, less than about $2.7\times10^{-8}$M, less than about $2.5\times10^{-8}$M, less than about $2\times10^{-8}$M, less than about $1.5\times10^{-8}$M, less than about $1\times10^{-8}$M, less than about $8\times10^{-9}$M, less than about $5\times10^{-9}$M, less than about $5\times10^{-9}$M, less than about $4.5\times10^{-9}$M, less than about $4\times10^{-9}$M, less than about $3.5\times10^{-9}$M, less than about $3\times10^{-9}$M, less than about $2.5\times10^{-9}$M, less than about $2\times10^{-9}$M, less than about $1.5\times10^{-9}$M, less than about $1\times10^{-9}$M, less than about $1\times10^{-10}$M, less than about $1\times10^{-11}$M, or less than about $1\times10^{-12}$M, or a $K_D$ value that is even smaller.

The antibody, or the antigen binding fragment thereof may bind to TrkA with a $K_{on}$ of more than about $1.5 \times 10^5$ (1/Ms), as measured by Octet or SPR, e.g., with a $K_{on}$ of more than about $2 \times 10^5$ (1/Ms), of more than about $3 \times 10^5$ (1/Ms), of more than about $4 \times 10^5$ (1/Ms), of more than about $5 \times 10^5$ (1/Ms), of more than about $6 \times 10^5$ (1/Ms), of more than about $7 \times 10^5$ (1/Ms), of more than about $8 \times 10^5$ (1/Ms), of more than about $9 \times 10^5$ (1/Ms), of more than about $1 \times 10^6$ (1/Ms) or more.

The antibody, or the antigen binding fragment thereof may inhibit the TrkA/NGF signaling pathway. For example, the antibody, or the antigen binding fragment thereof may inhibit the activation of TrkA induced by NGF.

The antibody, or the antigen binding fragment thereof may not substantially block the binding between TrkA and NGF.

The antibody, or the antigen binding fragment thereof may not substantially compete with NGF for binding to TrkA.

The antibody, or the antigen binding fragment thereof may block the NGF-mediated pain signaling.

The antibody, or the antigen binding fragment thereof may mitigate NGF-mediated mechanical and/or thermal sensitivity.

The antibody, or the antigen binding fragment thereof may induce antinociceptive effects in the formalin test.

The antibody, or the antigen binding fragment thereof may improve mechanical hypersensitivity in osteoarthritis pain induced by MIA injection.

The antibody, or the antigen binding fragment thereof may be capable of selectively mitigating NGF mediated pain sensitization without substantially compromising NGF's effect on neuronal growth and survival.

TrkA also known as high affinity nerve growth factor receptor, neurotrophic tyrosine kinase receptor type 1, or TRK1-transforming tyrosine kinase protein is a protein that in humans is encoded by the NTRK1 gene. An exemplary human TrkA amino acid sequence is as set forth in SEQ ID NO: 119. As described herein, TrkA proteins can also include fragments of the full length TrkA protein, such as the extracellular domain (ECD) thereof. An exemplary human TrkA ECD amino acid sequence is as set forth in SEQ ID NO: 120.

In some embodiments, the antibody, or the antigen binding fragment thereof comprises one or more CDRs (e.g., 1, 2, 3, 4, 5 or 6 CDRs). In some embodiments, the antibody, or the antigen binding fragment thereof comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature.

In certain embodiments, the polypeptide structure of the antibody, or the antigen binding fragment thereof is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antibody, or the antigen binding fragment thereof is an immunological fragment of an antibody (e.g., a Fab, a Fab', a F(ab')$_2$, or a scFv).

The antibody, or the antigen binding fragment thereof may comprise a light chain constant region. The light chain constant region may comprise a human Igκ constant region or a human Igλ constant region. In some embodiments, the light chain constant region may comprise a human Igκ constant region. In some embodiments, the light chain constant region comprises an amino acid sequence as set forth in SEQ ID NO: 121.

The antibody, or the antigen binding fragment thereof may comprise a heavy chain constant region. The heavy chain constant region may comprise a human IgG constant region (such as a human IgG1, IgG2, or IgG4 constant region). In some embodiments, the heavy chain constant region comprises a human IgG4 constant region. In some embodiments, the heavy chain constant region comprises an amino acid sequence as set forth in SEQ ID NO: 122.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., TrkA). From N-terminal to C-terminal, naturally occurring light and heavy chain variable regions both typically conform with the following order of these elements: FR1, CDR1, FR2, CDR2, FR3, CDR3 and FR4.

A numbering system has been devised for assigning numbers to amino acids that occupy positions in each of these domains. This numbering system is defined in Kabat Sequences of Proteins of Immunological Interest (1987 and 1991, NIH, Bethesda, MD), or Chothia & Lesk, 1987, J. MoL Biol. 196:901-917; Chothia et al., 1989, Nature 342: 878-883.

Various heavy chain and light chain variable regions are provided herein. In some embodiments, each of these variable regions can be attached to a heavy and light chain constant region to form a complete antibody heavy and light chain, respectively. Further, each of the so generated heavy and light chain sequences can be combined to form a complete antibody structure.

Specific examples of some of the variable regions of the light (VL) and heavy (VH) chains of the antibodies are provided and their corresponding amino acid sequences are summarized in Table 1 below.

TABLE 1

| Antibody | VH/VL |
| --- | --- |
| 48 | SEQ ID NO: 131/SEQ ID NO: 132 |
| muPHD48 | SEQ ID NO: 16/SEQ ID NO: 18 |
| PHD48-01 | SEQ ID NO: 89/SEQ ID NO: 90 |
| PHD48 | SEQ ID NO: 86/SEQ ID NO: 91 |
| PHD48-08 | SEQ ID NO: 92/SEQ ID NO: 91 |
| PHD22 | SEQ ID NO: 70/SEQ ID NO: 61 |
| PHD24 | SEQ ID NO: 74/SEQ ID NO: 61 |
| PHD25 | SEQ ID NO: 76/SEQ ID NO: 61 |
| PHD26 | SEQ ID NO: 70/SEQ ID NO: 78 |
| PHD28 | SEQ ID NO: 74/SEQ ID NO: 78 |
| PHD29 | SEQ ID NO: 76/SEQ ID NO: 78 |
| PHD30 | SEQ ID NO: 84/SEQ ID NO: 85 |
| 49 | SEQ ID NO: 133/SEQ ID NO: 134 |
| muPHD49 | SEQ ID NO: 42/SEQ ID NO: 44 |
| PHD49-01 | SEQ ID NO: 99/SEQ ID NO: 100 |
| PHD49-05 | SEQ ID NO: 105/SEQ ID NO: 104 |
| PHD49 | SEQ ID NO: 112/SEQ ID NO: 104 |
| PHD49-11 | SEQ ID NO: 106/SEQ ID NO: 107 |
| PHD49-21 | SEQ ID NO: 112/SEQ ID NO: 113 |
| muPHD50 | SEQ ID NO: 51/SEQ ID NO: 53 |
| muPHD31 | SEQ ID NO: 14/SEQ ID NO: 15 |

Each of the exemplary variable heavy chains listed in Table 1 can be combined with any of the exemplary variable light chains shown in Table 1 to form an antibody. Table 1 shows exemplary light and heavy chain pairings found in several of the antibodies disclosed herein. In some instances, the antibodies include at least one variable heavy chain and one variable light chain from those listed in Table 1. In other instances, the antibodies contain two identical light chains and two identical heavy chains. As an example, an antibody or antigen binding fragment thereof can include a heavy chain and a light chain, two heavy chains, or two light chains. In some embodiments, the antibody or the antigen binding fragment thereof comprises (and/or consists of) 1, 2, and/or 3 heavy and/or light CDRs from at least one of the sequences listed in Table 1. In some embodiments, all 6 CDRs (CDR1-3 from the light (LCDR1, LCDR2, LCDR3) and CDR 1-3 from the heavy (HCDR1, HCDR2, and HCDR3)) are part of the antibody or the antigen binding fragment thereof. In some embodiments, 1, 2, 3, 4, 5, or more CDRs are included in the antibody or the antigen binding fragment thereof. In some embodiments, one heavy and one light CDR from the CDRs in the sequences in Table 1 is included in the antibody or the antigen binding fragment thereof. In some embodiments, additional sections are also included in the antibody or the antigen binding fragment thereof. Optional light chain variable sequences (including CDR1, CDR2, and CDR3) can be selected from the following: SEQ ID NO: 132, 134, 15, and 53. Optional heavy chain variable sequences (including CDR1, CDR2 and CDR3) can be selected from the following: SEQ ID NOs: 131, 133, 14, and 51.

In some embodiments, the antibody or the antigen binding fragment thereof comprises (and/or consists of) LCDR1 and LCDR3 from at least one of the sequences listed in Table 1.

In some embodiments, the antibody or the antigen binding fragment thereof comprises (and/or consists of) HCDR1 and HCDR3 from at least one of the sequences listed in Table 1.

In some embodiments, the antibody or the antigen binding fragment thereof comprises (and/or consists of) LCDR1, LCDR3, HCDR1 and HCDR3 from at least one of the sequences listed in Table 1 (such as SEQ ID NOs: 91 and 86).

Examples of the CDRs of the antibodies shown in Table 1 are listed below (determined according to the Kabat method) in Table 2.

TABLE 2

| | (Kabat) | |
|---|---|---|
| Antibody | LCDR1-3 SEQ ID NO | HCDR1-3 SEQ ID NO |
| 48 | 96, 97, 98 | 93, 94, 95 |
| muPHD48 | 28, 30, 32 | 20, 23, 26 |
| PHD48-01 | 28, 30, 32 | 20, 23, 26 |
| PHD48 | 88, 30, 32 | 20, 87, 26 |
| PHD48-08 | 88, 30, 32 | 20, 87, 26 |
| PHD22 | 56, 58, 60 | 62, 65, 68 |
| PHD24 | 56, 58, 60 | 20, 73, 68 |
| PHD25 | 56, 58, 60 | 20, 75, 68 |
| PHD26 | 56, 77, 60 | 62, 65, 68 |
| PHD28 | 56, 77, 60 | 20, 73, 68 |
| PHD29 | 56, 77, 60 | 20, 75, 68 |
| PHD30 | 80, 82, 32 | 62, 79, 26 |
| 49 | 117, 118, 41 | 114 (SX$_1$WX$_2$Q, wherein X$_1$ is H or Y, X$_2$ is I or M), 115, 116 |
| muPHD49 | 28, 39, 41 | 45, 46, 37 |
| PHD49-01 | 28, 39, 41 | 45, 46, 37 |
| PHD49-05 | 88, 103, 41 | 101, 102, 37 |

TABLE 2-continued

| | (Kabat) | |
|---|---|---|
| Antibody | LCDR1-3 SEQ ID NO | HCDR1-3 SEQ ID NO |
| PHD49 | 88, 103, 41 | 109, 110, 111 |
| PHD49-11 | 88, 39, 41 | 45, 46, 37 |
| PHD49-21 | 39, 108, 41 | 109, 110, 111 |
| muPHD50 | 50, 39, 41 | 47, 48, 49 |
| muPHD31 | 9, 11, 13 | 1, 4, 7 |

Some of the exemplary antibodies provided in the present disclosure are considered alternatives or variants to each other. For example, muPHD48, PHD48-01, PHD48, PHD48-08, PHD22, PHD24, PHD25, PHD26, PHD28, PHD29 and PHD30 may be considered variants or alternatives to each other. As another example, muPHD49, PHD49-01, PHD49-05, PHD49, PHD49-11, and PHD49-21 may be considered variants or alternatives to each other.

In some embodiments, the antibody or the antigen binding fragment thereof is capable of binding to an epitope recognized by one of the antibodies described in Table 1. In some embodiments, the antibody, or the antigen binding fragment thereof is capable of binding to a specific conformational state of TrkA so as to inhibit TrkA activation (e.g., TrkA activation induced by NGF) while not blocking binding of NGF to TrkA.

As described herein, the TrkA antibody or the antigen binding fragment thereof can comprise a humanized antibody and/or part thereof. An important practical application of such a strategy is the "humanization" of the mouse humoral immune system. In certain embodiments, a humanized antibody is substantially non-immunogenic in humans. In certain embodiments, a humanized antibody has substantially the same affinity for a target as an antibody from another species from which the humanized antibody is derived.

In certain embodiments, amino acids of an antibody variable domain that can be modified without diminishing the native affinity of the antigen binding domain while reducing its immunogenicity are identified.

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. See, e.g., Co et al., Mol. Immunol., 30:1361-1367 (1993). In certain embodiments, techniques such as "reshaping", "hyperchimerization" or "veneering/resurfacing" are used to produce humanized antibodies. See, e.g., Vaswami et al., Annals of Allergy, Asthma, & Immunol. 81:105 (1998); Roguska et al, Prot. Engineer., 9:895-904 (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies.

In certain instances, humanizing antibodies results in a loss of antigen binding capacity. In certain embodiments, humanized antibodies are "back mutated". In certain such embodiments, the humanized antibody is mutated to include one or more of the amino acid residues found in the donor antibody. See, e.g., Saldanha et ai, Mol Immunol 36:709-19 (1999).

In certain embodiments the complementarity determining regions (CDRs) of the light and heavy chain variable regions of an antibody to TrkA can be grafted to framework regions (FRs) from the same, or another, species. In certain embodiments, the CDRs of the light and heavy chain variable regions of an antibody to TrkA can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to TrkA heavy chain or light chain are replaced with the FRs from a different heavy chain or light chain. In certain embodiments, rare amino acids in the FRs of the heavy and light chains of an antibody to TrkA are not replaced, while the rest of the FR amino acids are replaced. Rare amino acids are specific amino acids that are in positions in which they are not usually found in FRs. In certain embodiments, the grafted variable regions from an antibody to TrkA can be used with a constant region that is different from the constant region of an antibody to TrkA. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al, Nature, 321: 522-525 (1986); Riechmann et al, Nature, 332: 323-327 (1988); Verhoeyen et al, Science, 239:1534-1536 (1988), Winter, FEBS Letts., 430:92-94 (1998), which are hereby incorporated by reference for any purpose.

As described herein, an antibody or its antigen binding fragment that binds to TrkA can comprise a human (i.e., fully human) antibody and/or part thereof. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments a hybridoma cell line is selected from at least one of the cell lines described in Table 1, e.g., muPHD31, muPHD48, muPHD49 and/or muPHD50. In certain embodiments, a purified human monoclonal antibody to human TrkA is provided.

One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in WO 98/24893, U.S. Pat. No. 5,545,807, EP 546073, and EP 546073.

In certain embodiments, one can use constant regions from species other than human along with the human variable region(s).

The ability to clone and reconstruct megabase sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide insights into the expression and regulation of human gene products during development, their communication with other systems, and their involvement in disease induction and progression.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

Humanized antibodies are those antibodies that, while initially starting off containing antibody amino acid sequences that are not human, have had at least some of these nonhuman antibody amino acid sequences replaced with human antibody sequences. This is in contrast with human antibodies, in which the antibody is encoded (or capable of being encoded) by genes possessed a human.

Other antibodies that are provided are variants of the antibody or the antigen binding fragment thereof listed above formed by combination or subparts of the variable heavy and variable light chains shown in Table 1 and comprise variable light and/or variable heavy chains that each have at least 50%, 50%-60%, 60%-70%, 70%-80%, 80%-85%, 85%-90%, 90%-95%, 95%-97%, 97%-99%, or above 99% identity to the amino acid sequences of the sequences in Table 1 (either the entire sequence or a subpart of the sequence, e.g., one or more CDR). In some instances, such antibodies include at least one heavy chain and one light chain, whereas in other instances the variant forms contain two identical light chains and two identical heavy chains (or subparts thereof). In some embodiments, sequence comparison can be used in order to identify sections of the antibodies that can be modified by observing those variations that impact binding and those variations that do not appear to impact binding. For example, by comparing similar sequences, one can identify those sections (e.g., particular amino acids) that can be modified and how they can be modified while still retaining (or improving) the functionality of the antibody or the antigen binding fragment thereof. In some embodiments, variants of the antibody include consensus groups and sequences between alternatives, as described above. The CDRs shown in Table 2 are defined based upon the Kabat method (based on sequence variability, see, e.g., Sequences of Proteins of Immunological Interest, Fifth Edition. NIH Publication No. 91-3242, Kabat et al., (1991)).

In certain embodiments, the antibody or its antigen binding fragment comprises a heavy chain comprising a variable region comprising an amino acid sequence at least 90% identical to an amino acid sequence selected from at least one of the sequences of SEQ ID NOs: 131, 133, 14 and 51. In certain embodiments, the antibody or its antigen binding fragment comprises a heavy chain comprising a variable region comprising an amino acid sequence at least 95% identical to an amino acid sequence selected from at least one of the sequences of SEQ ID NOs: 131, 133, 14 and 51. In certain embodiments, the antibody or its antigen binding fragment comprises a heavy chain comprising a variable region comprising an amino acid sequence at least 99% identical to an amino acid sequence selected from at least one of the sequences of SEQ ID NOs: 131, 133, 14 and 51.

In some embodiments, the antibody or its antigen binding fragment comprises a sequence that is at least 90%, 90-95%, and/or 95-99% identical to one or more CDRs from the CDRs in at least one of sequences of SEQ ID NOs: 131, 133, 14 and 51. In some embodiments, 1, 2, 3, 4, 5, or 6 CDR (each being at least 90%, 90-95%, and/or 95-99% identical to the above sequences) is present.

In some embodiments, the antibody or its antigen binding fragment comprises a sequence that is at least 90%, 90-95%, and/or 95-99% identical to one or more FRs from the FRs in at least one of sequences of SEQ ID NOs: 131, 133, 14 and 51. In some embodiments, 1, 2, 3, or 4 FR (each being at least 90%, 90-95%, and/or 95-99% identical to the above sequences) is present.

In certain embodiments, the antibody or its antigen binding fragment comprises a light chain comprising a variable region comprising an amino acid sequence at least 90% identical to an amino acid sequence selected from at least one of the sequences of SEQ ID NOs: 132, 134, 15, and 53. In certain embodiments, the antibody or its antigen binding fragment comprises a light chain comprising a variable region comprising an amino acid sequence at least 95% identical to an amino acid sequence selected from at least one of the sequences of SEQ ID NOs: 132, 134, 15, and 53. In certain embodiments, an antigen binding fragment thereof comprises a light chain comprising a variable region comprising an amino acid sequence at least 99% identical to an amino acid sequence selected from at least one of the sequences of SEQ ID NOs: 132, 134, 15, and 53.

In some embodiments, the antibody or its antigen binding fragment comprises a sequence that is at least 90%, 90-95%, and/or 95-99% identical to one or more CDRs from the CDRs in at least one of sequences of SEQ ID NOs: 132, 134, 15, and 53. In some embodiments, 1, 2, 3, 4, 5, or 6 CDR (each being at least 90%, 90-95%, and/or 95-99% identical to the above sequences) is present.

In some embodiments, the antibody or its antigen binding fragment comprises a sequence that is at least 90%, 90-95%, and/or 95-99% identical to one or more FRs from the FRs in at least one of sequences of SEQ ID NOs: 132, 134, 15, and 53. In some embodiments, 1, 2, 3, or 4 FR (each being at least 90%, 90-95%, and/or 95-99% identical to the above sequences) is present.

In light of the present disclosure, a skilled artisan will be able to determine suitable variants of the antibody or the antigen binding fragment thereof as set forth herein using well-known techniques. In certain embodiments, one skilled in the art can identify suitable areas of the molecule that may be changed without destroying activity by targeting regions not believed to be important for activity. In certain embodiments, one can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar antibodies. In view of such information, one skilled in the art can predict the alignment of amino acid residues of an antibody with respect to its three dimensional structure. In certain embodiments, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known to those skilled in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

In certain embodiments, antigen binding fragment thereof variants include glycosylation variants wherein the number and/or type of glycosylation site has been altered compared to the amino acid sequences of a parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) can be made in the naturally occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, N. Y. (1991)); and Thornton et al, Nature, 354:105 (1991), which are each incorporated herein by reference.

In some embodiments, the variants are variants of the nucleic acid sequences of the antibody or the antigen binding fragment thereof disclosed herein. One of skill in the art will appreciate that the above discussion can be used for identifying, evaluating, and/or creating antibodies and protein variants and also for nucleic acid sequences that can encode for those protein variants. Thus, nucleic acid sequences encoding for those protein variants (as well as nucleic acid sequences that encode for the antibody or the antigen binding fragment thereof in Table 1, but are different from those explicitly disclosed herein) are contemplated.

In certain embodiments, the antibody, or the antigen binding fragment thereof are produced by immunization with an antigen (e.g., TrkA). In certain embodiments, antibodies can be produced by immunization with full-length TrkA, a soluble form of TrkA, the extracellular domain alone, a splice variant form of TrkA, or a fragment thereof. In certain embodiments, the antibodies of the present disclosure can be polyclonal or monoclonal, and/or can be recombinant antibodies. In certain embodiments, antibodies of the present disclosure are human antibodies prepared, for example, by immunization of transgenic animals capable of producing human antibodies (see, for example, PCT Application No. WO 93/12227).

In certain embodiments, certain strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In certain embodiments, amino acids in the framework regions of the variable domains are targeted. In certain embodiments, such framework regions have been shown to contribute to the target binding properties of certain antibodies. See, e.g., Hudson, Curr. Opin. Biotech., 9:395-402 (1999) and references therein.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive TrkA binding properties.

In certain embodiments, the antibody, or the antigen binding fragment thereof comprises an immunoglobulin molecule of at least one of the IgG1, IgG2, IgG3, IgG4, Ig E, IgA, IgD, and IgM isotype. In certain embodiments, the antibody, or the antigen binding fragment thereof comprises a human kappa light chain and/or a human heavy chain. In certain embodiments, the heavy chain is of the IgG1, IgG2, IgG3, IgG4, IgE, IgA, IgD, or IgM isotype. In certain embodiments, the antibody, or the antigen binding fragment thereof has been cloned for expression in mammalian cells. In certain embodiments, the antibody, or the antigen binding fragment thereof comprises a constant region other than any of the constant regions of the IgG1, IgG2, IgG3, IgG4, IgE, IgA, IgD, and IgM isotype.

Epitopes to which anti-TrkA antibodies bind are provided. In some embodiments, epitopes that are bound by the presently disclosed antibodies are particularly useful. In some embodiments, the antibody, or the antigen binding fragment thereof that binds to any of the epitopes that are bound by the antibodies described herein are useful. In some embodiments, the epitopes bound by any of the antibodies listed in Table 1 are especially useful. In some embodiments, the epitope is on the extracellular domain of TrkA.

In certain embodiments, a TrkA epitope can be utilized to prevent (e.g., reduce) binding of an anti-TrkA antibody or antigen binding fragment thereof to TrkA. In certain embodiments, a TrkA epitope can be utilized to decrease binding of an anti-TrkA antibody or antigen binding fragment thereof to TrkA. In certain embodiments, a TrkA epitope can be utilized to substantially inhibit binding of an anti-TrkA antibody or antigen binding fragment thereof to TrkA.

In certain embodiments, a TrkA epitope can be utilized to isolate antibodies or antibody, or the antigen binding fragment thereof that bind to TrkA. In certain embodiments, a TrkA epitope can be utilized to generate antibodies or the antigen binding fragment thereof which bind to TrkA. In certain embodiments, a TrkA epitope or a sequence comprising a TrkA epitope can be utilized as an immunogen to generate antibodies that bind to TrkA. In certain embodiments, a TrkA epitope can be administered to an animal, and antibodies that bind to TrkA can subsequently be obtained from the animal. In certain embodiments, a TrkA epitope or a sequence comprising a TrkA epitope can be utilized to interfere with normal TrkA-mediated activity, such as TrkA activation induced by NGF.

In some embodiments, the antibody, or the antigen binding fragment thereof disclosed herein bind specifically to TrkA ECD. In some embodiments, the domain(s)/region(s) containing residues that are in contact with or are buried by an antibody can be identified by mutating specific residues in TrkA (e.g., a wild-type antigen) and determining whether the antigen binding fragment thereof can bind the mutated or variant TrkA protein. By making a number of individual mutations, residues that play a direct role in binding or that are in sufficiently close proximity to the antibody such that a mutation can affect binding between the antigen binding fragment thereof and antigen can be identified. From a knowledge of these amino acids, the domain(s) or region(s) of the antigen that contain residues in contact with the antigen binding fragment thereof or covered by the antibody can be elucidated. Such a domain can include the binding epitope of an antigen binding fragment thereof. One specific example of this general approach utilizes an arginine/glutamic acid scanning protocol (see, e.g., Nanevicz, T., et ai, 1995, J. Biol. Chem., 270:37, 21619-21625 and Zupnick, A., et al, 2006, J. Biol. Chem., 28_L:29, 20464-20473). In general, arginine and glutamic acids are substituted (typically individually) for an amino acid in the wild-type polypeptide because these amino acids are charged and bulky and thus have the potential to disrupt binding between an antigen binding fragment thereof and an antigen in the region of the antigen where the mutation is introduced. Arginines that exist in the wild-type antigen are replaced with glutamic acid. A variety of such individual mutants are obtained and the collected binding results analyzed to determine what residues affect binding.

As noted above, residues directly involved in binding or covered by an antigen binding fragment thereof can be identified from scanning results or Cryo-EM. These residues can thus provide an indication of the domains or regions of SEQ ID NO: 119 (or SEQ ID NO: 120) that contain the binding region(s) to which antibody, or the antigen binding fragment thereof of the present disclosure bind. As can be seen from the results summarized in Example 8, in some embodiments, an antigen binding fragment thereof binds to a domain containing at least one of amino acids: Q176, H178, G179, Q180, and P187 of SEQ ID NO: 119.

In the present application, the antibody or the antigen binding fragment thereof may be capable of recognizing an epitope of TrkA extracellular domain (ECD) comprising amino acid residues: Q176, H178, G179, Q180, and/or P187 of SEQ ID NO: 119. For example, the epitope may comprise one or more (for example, 2, 3, 4, or 5) amino acid residues of Q176, H178, G179, Q180, and P187 of SEQ ID NO: 119.

In some cases, the antibody or the antigen binding fragment thereof may be capable of specifically binding to Q176, H178, G179, Q180 and/or P187 of SEQ ID NO: 119. For example, the antibody or the antigen binding fragment thereof may be capable of specifically binding to one or more (for example, 2, 3, 4, or 5) amino acid residues of Q176, H178, G179, Q180, and P187 of SEQ ID NO: 119.

In some cases, the ECD of TrkA comprises an amino acid sequence as set forth in SEQ ID NO: 120. In the present application, the TrkA may comprises an amino acid sequence as set forth in SEQ ID NO: 119.

In some cases, the distance between the antigen atom and corresponding interaction site of said antibody or the antigen binding fragment may be no more than about 4.00 Å, for example, 3.76 Å, 3.62 Å, 3.43 Å, 3.36 Å, 3.13 Å, 3.06 Å, and/or 2.68 Å.

In some cases, the interaction site of the antibody which binds to antigen atom Q176 may be heavy chain W33 of SEQ ID NO: 86 or a corresponding residue (e.g., the correspondence may be determined via sequence alignment). In some cases, the interaction site of the antibody which binds to antigen atom H178 may be light chain Y90 of SEQ ID NO: 91 or a corresponding residue. In some cases, the interaction site of the antibody which binds to antigen atom G179 may be heavy chain H35 of SEQ ID NO: 86 or a corresponding residue. In some cases, the interaction site of the antibody which binds to antigen atom G179 may be light chain Y90 of SEQ ID NO: 91 or a corresponding residue. In some cases, the interaction site of the antibody which binds to antigen atom Q180 may be heavy chain W104 of SEQ ID NO: 86 or a corresponding residue. In some cases, the interaction site of the antibody which binds to antigen atom Q180 may be light chain Y90 of SEQ ID NO: 91 or a corresponding residue. In some cases, the interaction site of the antibody which binds to antigen atom P187 may be light chain Y31 of SEQ ID NO: 91 or a corresponding residue.

In another aspect, the present application provides a method for screening for or obtaining a TrkA antibody which does not substantially block the binding between TrkA and NGF. The method may comprise using an epitope of TrkA extracellular domain (ECD) comprising amino acid residues: Q176, H178, G179, Q180, and/or P187 of SEQ ID NO: 119. For example, the epitope of TrkA extracellular domain (ECD) may comprise one or more (e.g., 2, 3, 4, or 5) amino acid residues of Q176, H178, G179, Q180, and P187 of SEQ ID NO: 119. For example, the TrkA antibody may comprise one or more of the following properties: is capable of binding to TrkA with a $K_D$ of less than about $5*10^{-8}$ M, as measured by Octet or SPR; is capable of inhibiting the activation of TrkA induced by NGF; does not substantially compete with NGF for binding to TrkA; and is capable of mitigating pain sensitization (such as NGF mediated pain sensitization, e.g., NGF mediated pain sensitization without substantially compromising NGF's effect on neuronal growth and survival). For example, the method may be an in vitro or ex vivo method. The antibody or the antigen binding fragment thereof may specifically recognize or bind to an epitope of the TrkA extracellular domain (ECD), the epitope may comprise amino acid residues: Q176, H178, G179, Q180, and/or P187 of SEQ ID NO: 119.

In some embodiments, a shortened or truncated TrkA protein (e.g., human TrkA protein) or the ECD thereof is used to immunize an animal (such as a mouse, or rabbit, or other non-human animal) or is introduced into an antibody generating cell (such as a B cell, e.g., a human B cell), and antibodies specifically binding to the truncated TrkA protein may be further analyzed or selected. The truncated TrkA protein comprises amino acid residues: Q176, H178, G179, Q180, and/or P187 of SEQ ID NO: 119.

In some cases, a mutated or modified TrkA protein may be used, wherein one or more residues corresponding to Q176, H178, G179, Q180 and/or P187 of SEQ ID NO: 119 is mutated to a different residue or is deleted. If a candidate antibody or the antigen binding fragment thereof does not bind to the mutated or modified TrkA protein, or binds to it with a significantly lower affinity (e.g., with a $K_D$ value that is 20% higher, 25% higher, 30% higher, 35% higher, 40% higher, 45% higher, 50% higher, 55% higher, 60% higher, 65% higher, 70% or more higher), then the antibody or the antigen binding fragment thereof may be further analyzed or selected, as it might be considered an antibody (or the antigen binding fragment thereof) having the desired properties, e.g., properties comprised by the antibodies or the antigen binding fragment of the present disclosure.

In another aspect, the present application provides use of an epitope of TrkA extracellular domain (ECD) for obtaining or screening for a TrkA antibody which does not substantially block the binding between TrkA and NGF, wherein said epitope comprises amino acid residues: Q176, H178, G179, Q180, and/or P187 of SEQ ID NO: 119.

In another aspect, the present disclosure provides use of an epitope of TrkA extracellular domain (ECD) in the manufacture of an agent for obtaining or screening for a TrkA antibody which does not substantially block the binding between TrkA and NGF, wherein the epitope comprises amino acid residues: Q176, H178, G179, Q180, and/or P187 of SEQ ID NO: 119.

In some cases, the antibody or the antigen binding fragment thereof may capable of competing with a reference antibody for binding to the TrkA, wherein the reference antibody comprises light chain CDR1-3 and heavy chain CDR1-3, the light chain CDR1-3 comprises the amino acid sequence as set forth in SEQ ID NOs: 96, 97, and 98 respectively, and the heavy chain CDR1-3 comprises the amino acid sequence as set forth in SEQ ID NOs: 93, 94, and 95 respectively.

In some cases, the reference antibody comprises light chain CDR1-3 and heavy chain CDR1-3, the light chain CDR1-3 comprises the amino acid sequence as set forth in SEQ ID NOs: 117, 118, and 41 respectively, and the heavy chain CDR1-3 comprises the amino acid sequence as set forth in SEQ ID NOs: 114 ($SX_1WX_2Q$, wherein $X_1$ is H or Y, $X_2$ is I or M), 115, and 116 respectively.

In some cases, the reference antibody comprises light chain CDR1-3 and heavy chain CDR1-3, the light chain CDR1-3 comprising the amino acid sequence as set forth in SEQ ID NOs: 9, 11, and 13 respectively, and the heavy chain CDR1-3 comprising the amino acid sequence as set forth in SEQ ID NO: 1, 4, and 7 respectively.

In some cases, the reference antibody comprises light chain CDR1-3 and heavy chain CDR1-3, the light chain CDR1-3 comprising the amino acid sequence as set forth in SEQ ID NOs: 28, 30, and 32 respectively, and the heavy chain CDR1-3 comprising the amino acid sequence as set forth in SEQ ID NO: 20, 23, and 26 respectively.

In some cases, the reference antibody comprises light chain CDR1-3 and heavy chain CDR1-3, the light chain CDR1-3 comprising the amino acid sequence as set forth in SEQ ID NOs: 56, 58, and 60 respectively, and the heavy chain CDR1-3 comprising the amino acid sequence as set forth in SEQ ID NOs: 62, 65, and 68 respectively.

In some cases, the reference antibody comprises light chain CDR1-3 and heavy chain CDR1-3, the light chain CDR1-3 comprising the amino acid sequence as set forth in SEQ ID NOs: 56, 58, and 60 respectively, and the heavy chain CDR1-3 comprising the amino acid sequence as set forth in SEQ ID NOs: 20, 73, and 68 respectively.

In some cases, the reference antibody comprises light chain CDR1-3 and heavy chain CDR1-3, the light chain CDR1-3 comprising the amino acid sequence as set forth in SEQ ID NOs: 56, 58, and 60 respectively, and the heavy chain CDR1-3 comprising the amino acid sequence as set forth in SEQ ID NOs: 20, 75, and 68 respectively.

In some cases, the reference antibody comprises light chain CDR1-3 and heavy chain CDR1-3, the light chain CDR1-3 comprising the amino acid sequence as set forth in SEQ ID NOs: 56, 77, and 60 respectively, and the heavy chain CDR1-3 comprising the amino acid sequence as set forth in SEQ ID NOs: 62, 65, and 68 respectively.

In some cases, the reference antibody comprises light chain CDR1-3 and heavy chain CDR1-3, the light chain CDR1-3 comprising the amino acid sequence as set forth in SEQ ID NOs: 56, 77, and 60 respectively, and the heavy chain CDR1-3 comprising the amino acid sequence as set forth in SEQ ID NOs: 20, 73, and 68 respectively.

In some cases, the reference antibody comprises light chain CDR1-3 and heavy chain CDR1-3, the light chain CDR1-3 comprising the amino acid sequence as set forth in SEQ ID NOs: 56, 77, and 60 respectively, and the heavy chain CDR1-3 comprising the amino acid sequence as set forth in SEQ ID NOs: 20, 75, and 68 respectively.

In some cases, the reference antibody comprises light chain CDR1-3 and heavy chain CDR1-3, the light chain CDR1-3 comprising the amino acid sequence as set forth in SEQ ID NOs: 80, 82, and 32 respectively, and the heavy chain CDR1-3 comprising the amino acid sequence as set forth in SEQ ID NOs: 62, 79 and 26 respectively.

In some cases, the reference antibody comprises light chain CDR1-3 and heavy chain CDR1-3, the light chain CDR1-3 comprising the amino acid sequence as set forth in SEQ ID NOs: 88, 30, and 32 respectively, and the heavy chain CDR1-3 comprising the amino acid sequence as set forth in SEQ ID NOs: 20, 87, and 26 respectively.

In some cases, the reference antibody comprises light chain CDR1-3 and heavy chain CDR1-3, the light chain CDR1-3 comprising the amino acid sequence as set forth in SEQ ID NOs: 28, 39, and 41 respectively, and the heavy chain CDR1-3 comprising the amino acid sequence as set forth in SEQ ID NOs: 45, 46, and 37 respectively.

In some cases, the reference antibody comprises light chain CDR1-3 and heavy chain CDR1-3, the light chain CDR1-3 comprising the amino acid sequence as set forth in SEQ ID NOs: 88, 103, and 41 respectively, and the heavy chain CDR1-3 comprising the amino acid sequence as set forth in SEQ ID NOs: 101, 102, and 37 respectively.

In some cases, the reference antibody comprises light chain CDR1-3 and heavy chain CDR1-3, the light chain CDR1-3 comprising the amino acid sequence as set forth in SEQ ID NOs: 88, 103, and 41 respectively, and the heavy chain CDR1-3 comprising the amino acid sequence as set forth in SEQ ID NOs: 109, 110, and 111 respectively.

In some cases, the reference antibody comprises light chain CDR1-3 and heavy chain CDR1-3, the light chain CDR1-3 comprising the amino acid sequence as set forth in SEQ ID NOs: 88, 39, and 41 respectively, and the heavy chain CDR1-3 comprising the amino acid sequence as set forth in SEQ ID NOs: 45, 46, and 37 respectively.

In some cases, the reference antibody comprises light chain CDR1-3 and heavy chain CDR1-3, the light chain CDR1-3 comprising the amino acid sequence as set forth in SEQ ID NOs: 39, 108 and 41 respectively, and the heavy chain CDR1-3 comprising the amino acid sequence as set forth in SEQ ID NOs: 109, 110, and 111 respectively.

In some cases, the reference antibody comprises light chain CDR1-3 and heavy chain CDR1-3, the light chain CDR1-3 comprising the amino acid sequence as set forth in SEQ ID NOs: 50, 39, and 41 respectively, and the heavy chain CDR1-3 comprising the amino acid sequence as set forth in SEQ ID NOs: 47, 48, and 49 respectively.

In some embodiments, the antibody or the antigen binding fragment thereof comprises at least one of light chain CDRs 1-3 of a light chain variable region, and the light chain variable region comprises an amino acid sequence as set forth in any one of SEQ ID NOs: 132, 134, 15, and 53.

In some embodiments, the antibody or the antigen binding fragment thereof comprises at least one of heavy chain CDRs 1-3 of a heavy chain variable region, and the heavy chain variable region comprises an amino acid sequence as set forth in any one of SEQ ID NOs: 131, 133, 14 and 51.

In some embodiments, the antibody or the antigen binding fragment thereof comprises a light chain CDR1, and the light chain CDR1 comprises an amino acid sequence as set forth in any one of SEQ ID NOs: 96, 117, 9, and 50.

In some embodiments, the antibody or the antigen binding fragment thereof comprises a light chain CDR1, and the light chain CDR1 comprises an amino acid sequence as set forth in any one of SEQ ID NOs: 9, 28, 50, 56, 80, and 88.

In some embodiments, the antibody or the antigen binding fragment thereof comprises a light chain CDR2, and the light chain CDR2 comprises an amino acid sequence as set forth in any one of SEQ ID NOs: 97, 118, and 11.

In some embodiments, the antibody or the antigen binding fragment thereof comprises a light chain CDR2, and the light chain CDR2 comprises an amino acid sequence as set forth in any one of SEQ ID NOs: 11, 30, 39, 58, 77, 82, 103, and 108.

In some embodiments, the antibody or the antigen binding fragment thereof comprises a light chain CDR3, and the light chain CDR3 comprises an amino acid sequence as set forth in any one of SEQ ID NOs: 98, 13, and 41.

In some embodiments, the antibody or the antigen binding fragment thereof comprises a light chain CDR3, and the light chain CDR3 comprises an amino acid sequence as set forth in any one of SEQ ID NOs: 13, 32, 41, 60.

In some embodiments, the antibody or the antigen binding fragment thereof comprises a light chain variable region, and the light chain variable region comprises an amino acid sequence as set forth in any one of SEQ ID NOs: 132, 134, 15, and 53.

In some embodiments, the antibody or the antigen binding fragment thereof comprises a heavy chain CDR1, and the heavy chain CDR1 comprises an amino acid sequence as set forth in any one of SEQ ID NOs: 93, 114 ($SX_1WX_2Q$, wherein $X_1$ is H or Y, $X_2$ is I or M), 1, and 47.

In some embodiments, the antibody or the antigen binding fragment thereof comprises a heavy chain CDR1, and the heavy chain CDR1 comprises an amino acid sequence as set forth in any one of SEQ ID NOs: 1, 20, 45, 47, 62, 101, and 109.

In some embodiments, the antibody or the antigen binding fragment thereof comprises a heavy chain CDR2, and the heavy chain CDR2 comprises an amino acid sequence as set forth in any one of SEQ ID NOs: 94, 115, 4, and 48.

In some embodiments, the antibody or the antigen binding fragment thereof comprises a heavy chain CDR2, and the heavy chain CDR2 comprises an amino acid sequence as set forth in any one of SEQ ID NOs: 4, 23, 46, 48, 65, 73, 75, 87, 102, and 110.

In some embodiments, the antibody or the antigen binding fragment thereof comprises a heavy chain CDR3, and the heavy chain CDR3 comprises an amino acid sequence as set forth in any one of SEQ ID NOs: 95, 116, 7, and 49.

In some embodiments, the antibody or the antigen binding fragment thereof comprises a heavy chain CDR3, and the heavy chain CDR3 comprises an amino acid sequence as set forth in any one of SEQ ID NOs: 7, 26, 37, 49, 68, and 111.

In some embodiments, the antibody or the antigen binding fragment thereof comprises a heavy chain variable region, and the heavy chain variable region comprises an amino acid sequence as set forth in any one of SEQ ID NOs: 131, 133, 14, and 51.

In some embodiments, the antibody or the antigen binding fragment thereof comprises: 1) light chain CDR1-3 comprising the amino acid sequence as set forth in SEQ ID NOs: 96, 97, and 98 respectively, and heavy chain CDR1-3 comprising the amino acid sequence as set forth in SEQ ID NOs: 93, 94, and 95 respectively; 2) light chain CDR1-3 comprising the amino acid sequence as set forth in SEQ ID NOs: 117, 118, and 41 respectively, and heavy chain CDR1-3 comprising the amino acid sequence as set forth in SEQ ID NOs: 114 ($SX_1WX_2Q$, wherein $X_1$ is H or Y, $X_2$ is I or M), 115, and 116 respectively; 3) light chain CDR1-3 comprising the amino acid sequence as set forth in SEQ ID NOs: 9, 11, and 13 respectively, and heavy chain CDR1-3 comprising the amino acid sequence as set forth in SEQ ID NOs: 1, 4, and 7 respectively; 4) light chain CDR1-3 comprising the amino acid sequence as set forth in SEQ ID NOs: 28, 30, and 32 respectively, and heavy chain CDR1-3 comprising the amino acid sequence as set forth in SEQ ID NOs: 20, 23, and 26 respectively; 5) light chain CDR1-3 comprising the amino acid sequence as set forth in SEQ ID NOs: 56, 58, and 60 respectively, and heavy chain CDR1-3 comprising the amino acid sequence as set forth in SEQ ID NOs: 62, 65, and 68 respectively; 6) light chain CDR1-3 comprising the amino acid sequence as set forth in SEQ ID NOs: 56, 58, and 60 respectively, and heavy chain CDR1-3 comprising the amino acid sequence as set forth in SEQ ID NOs: 20, 73, and 68 respectively; 7) light chain CDR1-3 comprising the amino acid sequence as set forth in SEQ ID NOs: 56, 58, and 60 respectively, and heavy chain CDR1-3 comprising the amino acid sequence as set forth in SEQ ID NOs: 20, 75, and 68 respectively; 8) light chain CDR1-3 comprising the amino acid sequence as set forth in SEQ ID NOs: 56, 77, and 60 respectively, and heavy chain CDR1-3 comprising the amino acid sequence as set forth in SEQ ID NOs: 62, 65, and 68 respectively; 9) light chain CDR1-3 comprising the amino acid sequence as set forth in SEQ ID NOs: 56, 77, and 60 respectively, and heavy chain CDR1-3 comprising the amino acid sequence as set forth in SEQ ID NOs: 20, 73, and 68 respectively; 10) light chain CDR1-3 comprising the amino acid sequence as set forth in SEQ ID NOs: 56, 77, and 60 respectively, and heavy chain CDR1-3 comprising the amino acid sequence as set forth in SEQ ID NOs: 20, 75, and 68 respectively; 11) light chain CDR1-3 comprising the amino acid sequence as set forth in SEQ ID NOs: 80, 82, and 32 respectively, and heavy chain CDR1-3 comprising the amino acid sequence as set forth in SEQ ID NOs: 62, 79 and 26 respectively; 12) light chain CDR1-3 comprising the amino acid sequence as set forth in SEQ ID NOs: 88, 30, and 32 respectively, and heavy chain CDR1-3 comprising the amino acid sequence as set forth in SEQ ID NOs: 20, 87, and 26 respectively; 13) light chain CDR1-3 comprising the amino acid sequence as set forth in SEQ ID NOs: 28, 39, and 41 respectively, and heavy chain CDR1-3 comprising the amino acid sequence as set forth in SEQ ID NOs: 45, 46, and 37 respectively; 14) light chain CDR1-3 comprising the amino acid sequence as set forth in SEQ ID NOs: 88, 103, and 41 respectively, and heavy chain CDR1-3 comprising the amino acid sequence as set forth in SEQ ID NOs: 101, 102, and 37 respectively; 15) light chain CDR1-3 comprising the amino acid sequence as set forth in SEQ ID NOs: 88, 103, and 41 respectively, and heavy chain CDR1-3 comprising the amino acid sequence as set forth in SEQ ID NOs: 109, 110, and 111 respectively; 16) light chain CDR1-3 comprising the amino acid sequence as set forth in SEQ ID NOs: 88, 39, and 41 respectively, and heavy chain CDR1-3 comprising the amino acid sequence as set forth in SEQ ID NO: 45, 46, and 37 respectively; 17) light chain CDR1-3 comprising the amino acid sequence as set forth in SEQ ID NOs: 39, 108 and 41 respectively, and heavy chain CDR1-3 comprising the amino acid sequence as set forth in SEQ ID NOs: 109, 110, and 111 respectively; or 18) light chain CDR1-3 comprising the amino acid sequence as set forth in SEQ ID NOs: 50, 39, and 41 respectively, and heavy chain CDR1-3 comprising the amino acid sequence as set forth in SEQ ID NOs: 47, 48, and 49 respectively.

In some embodiments, the antibody or the antigen binding fragment thereof comprises: 1) a light chain variable region comprising the amino acid sequence as set forth in SEQ ID NO: 132, and a heavy chain variable region comprising the amino acid sequence as set forth in SEQ ID NO: 131; 2) a light chain variable region comprising the amino acid sequence as set forth in SEQ ID NO: 134, and a heavy chain variable region comprising the amino acid sequence as set forth in SEQ ID NO: 133; 3) a light chain variable region comprising the amino acid sequence as set forth in SEQ ID NO: 15, and a heavy chain variable region comprising the amino acid sequence as set forth in SEQ ID NO: 14; 4) a light chain variable region comprising the amino acid sequence as set forth in SEQ ID NO: 18, and a heavy chain variable region comprising the amino acid sequence as set forth in SEQ ID NO: 16; 5) a light chain variable region comprising the amino acid sequence as set forth in SEQ ID NO: 90, and a heavy chain variable region comprising the amino acid sequence as set forth in SEQ ID NO: 89; 6) a light chain variable region comprising the amino acid sequence as set forth in SEQ ID NO: 91, and a heavy chain variable region comprising the amino acid sequence as set forth in SEQ ID NO: 86; 7) a light chain variable region comprising the amino acid sequence as set forth in SEQ ID NO: 91, and a heavy chain variable region comprising the amino acid sequence as set forth in SEQ ID NO: 92; 8) a light chain variable region comprising the amino acid sequence as set forth in SEQ ID NO: 61, and a heavy chain variable region comprising the amino acid sequence as set forth in SEQ ID NO: 70; 9) a light chain variable region comprising the amino acid sequence as set forth in SEQ ID NO: 61, and a heavy chain variable region comprising the amino acid sequence as set forth in SEQ ID NO: 74; 10) a light chain variable region comprising the amino acid sequence as set forth in SEQ ID NO: 61, and a heavy chain variable region comprising the amino acid sequence as set forth in SEQ ID NO: 76; 11) a light chain variable region comprising the amino acid sequence as set forth in SEQ ID NO: 78, and a heavy chain variable region comprising the amino acid sequence as set forth in SEQ ID NO: 70; 12) a light chain variable region comprising the amino acid sequence as set forth in SEQ ID NO: 78, and a heavy chain variable region comprising the amino acid sequence as set forth in SEQ ID NO: 74; 13) a light chain variable region comprising the amino acid sequence as set forth in SEQ ID NO: 78, and a heavy chain variable region comprising the amino acid sequence as set forth in SEQ ID NO: 76; 14) a light chain variable region comprising the amino acid sequence as set forth in SEQ ID NO: 85, and a heavy chain variable region comprising the amino acid sequence as set forth in SEQ ID NO: 84; 15) a light chain variable region comprising the amino acid sequence as set forth in SEQ ID NO: 44, and a heavy chain variable region comprising the amino acid sequence as set forth in SEQ ID NO: 42; 16) a light chain variable region comprising the amino acid sequence as set forth in SEQ ID NO: 100, and a heavy chain variable region comprising the amino acid sequence as set forth in SEQ ID NO: 99; 17) a light chain variable region comprising the amino acid sequence as set forth in SEQ ID NO: 104, and a heavy chain variable region comprising the amino acid sequence as set forth in SEQ ID NO: 105; 18) a light chain variable region comprising the amino acid sequence as set forth in SEQ ID NO: 104, and a heavy chain variable region comprising the amino acid sequence as set forth in SEQ ID NO: 112; 19) a light chain variable region comprising the amino acid sequence as set forth in SEQ ID NO: 107, and a heavy chain variable region comprising the amino acid sequence as set forth in SEQ ID NO: 106; 20) a light chain variable region comprising the amino acid sequence as set forth in SEQ ID NO: 113, and a heavy chain variable region comprising the amino acid sequence as set forth in SEQ ID NO: 112 or 21) a light chain variable region comprising the amino acid sequence as set forth in SEQ ID NO: 53, and a heavy chain variable region comprising the amino acid sequence as set forth in SEQ ID NO: 51.

The antibody or antigen binding fragment may also encompass a homologue or a variant thereof having substantially the same function/property thereto. In some cases, the homologue or variant may have an amino acid sequence different from that of the antibody or antigen binding fragment of the present disclosure by at least one amino acid. For example, the homologue or variant may be a polypeptide different from the antibody or the antigen binding fragment thereof by an addition, deletion or substitution of one or more amino acid, such as 1-50, 1-40, 1-30, 1-20, 1-15, 1-14, 1-13, 1-12, 1-11, 1-10, 1-9, 1-8, 1-7, 1-6, 1-5, 1-4, 1-3, or 1-2 amino acids. In some cases, the homologue or variant may be a polypeptide having a sequence identity of at least 80% with the antibody or antigen binding fragment thereof. For example, the homologue or variant may be a polypeptide having a sequence identity of 80% (e.g., at least 85%, at least 90%, at least 91%, at least 92%, at least 93%, at least 94%, at least 95%, at least 96%, at least 97%, at least 98%, at least 99% or higher) to the antibody or antigen binding fragment thereof.

The term "percent (%) sequence identity," as used in the context of polypeptide sequences identified herein, generally refers to the percentage of amino acid residues or nucleotides in a query sequence that are identical with the amino acid residues or nucleotides of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid/nucleotide sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide/polynucleotide sequence, or may be measured over a shorter length, for example, over the length of a fragment taken from a larger, defined polypeptide/polynucleotide sequence. It is understood that any fragment length supported by the sequences shown herein, in the tables, figures or Sequence Listing, may be used to describe a length over which percentage identity may be measured.

In some cases, comparing to its parent sequence, in the variant or the homologue of the antibody or its antigen binding fragment, one or more (e.g., 2, 3, 4, or 5) of the following residues or a corresponding residue is not changed or mutated: heavy chain W33 of SEQ ID NO: 86 or a corresponding residue (e.g., the correspondence may be determined via sequence alignment), light chain Y90 of SEQ ID NO: 91 or a corresponding residue, heavy chain H35 of SEQ ID NO: 86 or a corresponding residue, heavy chain W104 of SEQ ID NO: 86 or a corresponding residue, and/or light chain Y31 of SEQ ID NO: 91 or a corresponding residue.

In the present application, the CDR sequences may be classified according to a specific CDR classification standard (for example, the Kabat method). It should be noted that if the amino acid sequence of a TrkA antibody or the antigen binding fragment thereof determined according to a specific CDR classification standard (such as the Kabat method) is the same as the CDR sequence defined in the present application, then the TrkA antibody or the antigen binding fragment thereof is also within the protection scope of the present application. According to different CDR classification standards, the precise identification of CDR positions may be slightly different, and therefore the present application comprises not only the CDRs shown in the sequence listing but also the CDRs comprised in the VH and VL domains using other classification methods for example, Chothia, enhanced Chothia, or IMGT.

In another aspect, the present application provides a fusion protein, comprising the antibody or the antigen binding fragment thereof of the present disclosure.

In another aspect, the present application provides a protein conjugate (such as an immunoconjugate), comprising the antibody or the antigen binding fragment thereof of the present disclosure.

Nucleic Acid, Vector, Cell and Preparation Method

In another aspect, the present disclosure provides isolated nucleic acid or molecules, encoding for the antibody or the antigen binding fragment thereof, or the fusion protein.

The isolated nucleic acids may comprise one or more nucleic acid molecules, with each encoding for at least a part of the antibody of the present disclosure or an antigen binding fragment thereof. For example, the isolated nucleic acids may comprise at least two nucleic acid molecules, with one encoding for the antibody heavy chain or a fragment thereof, and one encoding for the antibody light chain or a fragment thereof. In some cases, the isolated nucleic acids may encode for a fusion protein.

The isolated nucleic acid or isolated nucleic acids may be synthesized using recombinant techniques well known in the art. For example, the isolated nucleic acid or isolated nucleic acids may be synthesized with an automated DNA synthesizer. Standard recombinant DNA and molecular cloning techniques include those described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987). Briefly, the subject nucleic acids may be prepared from genomic DNA fragments, cDNAs, and RNAs, all of which may be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is affected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., Tet. Lett. 521:719 (1980); U.S. Pat. No. 4,500,707 to Caruthers et al.; and U.S. Pat. Nos. 5,436,327 and 5,700,637 to Southern et al.

In another aspect, the present disclosure provides a vector or vectors, comprising the isolated nucleic acid molecule or molecules.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some cases, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

In another aspect, the present disclosure provides a cell (e.g., an isolated cell, such as a host cell), comprising the isolated nucleic acid molecule or molecules of the present disclosure or the vector or vectors of the present disclosure.

The cell may express the antibody, or the antigen binding fragment thereof of the present disclosure, or the fusion protein of the present disclosure. The cell may be a eukaryotic cell or a prokaryotic cell. An appropriate cell may be transformed or transfected with the nucleic acid(s) or vector(s) of the present disclosure and utilized for the expression and/or secretion of the antibody, the antigen binding fragment thereof, or the fusion protein. For example, the cell may be *E. coli* cells, other bacterial host cells, yeast cells, or various higher eukaryotic cells.

In another aspect, the present disclosure provides a method for producing the antibody or the antigen binding fragment thereof, or the fusion protein of the present disclosure, comprising culturing the cell of the present disclosure under conditions enabling expression of the antibody, the antigen binding fragment thereof, or the fusion protein.

The method optionally may further comprise harvesting the antibody or the antigen binding fragment thereof, or the fusion protein of the present disclosure.

Compositions

In another aspect, the present disclosure provides a composition, comprising the antibody or the antigen binding fragment thereof, the fusion protein, the protein conjugate, the isolated nucleic acid molecule or molecules, the vector or vectors, and/or the cell of the present disclosure, and optionally a pharmaceutically acceptable excipient.

In some cases, the pharmaceutically acceptable excipient may comprise a buffer. In some cases, the pharmaceutically acceptable excipient may comprise an amino acid.

In some embodiments, the pH of the composition may be 1-13, for example, the pH may be about 1, 2, 3, 4, 5, 6, 7, 8, 9, 10, 11, 12, or 13.

In some cases, the composition may further comprise an effective amount of an additional therapeutically active component, for example, an additional therapeutically active component for treating a disease or a disorder associated with an inappropriate expression or function of TrkA. Each of the active components may be present in the pharmaceutical composition in a pharmaceutically active amount. In the composition, the antibody, the fragment thereof of the present application may or may not be associated with the additional active component.

Described below are non-limiting exemplary pharmaceutical compositions and methods for preparing the same. The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. In some cases, the pharmaceutical composition may be a liquid pharmaceutical composition.

Pharmaceutical compositions of the disclosure can be presented as discrete dosage forms, with each dosage containing a predetermined amount of an active ingredient as a powder or in granules, a solution, or a suspension in an aqueous or non-aqueous liquid. Such dosage forms can be prepared by any of the methods known to a skilled person, for example, it may include the step of bringing the active ingredient into association with the carrier, which constitutes one or more other ingredients. In general, the compositions are prepared by uniformly and intimately mixing the active ingredient with liquid carriers or finely divided solid carriers or both, and then, if necessary, shaping the product into the desired presentation.

The antibody, the antigen binding fragment thereof, or the fusion protein of the present disclosure can be combined in an intimate admixture with a pharmaceutical carrier according to conventional pharmaceutical compounding techniques. The carrier can take a wide variety of forms depending on the form of preparation desired for administration.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and/or mixtures thereof.

The pharmaceutical compositions of the present disclosure may comprise a therapeutically effective amount of the active agent (e.g., the antibody, the antigen binding fragment thereof, or the fusion protein of the present disclosure). A therapeutically effective amount is an amount of the subject pharmaceutical composition capable of preventing and/or curing (at least partially) a condition or disorder (e.g., a chronic pain) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. It shall be understood that these specific doses may be conveniently adjusted by a skilled person in the art (e.g., a doctor or a pharmacist) based on conditions of a specific patient, formulation, and/or disease.

Medical Use and Methods of Treatment

In another aspect, the present disclosure provides a use of the antibody or the antigen binding fragment thereof, the fusion protein, the protein conjugate, the isolated nucleic acid molecule or molecules, the vector or vectors, and/or the cell of the present disclosure in the manufacture of a medicament for preventing and/or treating a disease or disorder associated with an inappropriate expression or function of TrkA.

In a further aspect, the present application provides a method for preventing and/or treating a disease or disorder in a subject in need thereof, comprising administering to the subject an effective amount of the antibody or the antigen binding fragment the fusion protein, the protein conjugate, the isolated nucleic acid molecule or molecules, the vector or vectors, the cell, and/or the composition of the present disclosure, wherein the disease or disorder is a disease or disorder associated with an inappropriate expression or function of TrkA.

For example, the disease or disorder may comprise pain.

For example, the pain may comprise chronic pain.

For example, the disease or disorder may comprise chronic pain of nociceptive, non-nociceptive, traumatic, inflammatory, neuropathic, proliferative or mixed etiology. For example, the disease or disorder may comprise chronic pain of musculoskeletal or neuropathic origin.

For example, the disease or disorder may comprise post-operative pain, rheumatoid arthritis pain, neuropathic pain and/or osteoarthritis pain.

In other embodiments, the pain is acute or chronic pain that is musculoskeletal or neuropathic in origin. Specific, non-limiting examples of pain that may be prevented and/or treated by the present application includes, for example, post-surgical pain, rheumatoid arthritis pain, neuropathic pain (includes radicular pain CLBP, DNP, and LSR), and osteoarthritis pain (includes non-radicular pain). In some cases, the pain is chronic pain of both musculoskeletal and neuropathic in origin. In other embodiments, the pain is visceral pain (such as, for example, chronic prostatitis, interstitial cystitis or chronic pelvis pain).

For example, such disease or disorder may be pain associated with, but not limited to any of the following: pancreatitis, kidney stones, endometriosis, IBD, Crohn's disease, post-surgical adhesions, gall bladder stones, headaches, dysmenorrhea, musculoskeletal pain, sprains, visceral pain, ovarian cysts, prostatitis, cystitis, interstitial cystitis, post-operative pain, migraine, trigeminal neuralgia, pain from burns and/or wounds, pain associated with trauma, neuropathic pain, pain associated with musculoskeletal diseases, rheumatoid arthritis, osteoarthritis, ankylosing spondylitis, periarticular pathologies, oncological pain, pain from bone metastases, and/or HIV infection.

In another aspect, the present disclosure provides use of the antibody or the antigen binding fragment thereof, the fusion protein, or the protein conjugate in the manufacture of an agent for determining the presence and/or amount of TrkA in a sample.

In another aspect, the present disclosure provides a method for determining the presence and/or amount of TrkA in a sample, comprising: a) contacting the sample with the antibody or the antigen binding fragment, the fusion protein, or the protein conjugate of the present disclosure; and b)

determining the presence and/or amount of the antibody or the antigen binding fragment, of the fusion protein, or of the protein conjugate bound to the sample.

EXAMPLES

The following examples are set forth so as to provide those of ordinary skill in the art with a complete disclosure and description of how to make and use the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1. Generation of Anti-TrkA Monoclonal Antibodies

TrkA Recombinant Protein for Immunization, Binding and Functional Assays

The extracellular domain (ECD) of human TrkA protein (SEQ ID NO: 120) was gene-synthesized, and subcloned in pcDNA3.4-based expression vector with C-terminus fused to a His tag and N-terminus fused to a signal peptide and a flag tag (PHA). The resulted plasmid was transiently transfected into 293-F cells, and cultured for 5-7 days in a $CO_2$ incubator equipped with rotating shaker. The supernatant containing the recombinant protein was collected and cleared by centrifugation, then the protein was purified through one step immobilized metal affinity chromatography. The purified protein was buffer-exchanged into phosphate buffered saline (PBS) and stored in a −80° C. freezer in small aliquots.

Immunization, Hybridoma Fusion and Cloning

One group of BALB/c mice (5 mice/group) were immunized with the purified TrkA ECD protein described above, according to the schedule in Table 3. The TrkA ECD protein was mixed 1:1 with Complete Freund's adjuvant (CFA) or Incomplete Freund's adjuvant (IFA), and a stable oil-in-water emulsion was obtained. CFA was only used with the first immunization. Subsequent immunizations were performed in PBS with IFA. The dose for injection was 25-50 g/200 L/mouse. After immunization, samples of serum were taken to determine the antibody response (titer) to the immunizing antigen by indirect ELISA and FACS (see below). Four days after boosting, the splenocytes were isolated and fused with SP2/0 myeloma cells by the electro cell fusion method to induce the cells to fuse, forming hybridomas. Fused cells were plated into 96-well plates, and 50 plates were used for each fusion.

TABLE 3

Immunization Schedule

| Procedure | Schedule | Route | Dosage |
| --- | --- | --- | --- |
| Pre-Immune Bleed | T = −4 days | N.A. | N.A. |
| Primary Immunization | T = 0 days | s.c. injection | 50 μg PHA/mouse |
| 1$^{st}$Boost | T = 14 days | i.p. injection | 25 μg PHA/mouse |
| Test Bleed 1 | T = 21 days | N.A. | N.A. |
| 2$^{nd}$Boost | T = 28 days | s.c. injection | 25 μg PHA/mouse |

TABLE 3-continued

Immunization Schedule

| Procedure | Schedule | Route | Dosage |
| --- | --- | --- | --- |
| Test Bleed 2 | T = 35 days | N.A. | N.A. |
| Final Boost | T = 56 ± 7 days | i.p. injection | 25 μg PHA/mouse |
| Cell Fusion | T = Final boost + 4 days | | N.A. |

Determine the Binding Activities of the TrkA Antibodies

Hybridoma supernatants were initially screened with human TrkA by indirect ELISA. Briefly, purified PHA was diluted to a final concentration of 1 μg/mL in PBS buffer. 100 μL of the diluted antigen was added to each well of a 96-well plate, and incubated at 4° C. overnight. The plates were washed with PBST (PBS comprising 0.05% Tween-20, pH 7.4) for three times, then 200 μl/well of 2% bovine serum albumin (BSA) diluted in PBST was added and incubated at room temperature for 2 hours for blocking. The blocking solution was removed, and the plate was washed 3 times with 300 μl PBST. The diluted solutions of primary and secondary antibodies, along with substrate solution was prepared. 100 μl of diluted primary antibody was pipetted in each well and was incubated for 1 hour at room temperature. The content in the wells was removed and washed for 3 times with 300 μl PBST buffer. PBS was removed from the plates. 100 μl of diluted Peroxidase-AffiniPure Goat Anti-Mouse IgG was added in each well and incubated for 1 hour at 37° C. The content in the wells was removed and the wells were washed for 3 times with 300 μl PBST. 100 μl of TMB substrate solution was added to the wells. After sufficient color development, 100 μl of stop solution was added to the wells to terminate the reaction. Read the absorbance (OD: 450) of each well with a microplate reader and the data were analyzed.

The ELISA-positive antibody producing clones were further verified by fluorescence-activated cell sorting (FACS) using a conventional method. Briefly, CellSensor® TrkA-NFAT-bla CHO-K1 cells (cells overexpressing human TrkA) were stained with anti-TrkA antibody in U-bottom 96-well plates. The cells were resuspended to $2 \times 10^6$ cells/ml in ice cold PBS. The diluted solutions of primary and secondary antibodies were prepared, and 100 μl of the diluted primary antibody was added in each well, and incubated for 1 hours at 4° C. in the dark. The cells were washed for 2 times by centrifugation at 2500 rpm for 3 min and resuspended in ice cold PBS. The APC Goat anti-Mouse IgG was diluted in cold PBS at the 1 g/ml and then the cells were resuspended in 100 μl of this solution. The cells were washed for 2 times by centrifugation at 2500 rpm for 3 min and resuspended in 100 μl ice cold PBS. The cell suspension was stored immediately at 4° C. in the dark. The cells were analyzed on the flow cytometer as soon as possible.

Subcloning

Hybridomas that showed positive binding in both ELISA and FACS assay were subsequently tested for functional assays to identify antibodies with desired functional activity. The antibodies with positive functional activity were further subcloned by limiting dilution and characterized by FACS and functional assays. The subclones selected through functional assays were defined as monoclonal antibodies. The selected subclones were cultured in the Hybridoma-SFM medium.

Expression and Purification of Monoclonal Antibodies

The positive hybridomas were cultured in the Hybridoma-SFM medium firstly, then the cells were cultured in the Hybridoma-SFM medium at 5% $CO_2$ and 37° C. in an incubator for 4 days. Cell viability yield and protein production were assessed after culturing.

The heavy chain and light chain variable region sequence of the antibody to be expressed were inserted into pCDNA3.4-hIgG4 or pCDNA3.4-hKappa vector respectively. The resulting vector plasmids were extracted and validated by sequencing. The validated plasmids were transfected into human 293F cells with PEI and cultured continuously. The 293F cells were cultured in serum-free medium (Shanghai opmbiosciences, OPM-293CD03) to logarithmic growth phase for cell transfection. 3 g of the antibody light chain plasmid and 2 g of the antibody heavy chain plasmid were dissolved in 1 ml of Opti-MEM® I Reduced Serum Medium (GIBCO, 31985-070), mixed well, added 20 g of PEI, mixed well, incubated for 15 min at RT, and added into 5 mL of cells. Cell culture conditions were as follows: 5% $CO_2$, 37° C., 125 rpm/min. The feeder medium was replenished on day 1. The cells were cultured for another 4 days.

All cells were collected and was spined down at 4000 rpm, 30 min at 4° C. Supernatant containing antibody was collected. Purification of the antibody was performed using GenScript Protein A MagBeads according to the manufacturer's introduction. Briefly, 1) Binding. The clarified supernatant containing antibody of interest was incubated with the MagBeads at room temperature for 2 hours. 2) Washing. Magnetic separation rack was used to collect the beads and discard the supernatant. 1 ml PBS buffer was added to the tube and mixed well, the magnetic separation rack was used to collect the beads and discard the supernatant. The wash step was repeated for three or more times. 3) Elution. 100 μl Elution Buffer (0.1 M glycine, pH 3.0) was added to the tube and mixed well. Incubated for five minutes at room temperature with occasional mixing. The magnetic separation rack was used to collect the beads and transfer the supernatant that contains the eluted IgG into a clean tube. 10 μl of Neutralization Buffer (1 M Tris, pH 8.5) was added to each 100 μl eluate to neutralize the pH. Protein concentrations were determined by measuring absorbance at 280 nm, and the purified antibodies were stored in aliquots in a –80° C. freezer. Three control antibodies, Anti-TNP (with a VH and VL as set forth in SEQ ID NOs: 125 and 126 respectively), Tanezumab (with a VH and VL as set forth in SEQ ID NOs: 127 and 128 respectively) and Fasinumab (with a VH and VL as set forth in SEQ ID NOs: 129 and 130 respectively) were also prepared by the above methods.

Antagonistic Effect to TrkA Activation Using NFAT Reporter Assay

CellSensor® TrkA-NFAT-bla CHO-K1 cells (K1516, Life Technologies) contain a beta-lactamase reporter gene under the control of the NFAT Response Element that has been stably integrated into CHO-K1 cells, which also stably express the human TrkA gene. Therefore, once the cells were stimulated with nerve growth factor 2.5 s (NGF 2.5s), TrkA signaling can be activated, which can be detected with a special fluorescent substrate of beta-lactamase. Using this cell line, the samples can be tested for their antagonist effect to the NGF-TrkA signaling pathway. According to the Invitrogen cellsensor_TrkA NFAT bla_CHOK1_manual, Cellsensor TrkA-NFAT-bla CHO-Klcells (K1516, Life Technologies) were seeded in 384-well plates with 32 μl media on the day before the experiment. The cells were pre-incubated with 3-fold serial diluted antibody in a humidified 37° C./5% $CO_2$ incubator for 30 minutes. Then 4 μl of 11×EC80 stock solution of NGF was added. The antagonist assay plate was incubated in a humidified 37° C./5% $CO_2$ incubator for 5 hours. 6× LiveBLAzer™-FRET B/G Substrate (CCF4-AM) mixture was prepared according to the manufacture's introduction. 8 μl of 6× Substrate Mixture was added to each well. The plate was covered to be protected from light and evaporation and was incubated at room temperature for 2 hours. Cell-free wells were used as the background. FRET signals (405 nm excitation, 460 nm & 530 nm emission) were obtained from the microplate reader (C5, Biotek) and background signals were subtracted. The ratio of fluorescent signals at 460 nm to 530 nm reflected the level of TrkA activation.

Example 2. Development of TrkA Antagonistic Monoclonal Antibodies

Figure 2:
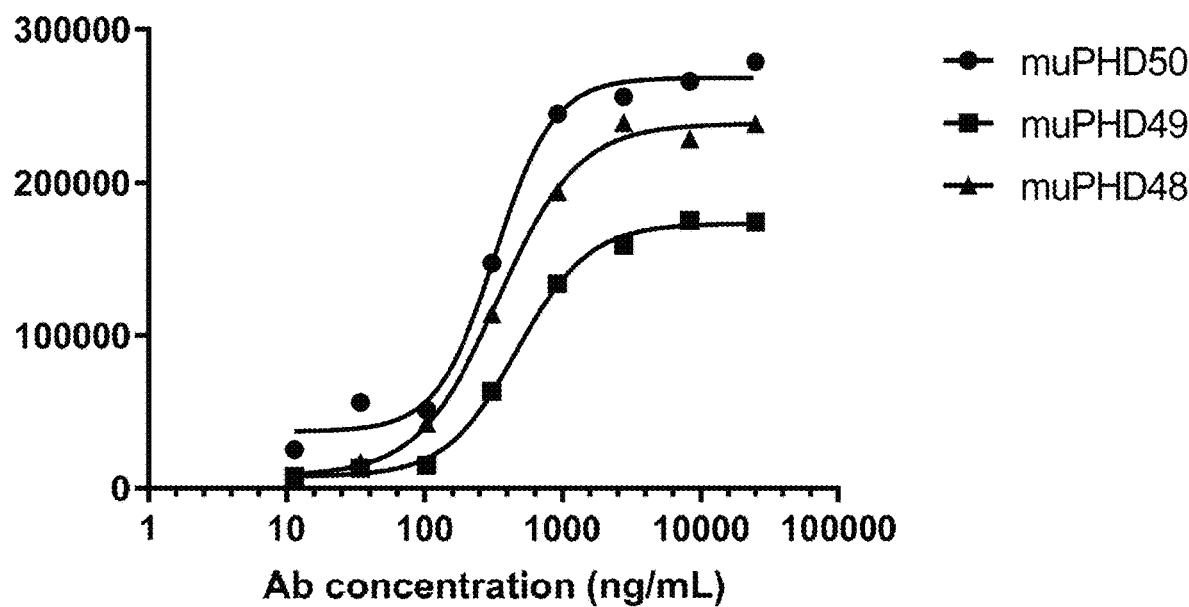
FIG. 2 illustrates the results of FACS binding analysis of exemplary antibodies of the present disclosure.
Figure 3A:
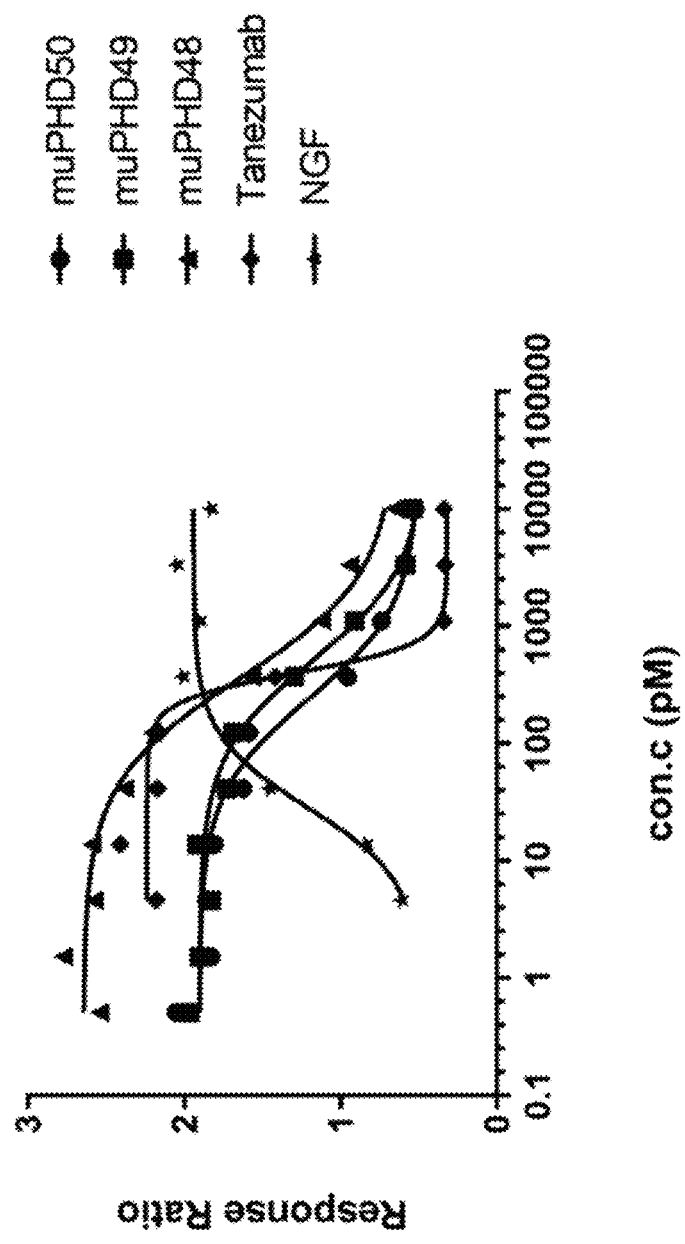
FIG. 3A-3B illustrate the results of NFAT functional analysis of exemplary antibodies of the present disclosure.
Figure 3B:
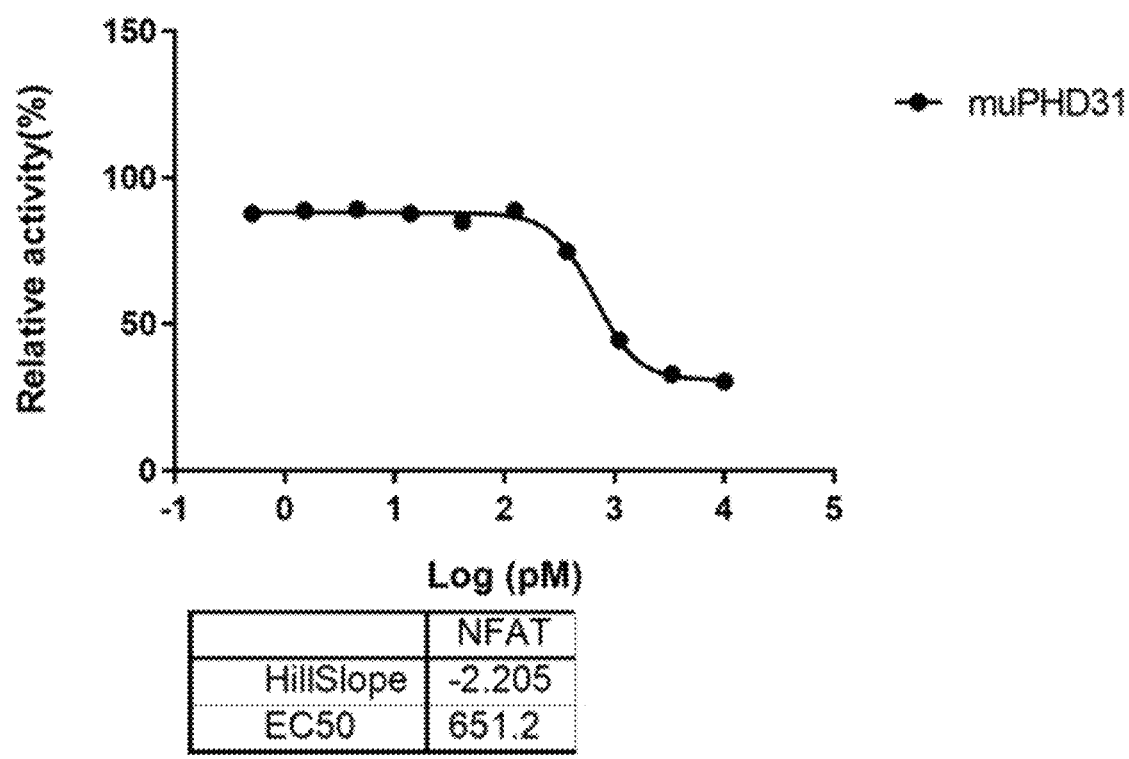

After screening, desired clones were sub-cloned and identified, which bound to human TrkA with high specificity and strength, and also showed a strong inhibition in TrkA dependent NFAT antagonist reporter assay. As shown by the ELISA assay result (FIG. 1) and FACS analysis results (FIG. 2), the selected clones muPHD50, muPHD48 and muPHD49 exhibited desired binding to human TrkA. Furthermore, as shown in the antagonist NFAT assay (FIGS. 3A and 3B), the selected antibodies muPHD31, muPHD50, muPHD48 and muPHD49 could inhibit the activation of the TrkA signaling induced by human NGF.

Example 3. Cloning the Antibody Variable Region Gene

Hybridoma cells were cultured in a 10 cm dish and were collected at logarithmic growth phase. Total cell RNA was extracted with Trizol (Invitrogen, 15596-018) following the manufacturer's introduction. The RNA was resuspended in nuclease free water. The RNA concentration was determined using absorbance at 260 nm on the bioTEK equipment. To obtain the cDNA templates, 4 pg of each RNA was reverse transcribed using HiFiScript cDNA Synthesis Kit (CWBIO, CW2569). Then two rounds of PCR reaction were performed to clone the variable gene of the antibodies. The PCR product was directly sequenced. To construct expression plasmid of the chimeric antibody, the VH gene was subcloned into a pCNDA3.4-hIgG4 vector, and the VL gene was subcloned into a pCDNA3.4-hKappa vector, the sequences were further confirmed by DNA sequencing. The complementarity determining regions (CDRs) of the antibodies were identified according to Kabat, Enhanced Chothia and IMGT system (Dunbar J et al Bioinformatics. 2016; 32(2):298-300).

The heavy chain and light chain variable region sequences of muPHD48 is as set forth in SEQ ID NOs: 16 and 18, respectively.

The CDRs of muPHD48 are as follows:

| CDR Classification | CDR | Sequence | SEQ ID NO: |
|---|---|---|---|
| Kabat | HCDR1 | TYWMH | 20 |
| | HCDR2 | TIYPGNSDSSNNQKFKG | 23 |
| | HCDR3 | FYYEDWYFDV | 26 |
| | LCDR1 | SASSSVSYMY | 28 |
| | LCDR2 | RTSNLAS | 30 |
| | LCDR3 | QQYHSYPPT | 32 |
| Enhanced Chothia | HCDR1 | GYSFTTYWMH | 21 |
| | HCDR2 | TIYPGNSDSS | 24 |
| | HCDR3 | FYYEDWYFDV | 26 |
| | LCDR1 | SASSSVSYMY | 28 |
| | LCDR2 | RTSNLAS | 30 |
| | LCDR3 | QQYHSYPPT | 32 |

| CDR Classification | CDR | Sequence | SEQ ID NO: |
|---|---|---|---|
| IMGT | HCDR1 | GYSFTTYW | 22 |
| | HCDR2 | IYPGNSDS | 25 |
| | HCDR3 | TRFYYEDWYFDV | 27 |
| | LCDR1 | SSVSY | 29 |
| | LCDR2 | RTS | 31 |
| | LCDR3 | QQYHSYPPT | 32 |

The heavy chain and light chain variable region sequences of muPHID49 is as set forth in SEQ ID NOs: 42 and 44, respectively.

The CDRs of muPHID49 are as follows:

| CDR Classification | CDR | Sequence | SEQ ID NO: |
|---|---|---|---|
| Kabat | HCDR1 | SYWMQ | 45 |
| | HCDR2 | AIYPGDDDTIYTQKFKG | 46 |
| | HCDR3 | NYDYQAWFAY | 37 |
| | LCDR1 | SASSSVSYMY | 28 |
| | LCDR2 | LTSNLAS | 39 |
| | LCDR3 | QQWSSNPLT | 41 |
| Enhanced Chothia | HCDR1 | GYTFSSYWMQ | 33 |
| | HCDR2 | AIYPGDDDTI | 35 |
| | HCDR3 | NYDYQAWFAY | 37 |
| | LCDR1 | SASSSVSYMY | 28 |
| | LCDR2 | LTSNLAS | 39 |
| | LCDR3 | QQWSSNPLT | 41 |
| IMGT | HCDR1 | GYTFSSYW | 34 |
| | HCDR2 | IYPGDDDT | 36 |
| | HCDR3 | ARNYDYQAWFAY | 38 |
| | LCDR1 | SSVSY | 29 |
| | LCDR2 | LTS | 40 |
| | LCDR3 | QQWSSNPLT | 41 |

The heavy chain and light chain variable region sequences of muPHID50 is as set forth in SEQ ID NOs: 51 and 53, respectively.

The CDRs of muPHID50 are as follows:

| CDR Classification | CDR | Sequence | SEQ ID NO: |
|---|---|---|---|
| Kabat | HCDR1 | SYWMH | 47 |
| | HCDR2 | AIYPGDSDTNYNQKFKG | 48 |
| | HCDR3 | YGNYAGYYHMDY | 49 |
| | LCDR1 | SASSSVSYIY | 50 |
| | LCDR2 | LTSNLAS | 39 |
| | LCDR3 | QQWSSNPLT | 41 |

The heavy chain and light chain variable region sequences of muPHID31 is as set forth in SEQ ID NOs: 14 and 15, respectively.

The CDRs of muPHID31 are as follows:

| CDR Classification | CDR | Sequence | SEQ ID NO: |
|---|---|---|---|
| Kabat | HCDR1 | SYGVH | 1 |
| | HCDR2 | VIWSGGSTDYNAAFIS | 4 |
| | HCDR3 | NNWDPWAMDY | 7 |
| | LCDR1 | RSSTGAVTTSNYAN | 9 |
| | LCDR2 | GTNNRAP | 11 |
| | LCDR3 | ALWYSNHWV | 13 |
| Enhanced Chothia | HCDR1 | GFSLTSYGVH | 2 |
| | HCDR2 | VIWSGGSTD | 5 |
| | HCDR3 | NNWDPWAMDY | 7 |
| | LCDRl | RSSTGAVTTSNYAN | 9 |
| | LCDR2 | GTNNRAP | 11 |
| | LCDR3 | ALWYSNHWV | 13 |
| IMGT | HCDR1 | GFSLTSYG | 3 |
| | HCDR2 | IWSGGST | 6 |
| | HCDR3 | ARNNWDPWAMDY | 8 |
| | LCDR1 | TGAVTTSNY | 10 |
| | LCDR2 | GT | 12 |
| | LCDR3 | ALWYSNHWV | 13 |

Example 4. Humanization

Humanization of murine antibodies was carried out using CDR grafting, as previously reported. Briefly, the parental (murine antibody) variable region (VH and VL) frameworks were replaced with those of the selected human germline V and J genes of VH and VL. The germline genes were selected on the basis of the homology between the parental antibody and the germline V and J genes. Human HC germline genes IGHV1-46*01 and IGHJ3*01 were selected as FR donors for the humanization of muPHD48 VH; Human LC germline genes IGKV1-39*01 and IGKJ4*01 were selected as FR donors for the humanization of muPHD48 VL. Human HC germline genes IGHV1-69*01 and IGHJ5*01 were selected as FR donors for the humanization of muPHD49 VH; Human LC germline genes IGKV1-39*01 and IGKJ2*01 were selected as FR donors for the humanization of muPHD49 VL.

The VH and VL sequences of the humanized muPHD48 (i.e. PHD48-01) are as below:

VH of PHD48-01
(SEQ ID NO: 89)
QVQLVQSGAEVKKPGASVKVSCKASGYSFTTYWMHWVRQAPGQGLEWIG
TIYPGNSDSSNNQKFKGRATLTADTSTSTAYMELSSLRSEDTAVYYCTR
FYYEDWYFDVWGQGTMVTVSS

VL of PHD48-01
(SEQ ID NO: 90)
DIQMTQSPSSLSASVGDRVTITCSASSSVSYMYWFQQKPGKAPKPWIYR
TSNLASGVPSRFSGSGSGTDYTLTISSLQPEDFATYYCQQYHSYPPTFG
GGTKVEIK

The VH and VL sequences of the humanized muPHD49 (i.e. PHD49-01) are as below:

VH of PHD49-01
(SEQ ID NO: 99)
QVQLVQSGAEVKKPGSSVKVSCKASGYTFSSYWMQWVRQAPGQGLEWIG
AIYPGDDDTIYTQKFKGRATLTADKSTSTAYMELSSLRSEDTAVYYCAR
NYDYQAWFAYWGQGTLVTVSS

VL of PHD49-01
(SEQ ID NO: 100)
DIQMTQSPSSLSASVGDRVTITCSASSSVSYMYWYQQKPGKAPKPWIYL
TSNLASGVPSRFSGSGSGTDYTLTISSLQPEDFATYYCQQWSSNPLTFG
QGTKLEIK

The corresponding encoding nucleic acid sequences were synthesized and subcloned into a pCDNA3.4-hIgG4 or pCDNA3.4-hKappa vector, respectively, and subsequently sequenced (GeneWiz). The expression plasmids for PHD48-01 and PHD49-01 comprises the humanized VH fused to human IgG4 constant region and the humanized VL fused to human Ig kappa constant region. All recombinant antibodies were expressed and purified as described in Example 1.

Figure 4A:
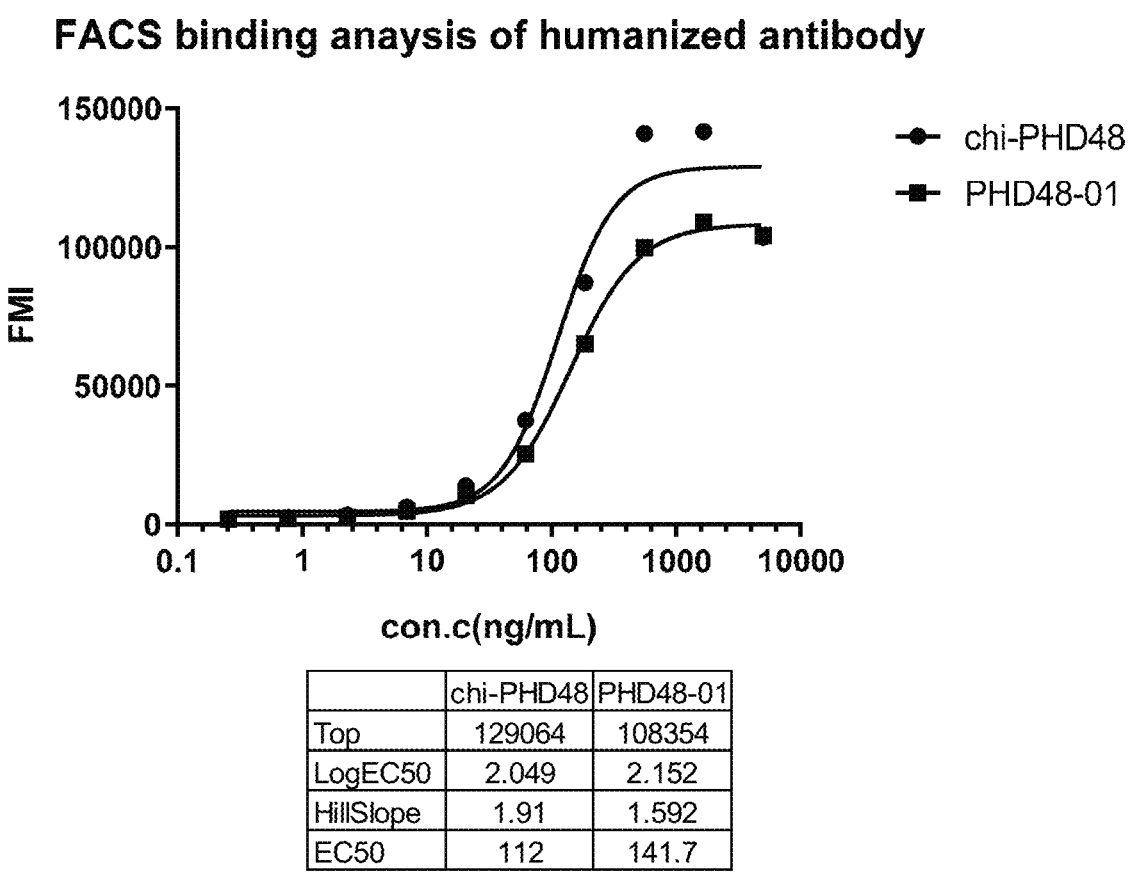
FIG. 4A-4B illustrate the binding and functional properties of exemplary antibodies of the present disclosure.
Figure 4B:
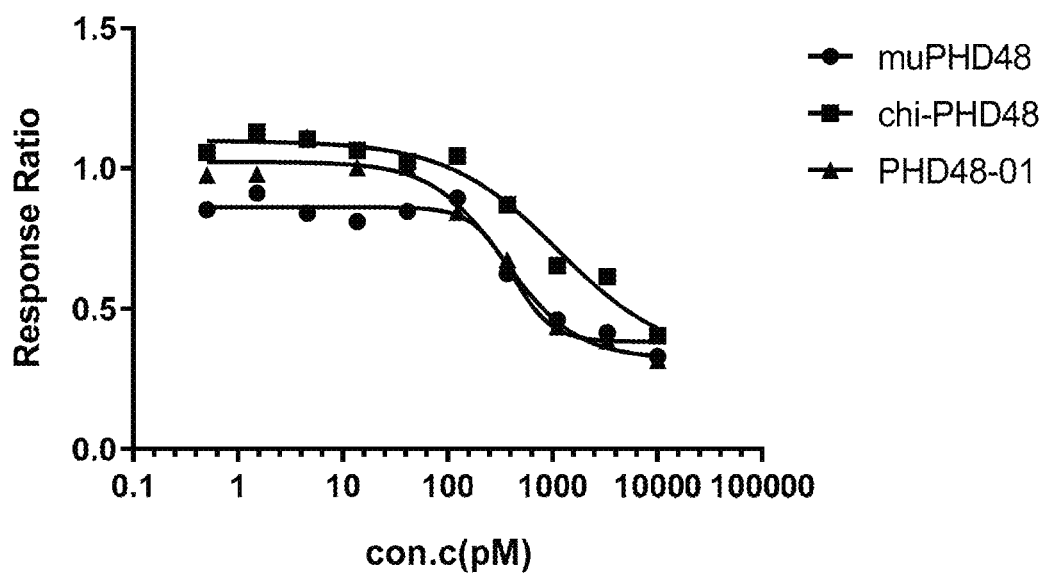

As shown in the FIGS. 4A and 4B, the EC50 value of PHD48-01 in FACS analysis was about 142 ng/mL, comparable to 112 ng/ml of chi-PHD48 (the chimeric antibody derived from muPHD48) and the IC50 value of PHD48-01 in NFAT antagonistic assay was about 345 pM, comparable to muPHD48 (411 pM). These results suggest that PHD48-01 fully retained the binding and biological activity of muPHD48 and chi-PHD48.

Figure 5A:
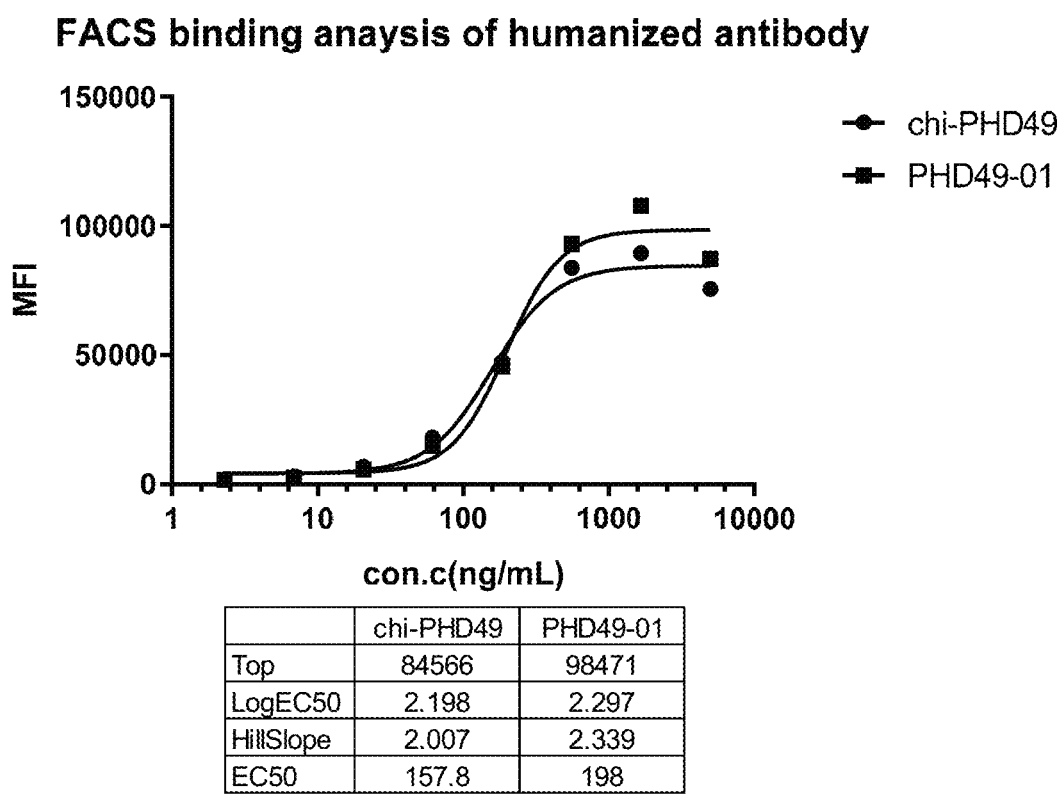
FIG. 5A-5B illustrate the binding and functional properties of exemplary antibodies of the present disclosure.
Figure 5B:
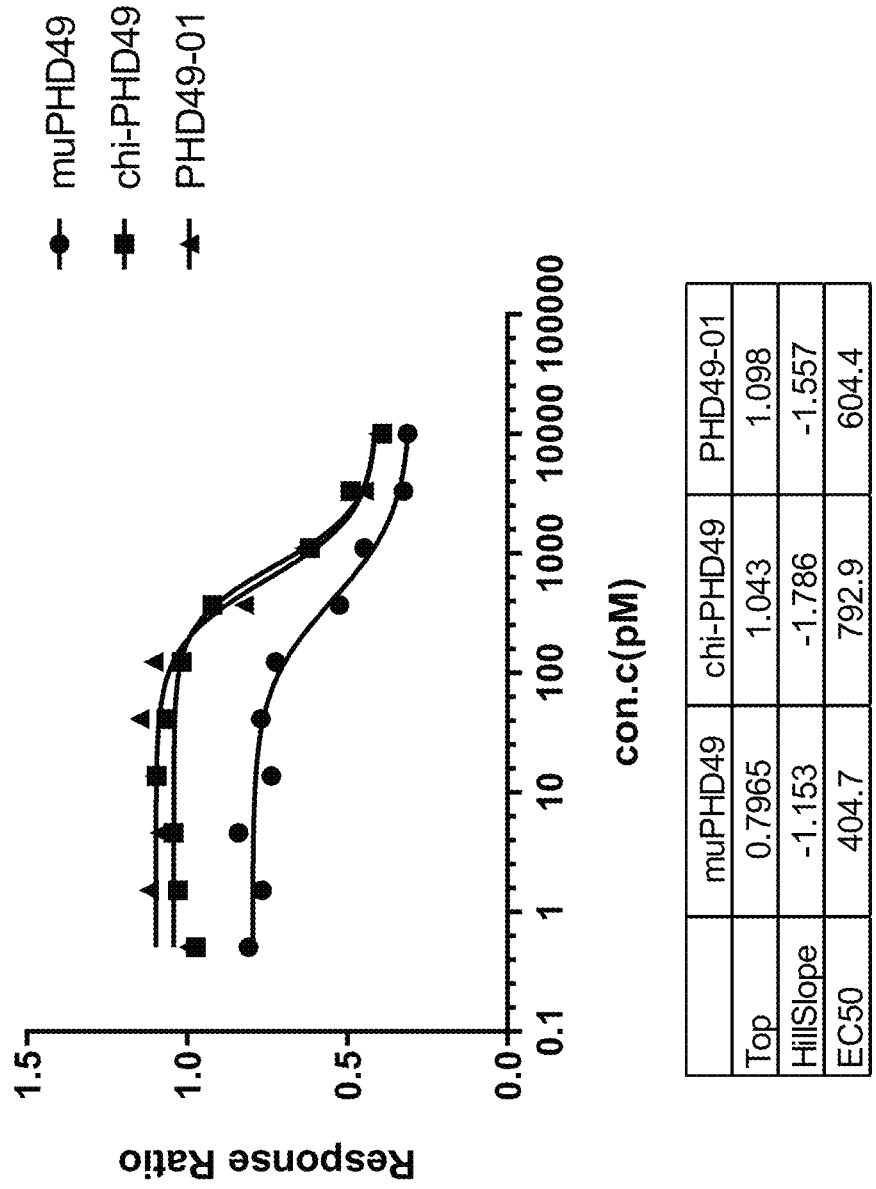

As shown in the FIGS. 5A and 5B, PHD49-01 also retained similar functions as chi-PHD49. The EC50 value of PHD49-01 in FACS analysis was about 198 ng/mL, comparable to 157 ng/mL of chi-PHD49. The IC50 value of PHD49-01 in NFAT assay was about 604 pM, comparable to that of muPHD49 (404 pM).

The bio-layer interferometry (BLI) method was used to determine the affinities of the antibodies, employing Octet Red384. Briefly, anti-human Fc-coated biosensor AHQ tips (ForteBio) were put into PBS with 0.1% w/v bovine serum albumin and 0.05% Tween-20 for a minimum of 10 min in the pre-wetting plate. The purified antibodies (100 nM in PBS with 0.1% bovine serum albumin and 0.05% Tween-20 (assay buffer)) were captured on AHQ biosensors (ForteBio) at a level of about 1 nm. The loaded biosensors were washed with an assay buffer to remove any unbound protein. Then, the association rates, dissociation rates and response were measured, using an antigen of 100 nM (in PBS with 0.1% bovine serum albumin and 0.05% Tween-20). The results are shown in the table below:

| Sample ID | $K_D$ (M) | $K_{on}$(1/Ms) | $K_{off}$(1/s) | VH SEQ ID NO. | VL SEQ ID NO. |
|---|---|---|---|---|---|
| PHD48-01 | 3.07E−09 | 2.07E+05 | 6.34E−04 | 89 | 90 |
| chi-PHD48 | 5.33E−09 | 2.14E+05 | 1.14E−03 | 16 | 18 |
| chi-PHD49 | 1.79E−09 | 3.37E+05 | 6.03E−04 | 42 | 44 |
| PHD49-01 | 4.84E−09 | 2.03E+05 | 9.80E−04 | 99 | 100 |

The PHD48-01 antibody had similar affinity as the chimeric antibody. While the PHD49-01 antibody had a lower affinity but comparable to that of the chimeric antibody, indicated by the $K_D$ value.

Two rounds of humanizations were further performed. In the first round, less murine amino acid residues were mutated while retaining high affinity comparable to their chimeric antibodies. In the second round, many other variants were further constructed (including several mutations in the CDR sequences). Quickchange based site-directed mutagenesis or overlap PCR were performed to create expression plasmid of new versions of $2^{nd}$ round humanized antibodies. All recombinant antibodies were expressed and purified as described in Example 1, then measured antigen binding affinity using BLI technology with the Octet Red384 instrument as mentioned above. To compare the functional activity of humanized antibodies with chimeric antibodies, NFAT assay was also performed. The results were summarized in the table below.

| Sample ID | $K_D$ (M) | $K_{on}$(1/Ms) | $K_{off}$(1/s) | VH SEQ ID No. | VL SEQ ID No. |
|---|---|---|---|---|---|
| chi-PHD48 | 2.80E−09 | 2.72E+05 | 7.61E−04 | 16 | 18 |
| PHD48-01 | 3.07E−09 | 2.07E+05 | 6.34E−04 | 89 | 90 |
| PHD48-08 | 1.38E−09 | 2.40E+05 | 3.31E−04 | 92 | 91 |
| chi-PHD49 | 3.62E−09 | 2.29E+05 | 8.27E−04 | 42 | 44 |
| PHD49-11 | 1.06E−08 | 1.96E+05 | 2.07E−03 | 106 | 107 |

Example 5. Affinity Maturation

Antibody affinity maturation was carried out by phage display as reported previously (Thie H et. al Methods Mol Biol. 2009; 525:309-xv, Bostrom J et al. Methods Mol Biol. 2009; 525:353-xiii). Random mutations were inserted by error-prone PCR using GeneMorph II Random Mutagenesis Kit (Stratagene) according to the manufacturer's instructions. Mutated PCR products and phage-display vectors were digested by NcoI-HF(NEB) and EcoRI(NEB) at 37° C. overnight. Fully digested DNA was purified using Axygen® AxyPrep PCR Clean-Up Kit and the respective DNA concentrations of vector and PCR products were determined by measuring absorbance at 260 nm. Next, ligation was performed in a 500 µl volume with a vector: insert molar ratio of 1:3 and incubated at 16° C. overnight. After that, the ligated product was desalted using Axygen® AxyPrep PCR Clean-Up Kit and introduced into XL1-blue electrocompetent cells. The transformed cell was recovered in 15 ml pre-warmed 2×YT medium for 2 h at 37° C. and 250 rpm. Transformation efficiency was calculated by plating an aliquot of each dilution after overnight incubation at 30° C. The rest of the cell suspension was plated to 15×15 cm 2×YT agar plates. Next day, cells from the plate were carefully scraped using a spatula. High-affinity clones were selected and sequenced.

The affinity of the antibodies is summarized in the table below:

| Sample ID | $K_D$ (M) | $K_{on}$(1/Ms) | $K_{off}$(1/s) | VH SEQ ID NO | VL SEQ ID NO |
|---|---|---|---|---|---|
| chi-PHD49 | 3.04E−09 | 2.19E+05 | 6.65E−04 | 42 | 44 |
| PHD49-05 | 5.83E−10 | 2.99E+05 | 1.74E−04 | 105 | 104 |
| PHD49-21 | 2.59E−10 | 3.67E+05 | 9.51E−05 | 112 | 113 |
| PHD49 | 1.74E−10 | 3.00E+05 | 5.21E−05 | 112 | 104 |

Example 6. Affinity Determinations by Surface Plasmon Resonance (SPR)

The binding kinetics and affinities of the humanized antibodies were determined using a BIAcoreT200™ SPR system. Approximately 30 RU of the humanized antibody was immobilized on a protein G sensor chip and serial 2-fold dilutions of the PHA (0.625-20 nM) in 1×HBS-EP+ buffer were injected over the antibody-bound surface at a flow rate of 30 µl/min. The results are summarized below:

| Sample ID | $K_{on}$(1/Ms) | $K_{off}$(1/s) | $K_D$ (M) | VH SEQ ID NO | VL SEQ ID NO |
|---|---|---|---|---|---|
| chi-PHD48 | $1.701 \times 10^5$ | $6.904 \times 10^{-4}$ | $4.058 \times 10^{-9}$ | 16 | 18 |
| PHD48-01 | $2.243 \times 10^5$ | $5.241 \times 10^{-4}$ | $2.336 \times 10^{-9}$ | 89 | 90 |

| Sample ID | $K_{on}$(1/Ms) | $K_{off}$(1/s) | $K_D$ (M) | VH SEQ ID NO | VL SEQ ID NO |
|---|---|---|---|---|---|
| PHD48-08 | $1.627 \times 10^5$ | $4.503 \times 10^{-4}$ | $2.768 \times 10^{-9}$ | 92 | 91 |
| PHD48 | $2.204 \times 10^5$ | $4.131 \times 10^{-4}$ | $1.874 \times 10^{-9}$ | 86 | 91 |

Example 7. In Vitro Functional Analysis of the TrkA Antibodies

To evaluate the activities of the humanized TrkA antibodies of the present disclosure, the inhibition of NGF induced TrkA activation was assessed using CellSensor® TrkA-NFAT-bla CHO-K1 cells. Cellsensor TrkA-NFAT-bla CHO-K1 cells (K1516, Life Technologies) were seeded in 96-well plates with 100 μl media on the day before the experiment. The cells were pre-incubated with 3-fold serial diluted antibody in a humidified 37° C./5% $CO_2$ incubator for 30 minutes. Then cell supernatant was removed and 50 μl/well of 2×NGF was added. The plates were incubated in a 37° C./5% $CO_2$ incubator for 30 minutes. Cell supernatant was removed carefully either by aspirating supernatant or by flicking the plate. 50 μl of supplemented lysis buffer (1×) was added immediately and incubated for 30 minutes at room temperature while shaking. After homogenization by pipetting up and down, 16 μl cell lysate was transferred from the 96-well plate to a 384-well plate. 16 μl of supplemented lysis buffer (1×) was dispensed to the Cell-free Control wells. 16 μl of homogenized cell lysate was dispensed to the Test Sample wells, the Unstimulated Control wells, and Stimulated Control wells were incubated for at least 4 hours at room temperature. The reader for $Eu^{3+}$ Cryptate was set up and the fluorescence emission at two different wavelengths (665 nm and 620 nm) was read on a compatible HTRF® reader. NGF dose response curve was analyzed with Four-Parameter Fit using GraphPad Prism software. The results are summarized in the table below.

| Sample ID | NFAT IC50 (nM) | VH SEQ ID NO. | VL SEQ ID NO. |
|---|---|---|---|
| PHD48-08 | 187.5 | 92 | 91 |
| PHD48 | 66.53 | 86 | 91 |
| PHD49-11 | 268.8 | 106 | 107 |
| PHD49-05 | 170.4 | 105 | 104 |
| PHD49-21 | 123.9 | 112 | 113 |
| PHD49 | 266.1 | 112 | 104 |

Example 8. Determining the Binding Epitope of the Anti-TrkA Antibodies

The full-length PHD48 antibody was digested at 37° C. for 240 mins by pepsin with a molar ratio of 1:200 (Pepsin: Antibody protein). A final concentration of 50 mM 2-mercaptoethylamine HCl (2-MEA) was added to the sample and the sample was incubated at 37° C. for 30 mins. PHD48 Fab was then purified by size exclusion column. TrkA (ECD)-PHD48 Fab-Anti human Fab VHH (molar ratio 1:2:6) was prepared by incubating the three components on ice for 2 hours.

Cryo-EM data were collected with a 300 kV Titan Krios electron microscope (Thermo Fisher Scientific, USA) equipped with a K3 direct electron detector (Gatan, USA) operating in a counting mode. All movies were automatically recorded using EPU at a magnification of 105K, with a physical pixel size of 0.819 Å. A total dose of 55.8 e-/Å2 was fractionated into 40 frames. All image processing was performed using cryoSPARC v3.3.1.Patch CTF estimation, 2D classification, heterogeneous refinement and homogeneous refinements were all performed in cryoSPARC. A total of 61,777,707 particles were auto-picked using a template picker and extracted with 2×2 binning (180-pixel box size, 1.638 Å per pixel). Two rounds of 2D classification were performed to select data set of good particles. Then these selected particles were subjected to heterogeneous refinement. The refined coordinates were used for re-centering and re-extraction of unbinned particles (0.819 Å per pixel, 360-pixel box size). These particles were subjected to further homogeneous refinements and the final density map was 3.11 Å.

To build the model of TrkA (ECD)—PHD48 Fab-Anti human Fab VHH complex, the structure of TrkA (ECD) (from AlphaFold PDB) and PHD48 Fab (from PDB 6WW2 removed Frizzled-5 protein) was fitted into the cryo-EM map using UCSF Chimera (UCSF Chimera Home Page). The model was manually built in Coot (Emsley et al., 2010) with the guidance of the cryo-EM map, and in combination with real space refinement using CCPEM.

Figure 6:
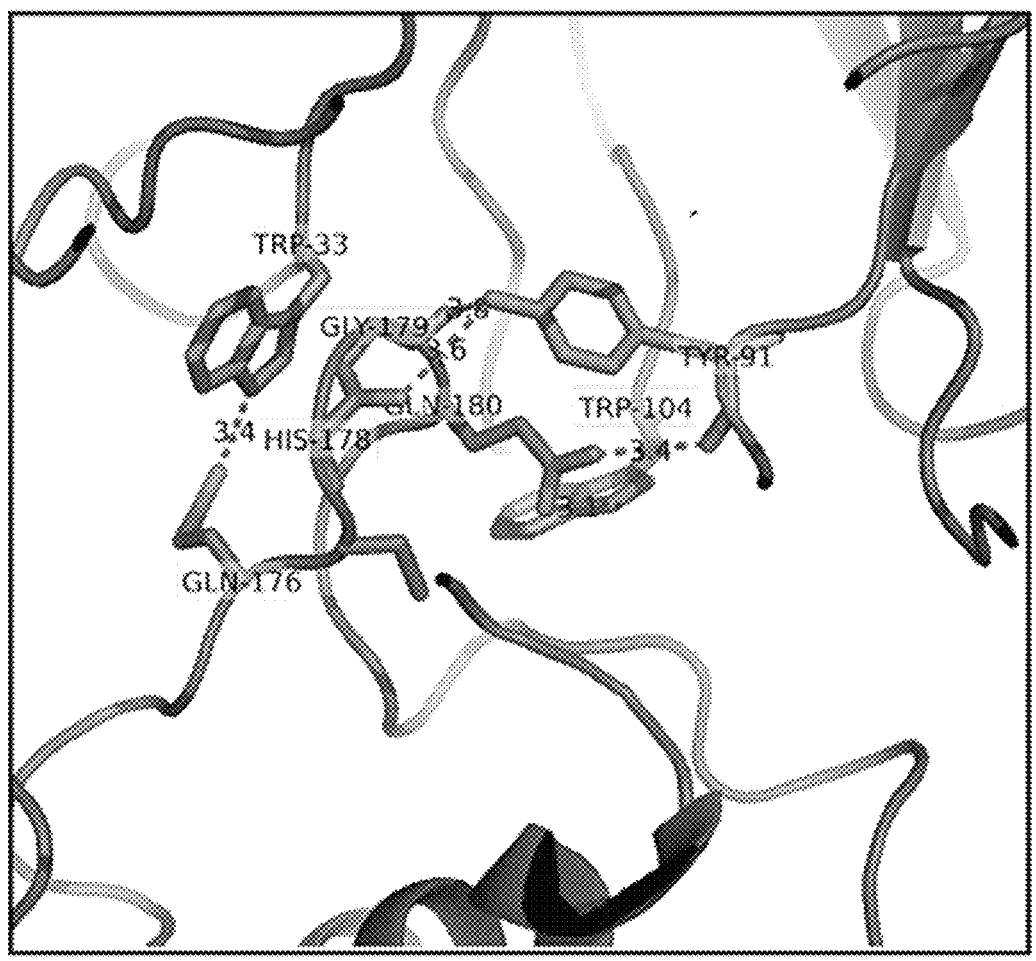
FIG. 6 illustrates the epitope analysis for TrkA(ECD) and an exemplary antibody of the present disclosure.

The interaction between TrkA (ECD) and PHD48 was analyzed by UCSF Chimera. As shown in FIG. 6. The antigen-antibody interaction is mainly mediated by hydrogen bonds and the interaction regions are at residues 176 (Q), 178~180 (HGQ), and 187 (P) of the TrkA (ECD), residues 33 (W), 35 (H) and 104 (W) of the PHD48 heavy chain (its VH has the amino acid sequence as set forth in SEQ ID NO: 86), residue 31 (Y) and 90 (Y) of the PHD48 light chain (its VL has the amino acid sequence as set forth in SEQ ID NO: 91, Y31 corresponds to Y32 according to the Kabat numbering system in FIG. 6, and Y90 corresponds to Y91 according to the Kabat numbering system in FIG. 6). The interaction residue sites are shown in the following table:

| Antigen | Antigen atom | Interaction site | Distance (Å) |
|---|---|---|---|
| TrkA (ECD) | 176(GLN) | Heavy chain 33(TRP) | 3.36 |
|  | 178(HIS) | Light chain 90(TYR) | 3.62 |
|  | 179(GLY) | Heavy chain 35(HIS) | 2.68 |
|  | 179(GLY) | Light chain 90(TYR) | 3.76 |
|  | 180(GLN) | Heavy chain 104(TRP) | 3.06 |
|  | 180(GLN) | Light chain 90(TYR) | 3.43 |
|  | 187(PRO) | Light chain 31(TYR) | 3.13 |

Example 9. Determining the Affinity and Functions of TrkA Antibody Variants

The affinity of additional TrkA antibody variants was determined by bio-layer interferometry (BLI)-based method (Fortebio). All the antibody variants were prepared as described in Example 1 and Example 4 above.

The amino acid sequences of TrkA antibody variants are shown below:

| Antibody | VL (SEQ ID NO) | VH (SEQ ID NO) |
|---|---|---|
| PHD22 | 61 | 70 |
| PHD24 | 61 | 74 |
| PHD25 | 61 | 76 |

| Antibody | VL (SEQ ID NO) | VH (SEQ ID NO) |
|---|---|---|
| PHD26 | 78 | 70 |
| PHD28 | 78 | 74 |
| PHD29 | 78 | 76 |
| PHD30 | 85 | 84 |

The CDRs in the VH of PHD22 is as shown below:

| CDR Classification | CDR | Sequence | SEQ ID NO |
|---|---|---|---|
| Kabat | HCDR1 | EYWMH | 62 |
| | HCDR2 | TIYPGNSDTSYAQKFQG | 65 |
| | HCDR3 | FYFEDWYFDV | 68 |
| Enhanced Chothia | HCDR1 | GYTFTEYWMH | 63 |
| | HCDR2 | TIYPGNSDTS | 66 |
| | HCDR3 | FYFEDWYFDV | 68 |
| IMGT | HCDR1 | GYTFTEYW | 64 |
| | HCDR2 | IYPGNSDT | 67 |
| | HCDR3 | TRFYFEDWYFDV | 69 |

The CDRs in the VH of PHD24 is as shown below:

| CDR Classification | CDR | Sequence | SEQ ID NO |
|---|---|---|---|
| Kabat | HCDR1 | TYWMH | 20 |
| | HCDR2 | TIYPGNSDTSLAQKFQG | 73 |
| | HCDR3 | FYFEDWYFDV | 68 |
| Enhanced Chothia | HCDR1 | GYTFTTYWMH | 71 |
| | HCDR2 | TIYPGNSDTS | 66 |
| | HCDR3 | FYFEDWYFDV | 68 |
| IMGT | HCDR1 | GYTFTTYW | 72 |
| | HCDR2 | IYPGNSDT | 67 |
| | HCDR3 | TRFYFEDWYFDV | 69 |

The CDRs in the VH of PHD25 is as shown below:

| CDR Classification | CDR | Sequence | SEQ ID NO |
|---|---|---|---|
| Kabat | HCDR1 | TYWMH | 20 |
| | HCDR2 | TIYPGNSDTSFAQKFQG | 75 |
| | HCDR3 | FYFEDWYFDV | 68 |
| Enhanced Chothia | HCDR1 | GYTFTTYWMH | 71 |
| | HCDR2 | TIYPGNSDTS | 66 |
| | HCDR3 | FYFEDWYFDV | 68 |
| IMGT | HCDR1 | GYTFTTYW | 72 |
| | HCDR2 | IYPGNSDT | 67 |
| | HCDR3 | TRFYFEDWYFDV | 69 |

The CDRs in the VH of PHD30 is as shown below:

| CDR Classification | CDR | Sequence | SEQ ID NO |
|---|---|---|---|
| Kabat | HCDR1 | EYWMH | 62 |
| | HCDR2 | TIYPGNSDSSFAQKFQG | 79 |
| | HCDR3 | FYYEDWYFDV | 26 |
| Enhanced Chothia | HCDR1 | GYTFTEYWMH | 63 |
| | HCDR2 | TIYPGNSDSS | 79 |
| | HCDR3 | FYYEDWYFDV | 26 |
| IMGT | HCDR1 | GYTFTEYW | 64 |
| | HCDR2 | IYPGNSDS | 25 |
| | HCDR3 | TRFYYEDWYFDV | 27 |

The CDRs in the VL of PHD25 is as shown below:

| CDR Classification | CDR | Sequence | SEQ ID NO |
|---|---|---|---|
| Kabat | LCDR1 | RASSSISWLY | 56 |
| | LCDR2 | YTSTLGS | 58 |
| | LCDR3 | QQWHSYPPT | 60 |
| Enhanced Chothia | LCDR1 | RASSSISWLY | 56 |
| | LCDR2 | YTSTLGS | 58 |
| | LCDR3 | QQWHSYPPT | 60 |
| IMGT | LCDR1 | SSISW | 57 |
| | LCDR2 | YT | 59 |
| | LCDR3 | QQWHSYPPT | 60 |

The CDRs in the VL of PHD26 is as shown below:

| CDR Classification | CDR | Sequence | SEQ ID NO |
|---|---|---|---|
| Kabat | LCDR1 | RASSSISWLY | 56 |
| | LCDR2 | YTSSLGS | 77 |
| | LCDR3 | QQWHSYPPT | 60 |
| Enhanced Chothia | LCDR1 | RASSSISWLY | 56 |
| | LCDR2 | YTSSLGS | 77 |
| | LCDR3 | QQWHSYPPT | 60 |
| IMGT | LCDR1 | SSISW | 57 |
| | LCDR2 | YT | 59 |
| | LCDR3 | QQWHSYPPT | 60 |

The CDRs in the VL of PHD30 is as shown below:

| CDR Classification | CDR | Sequence | SEQ ID NO |
|---|---|---|---|
| Kabat | LCDR1 | RASSSISYLY | 80 |
| | LCDR2 | RTSSLGS | 82 |
| | LCDR3 | QQYHSYPPT | 32 |
| Enhanced Chothia | LCDR1 | RASSSISYLY | 80 |
| | LCDR2 | RTSSLGS | 82 |
| | LCDR3 | QQYHSYPPT | 32 |
| IMGT | LCDR1 | SSISY | 81 |
| | LCDR2 | RT | 83 |
| | LCDR3 | QQYHSYPPT | 32 |

The affinity data are shown in the following table:

| Antibody | $K_D$ (M) | $K_{on}$ (1/Ms) | $K_{off}$ (1/s) |
|---|---|---|---|
| PHD22 | 2.38E−08 | 4.73E+05 | 1.13E−02 |
| PHD24 | 1.16E−08 | 4.46E+05 | 5.18E−03 |
| PHD25 | 1.23E−08 | 3.83E+05 | 4.71E−03 |
| PHD26 | 1.66E−08 | 4.90E+05 | 8.11E−03 |
| PHD28 | 1.84E−08 | 4.15E+05 | 7.64E−03 |

-continued

| Antibody | $K_D$ (M) | $K_{on}$ (1/Ms) | $K_{off}$ (1/s) |
|---|---|---|---|
| PHD29 | 1.19E−08 | 3.71E+05 | 4.41E−03 |
| PHD30 | 7.23E−09 | 4.86E+05 | 3.51E−03 |

Figure 9:
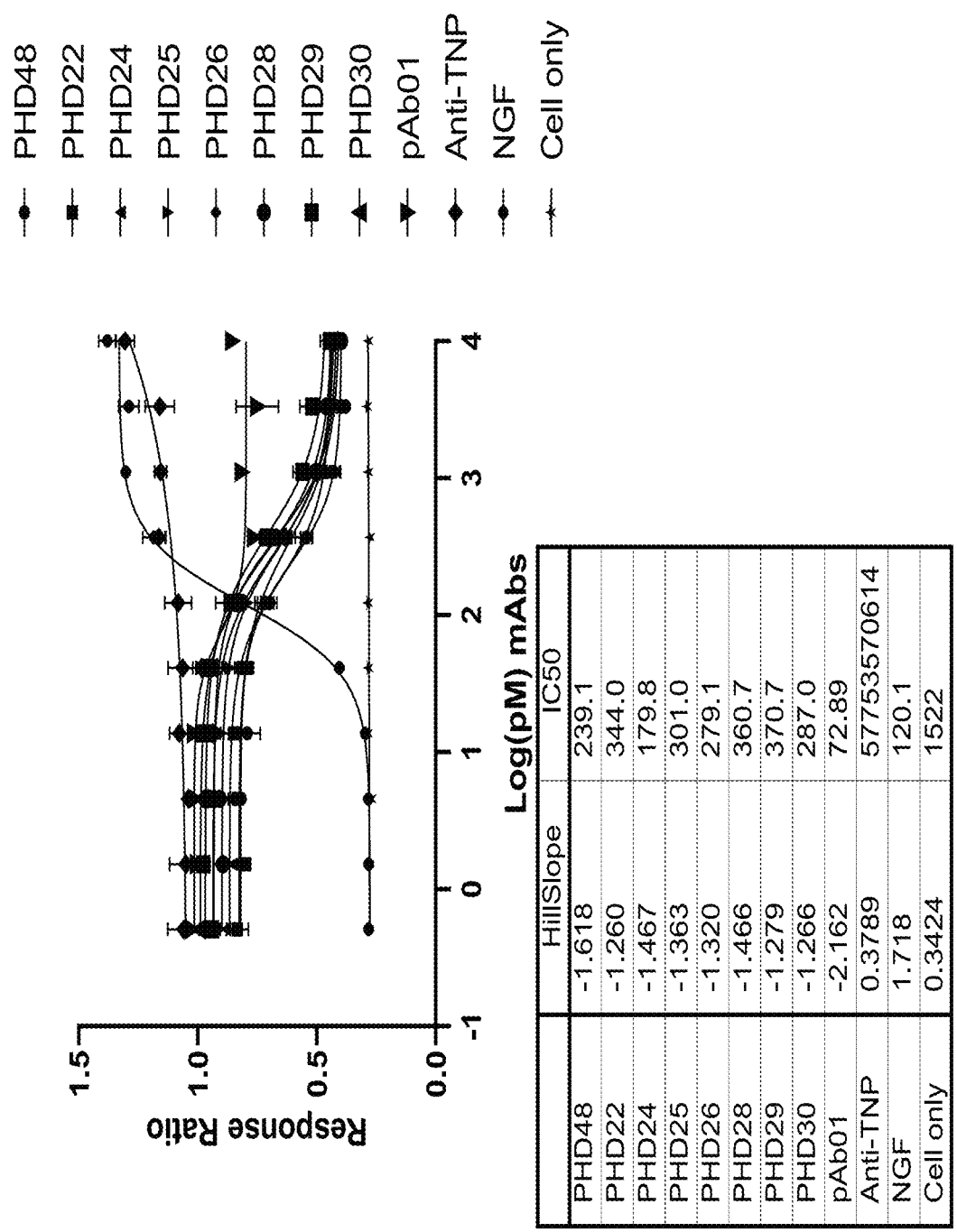
FIG. 9 illustrates the results of NFAT functional analysis of exemplary antibodies of the present disclosure.

In addition, as shown in the antagonist NFAT assay (FIG. 9), the TrkA antibodies PHD22, PHD24, PHD25, PHD26, PHD28, PHD29, PHD30 and PHD48 could inhibit the activation of the TrkA signaling induced by human NGF. and their inhibition activity is significantly better than the control antibody pAb01.

Example 10. The TrkA Antibodies Competition Assay

Figure 7B:
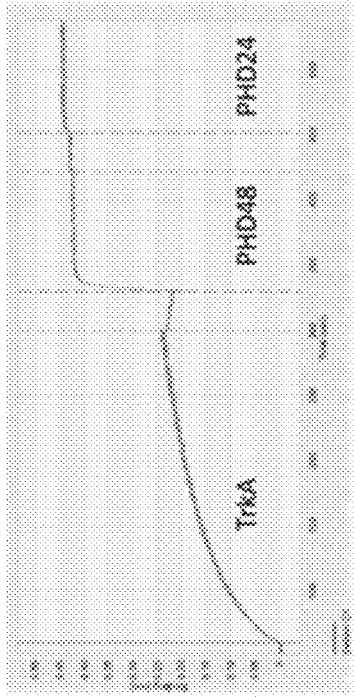
FIG. 7A-7O illustrate the sensorgram of TrkA antibodies competition assay.
Figure 7D:
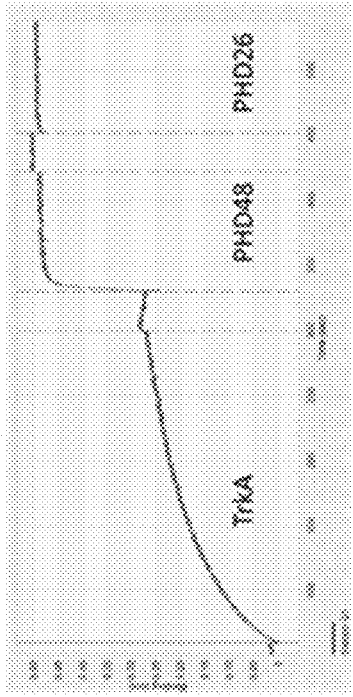
Figure 7A:
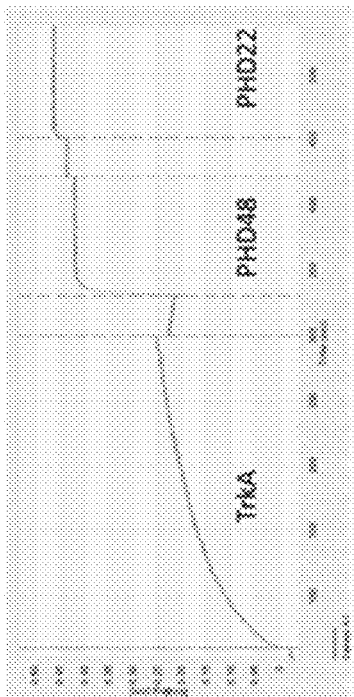
Figure 7C:
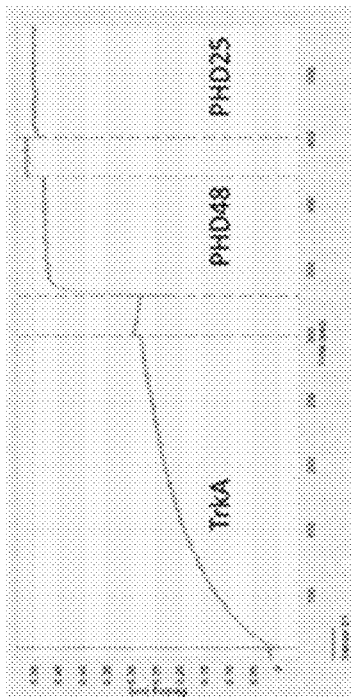
Figure 7J:
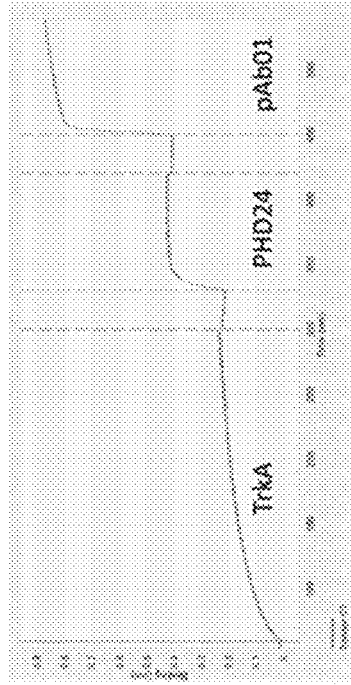
Figure 7L:
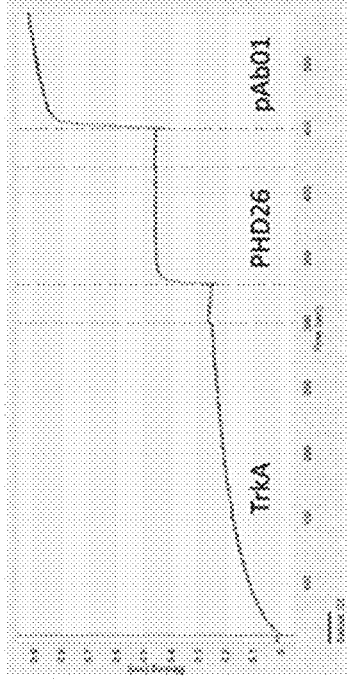
Figure 7I:
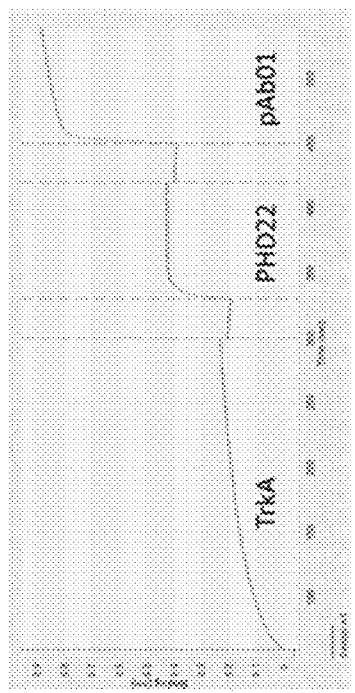
Figure 7K:
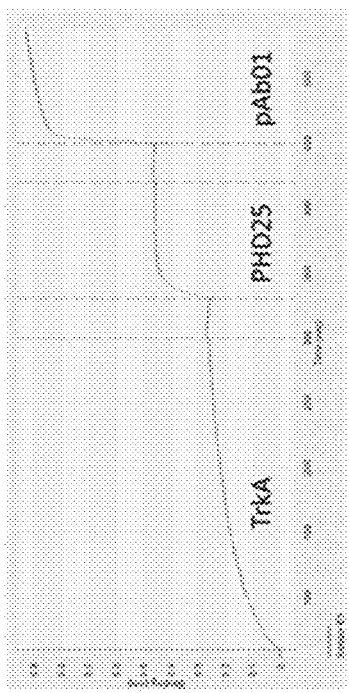
Figure 7N:
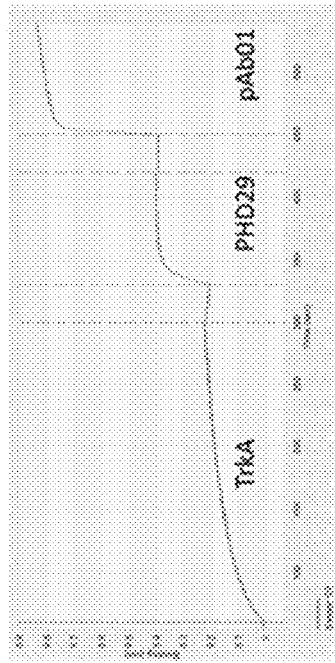
Figure 7M:
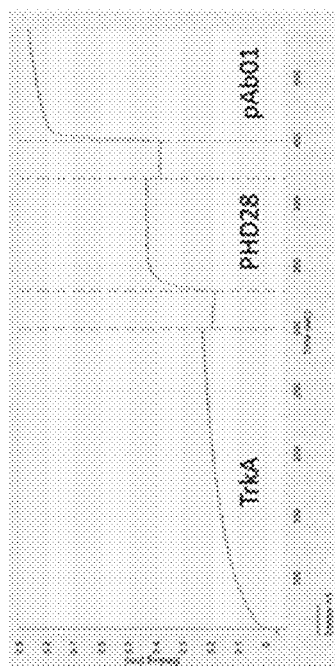
Figure 7O:
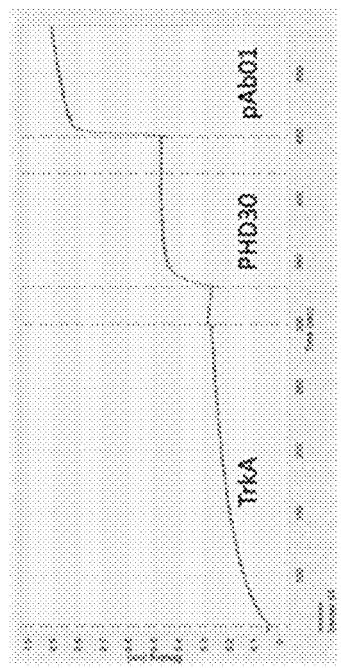

To determine whether TrkA antibodies compete each other for binding to their target. A bio-layer interferometry (BLI) method-based competition assay was performed on Octet Red384. Briefly, Anti-Penta-HIS (HIS1K) Biosensor (Fortebio) was put in PBS with 0.1% w/v bovine serum albumin and 0.05% Tween-20 (assay buffer) for a minimum of 10 min in the pre-wetting plate. The TrKA ECD protein at 100 nM in assay buffer was captured on the sensor to obtain a capture level of 0.3~1 nm. The loaded biosensors were then equilibrated with an assay buffer for a minimum of 30s followed by binding of the first antibody for 90s. After the second equilibration, the second antibody was loaded for 90s. Antibodies PHD22 (FIG. 7A), PHD24 (FIG. 7B), PHD25 (FIG. 7C), PHD26 (FIG. 7D), PHD28 (FIG. 7E), PHD29 (FIG. 7F), PHD30 (FIG. 7G), and PHD48 (FIG. 7A-7G) compete with each other for binding to TrkA. The control antibody pAb01 (FIG. 7H-7O) (with a VH as set forth in SEQ ID NO: 123, and a VL as set forth in SEQ ID NO: 124) does not compete with PHD22 (FIG. 7I), PHD24 (FIG. 7J), PHD25 (FIG. 7K), PHD26 (FIG. 7L), PHD28 (FIG. 7M), PHD29 (FIG. 7N), PHD30 (FIG. 7O) or PHD48 (FIG. 7H).

Example 11. The NGF Blocking Assay

Figure 8A:
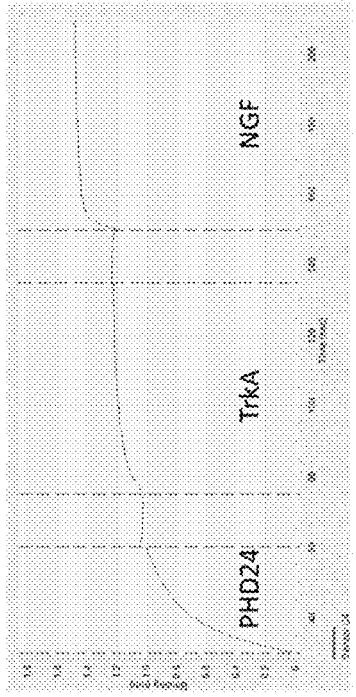
Figure 8B:
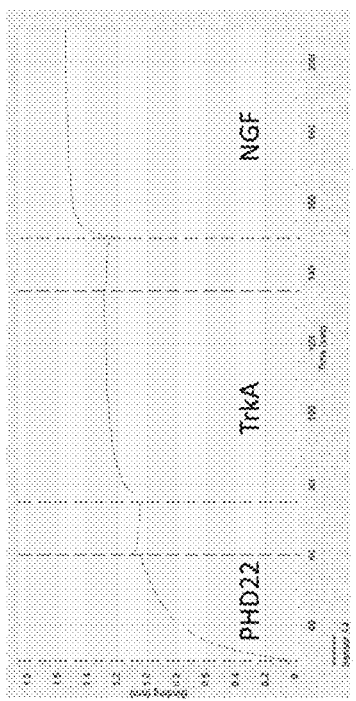
Figure 8C:
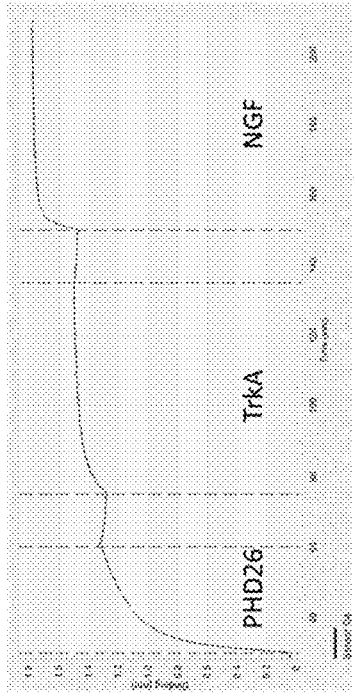
Figure 8D:
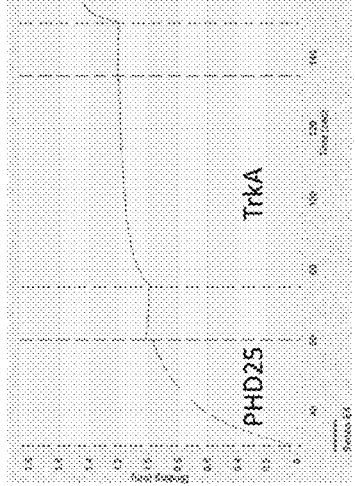
Figure 8J:
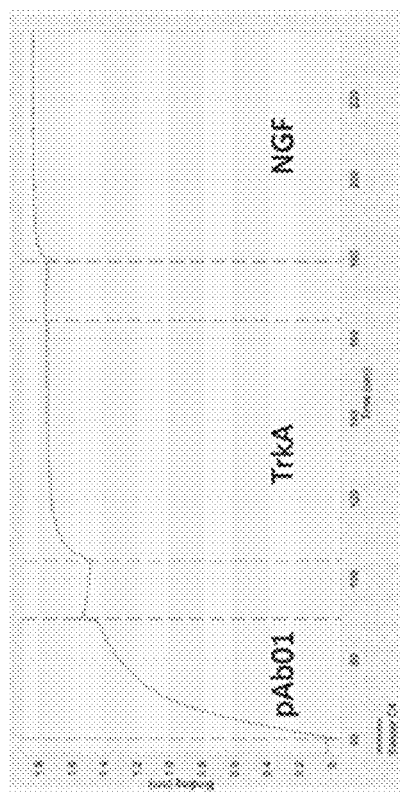
Figure 8I:
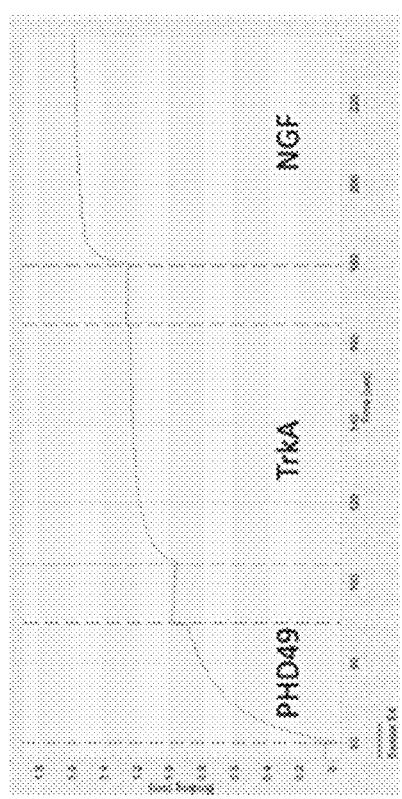

To determine whether TrkA antibodies can block the binding between TrkA and NGF. A bio-layer interferometry (BLI) method-based competition assay was performed on Octet Red384. Briefly, anti-human Fc(AHC) Biosensor (Fortebio) were put in PBS with 0.1% w/v bovine serum albumin and 0.05% Tween-20 (assay buffer) for a minimum of 10 min in the pre-wetting plate. The antibody at 100 nM in assay buffer was captured on the sensor to obtain a capture level of 0.5~1.5 nm. The loaded biosensors were then equilibrated in an assay buffer for a minimum of 15s followed by TrkA ECD binding for a minimum of 60s. After the second equilibration, NGF was loaded for a minimum of 60s. Antibody PHD22 (FIG. 8A), PHD24 (FIG. 8B), PHD25 (FIG. 8C), PHD26 (FIG. 8D), PHD28 (FIG. 8E), PHD29 (FIG. 8F), PHD30 (FIG. 8G), PHD48 (FIG. 8H), and PHD49 (FIG. 8I) do not block the binding between TrkA and NGF (FIG. 8A-8I). In contrast, the control antibody pAb01 blocks the binding between TrkA and NGF (FIG. 8J).

Figure 10:
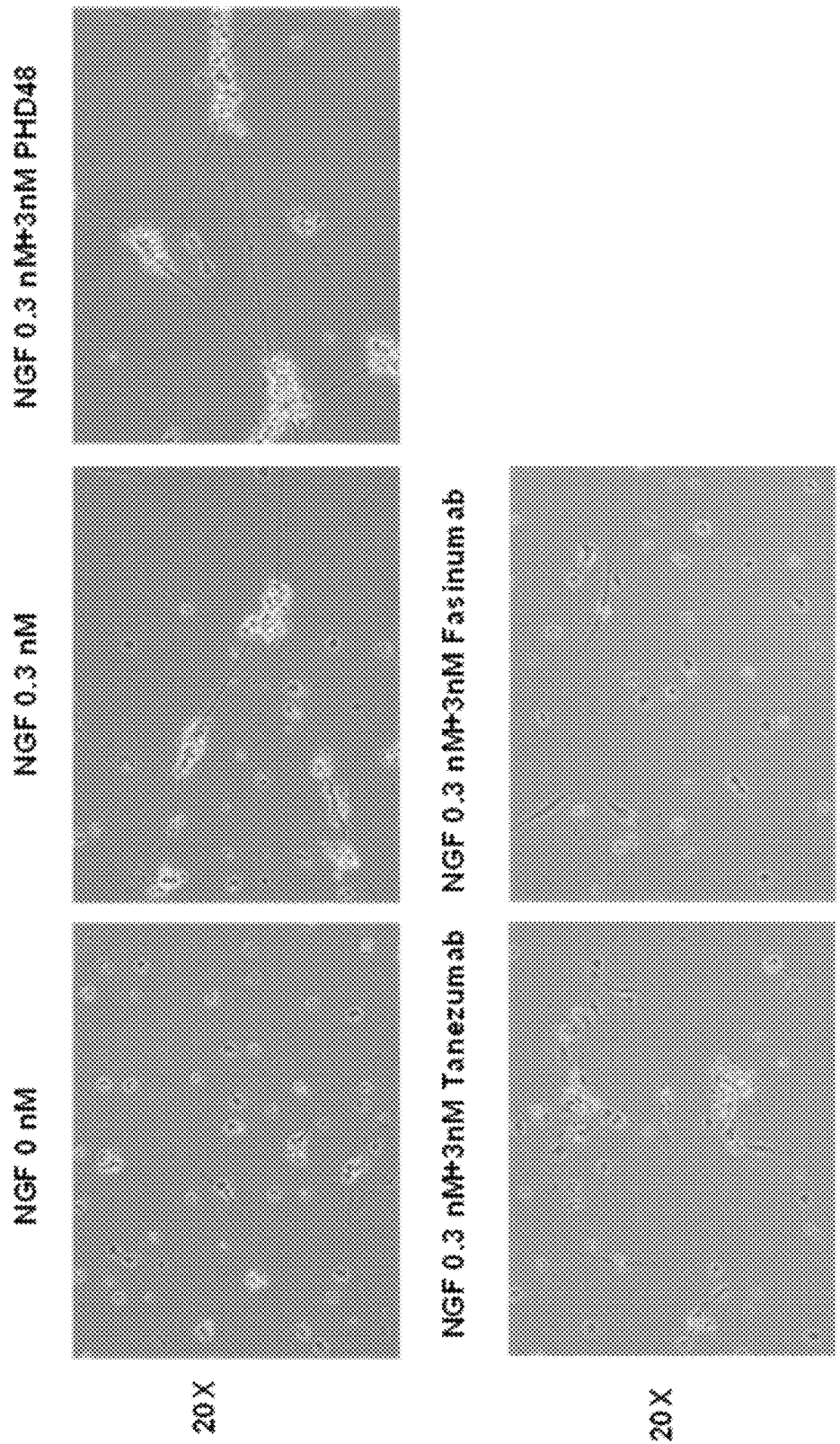
FIG. 10 shows Brightfield photography after 72 hours of DRG seeding.

Example 12. The Effects of the TrkA Antibody on DRG Neurons Survival and Axon Extension DRG dissociated primary neurons were prepared from humanized embryonic mice. DRG were collected, incubated for 5-8 mins at 37° C. with 0.05% Trypsin-EDTA, pipetted into single cells, and then plated onto petri dish pretreated with poly-D-lysine and laminin, at a density of 5000 cells/well on a 24 well-plate with different DRG conditioned medium (NGF 0 nM; NGF 0.3 nM; NGF 0.3 nM/PHD48 3 nM; NGF 0.3 nM/Tanezumab 3 nM; NGF 0.3 nM/Fasinumab 3 nM). A half change of DRG conditioned medium was performed after 48 h, while 5-fluoro-2'-deoxyuridine at a final concentration of 5 ug/ml was added to inhibit the excessive proliferation of glial cells. After 72 h of DRG seeding, 10× and 20× brightfield photography were performed. As shown in FIG. 10, brightfield photography showed normal survival and axon extension of DRG neurons in NGF 0.3 nM group and NGF 0.3 nM/PHD48 3 nM group. Only a small number of DRG neurons survived and the axons of surviving neurons were extremely short in the NGF 0 nM group, NGF 0.3 nM/Tanezumab 3 nM group, and NGF 0.3 nM/3 nM Fasinumab group.

Figure 11:
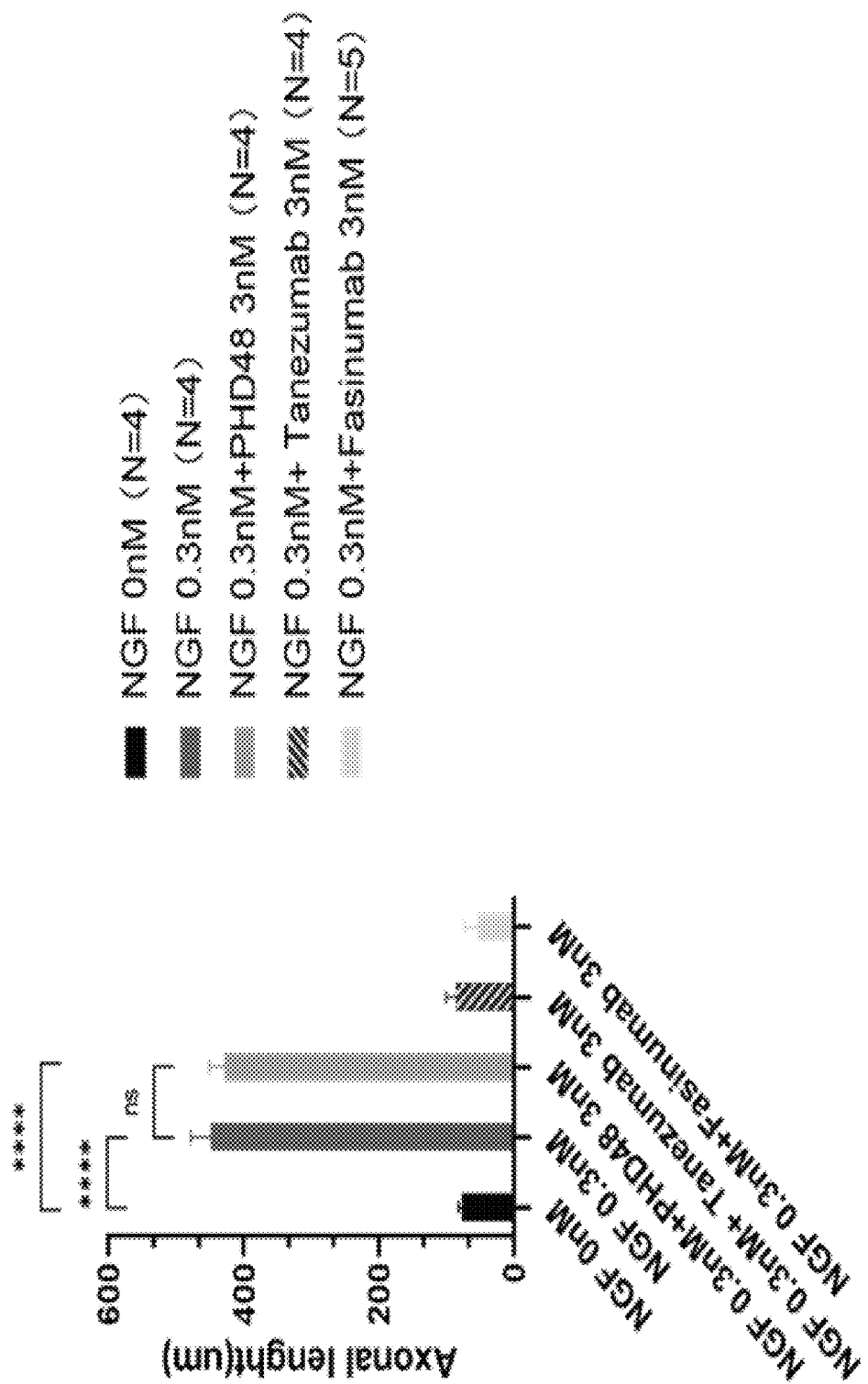
FIG. 11 shows Brightfield axon length statistics after 72 hours of DRG seeding.

After 72 hours of DRG seeding, the intermediate visual field of each well of the experimental group was taken (20×), the axon path of DRG neurons was traced and the length was calculated by ImageJ, and the average length of each field of view was used for the above statistics. The graph was generated using GraphPad Software, and the data reported as the mean±standard error of the mean (SEM). One-way ANOVA was used to analyze the data. **** P<0.0001. As shown in FIG. 11, the average axon length of NGF 0.3 nM group and NGF 0.3 nM/PHD48 3 nM group exceeded 400 m, and there was no significant difference in axon length between the two groups. The average axon length in NGF 0 nM group, NGF 0.3 nM/3 nM Tanezumab group and NGF 0.3 nM/3 nM Fasinumab group were all less than 100 m, and the axon length of DRG neurons in the NGF 0.3 nM/3 nM Fasinumab group were significantly shorter. These results indicate that PHD48, unlike NGF neutralizing antibodies (Tanezumab and Fasinumab), had no significant inhibitory effect on NGF-mediated survival and axon extension of the DRG neurons.

Example 13. The TrkA Antibody Reduces NGF-Induced Pain in Mice

Inflammation and neuron damage result in an early and sustained elevation of NGF levels in vivo. In adult, NGF may increase sensitivity to noxious stimuli, that is to produce hyperalgesia. Injection of exogenous NGF produces mechanical and thermal hypersensitivity changes in rodents and humans. Intraplantar injections of NGF result in a relatively brief increase in mechanical hypersensitivity.

Figure 12:
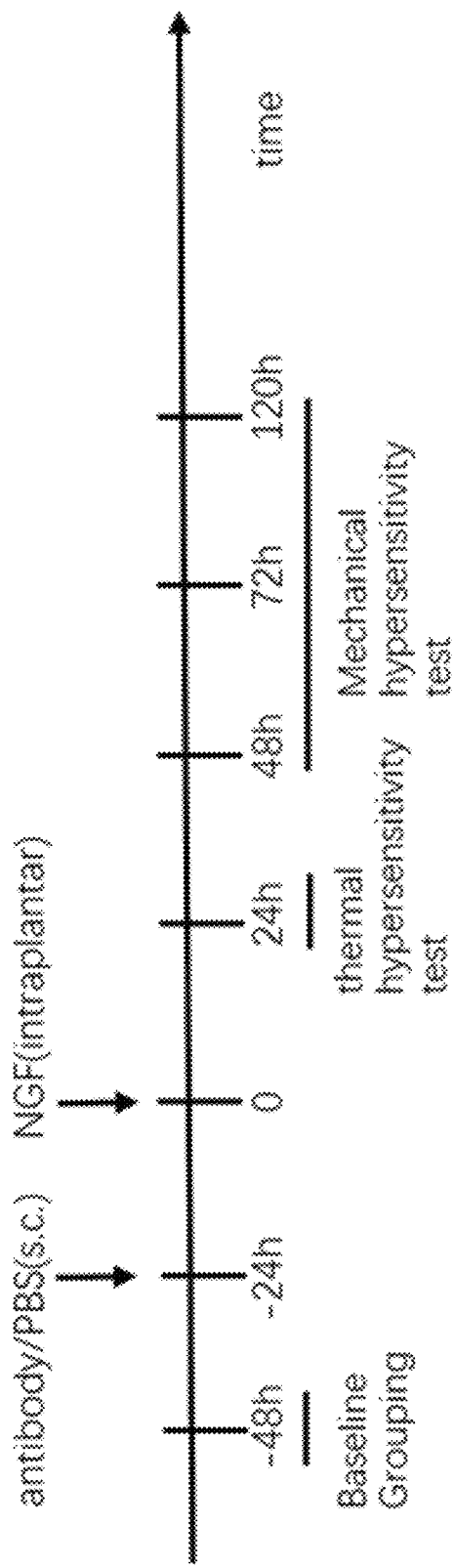
FIG. 12 illustrates the scheme of intraplantar injection of NGF induced hypersensitivity model.
Figure 13A:
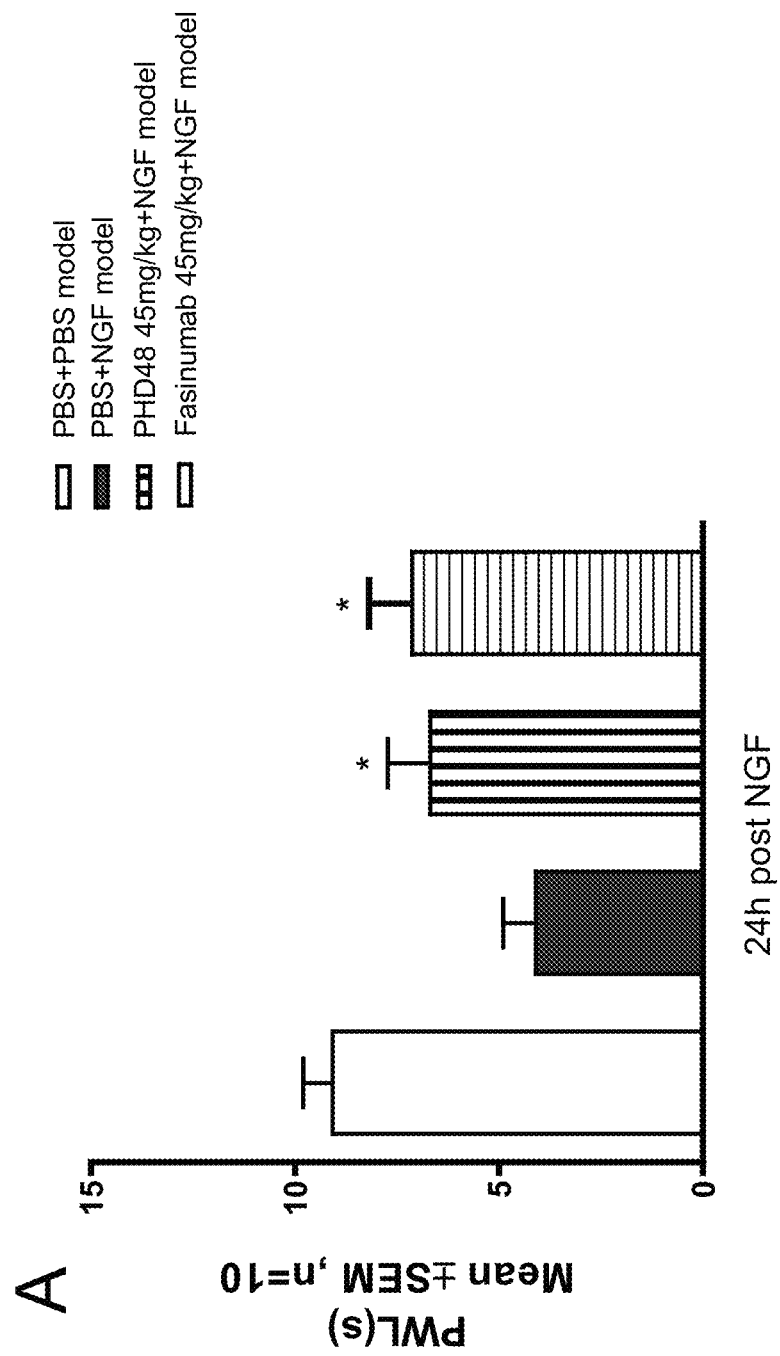
FIG. 13A-13B illustrate pharmacological evaluation of NGF induced mechanical and thermal sensitivity with exemplary antibodies of the present disclosure.
Figure 13B:
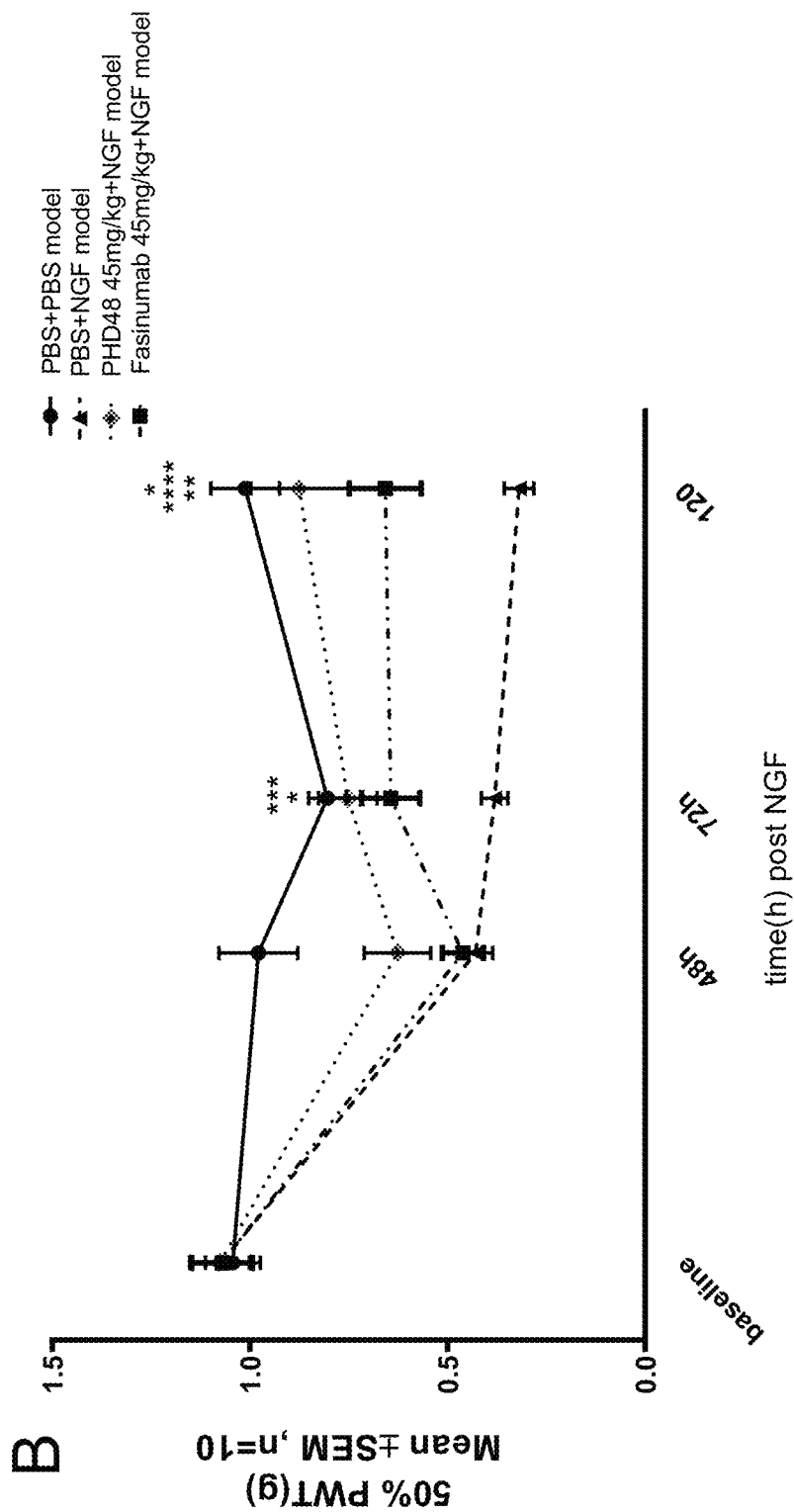

To understand the pain relief effects of the TrkA antibody of the present disclosure (such as PHD48), NGF induced hypersensitivity model (by intraplantar injection of NGF) was used as a model (FIG. 12). The results demonstrate that subcutaneous injection of Fasinumab significantly alleviated thermal hypersensitivity (24h after NGF injection, FIG. 13A) and mechanical hypersensitivity (72h-120h after NGF injection, FIG. 13B), which indicate that the hypersensitivities are mediated by NGF signal pathway. In this model, PHD48 also significantly alleviated thermal hypersensitivity (24h after NGF induction, FIG. 13A) and alleviated mechanical hypersensitivity (48h-120h after NGF injection, FIG. 13B) by inhibiting the NGF/TrkA signaling.

Example 14. The TrkA Antibody Reduces Formalin-Induced Pain in Mice

Nerve growth factor (NGF) exerts strong pro-nociceptive effects in the peripheral nerve system mainly through its receptor TrkA.

The formalin test in mice is a reliable model of nociception and is sensitive for various classes of analgesic drugs. The noxious stimulus is an injection of dilute formalin under the skin of the dorsal surface of the right hind paw. The nociceptive behavior was recorded as motion counts (paw licking activities) from 0~45 min after the injection of formalin. And the total motion counts of the late phase (20-30 min after the injection of formalin), which represents the inflammatory pain, were calculated and analyzed among different groups.

Figure 14:
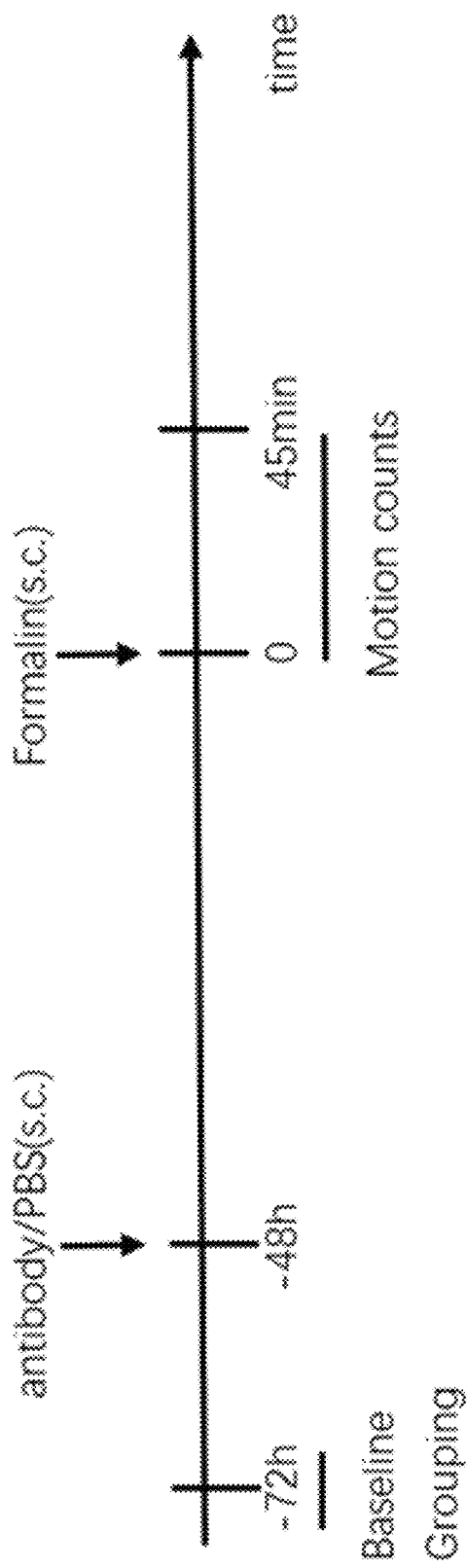
FIG. 14 illustrates the scheme of formalin-induced pain test.
Figure 15A:
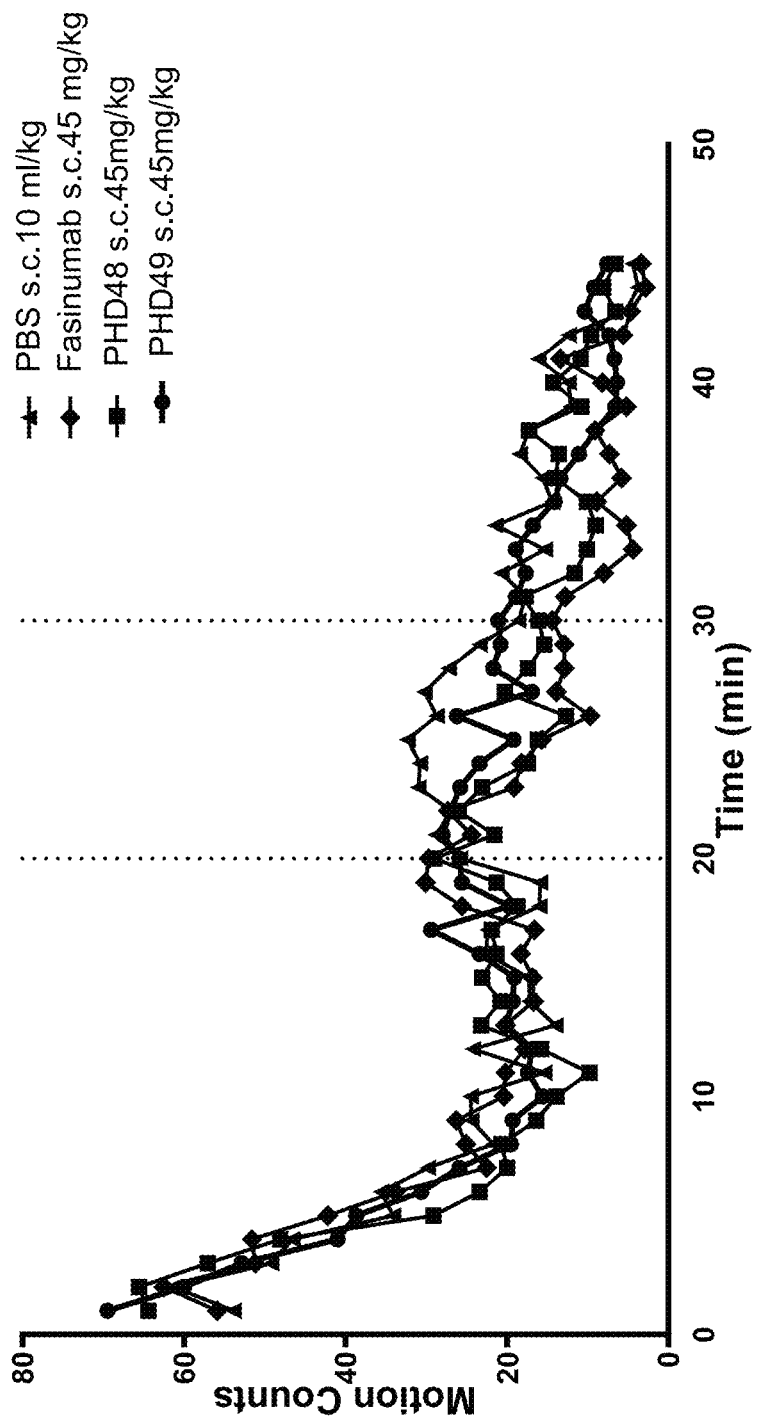
FIG. 15A-15B illustrate the antinociceptive effects of exemplary antibodies of the present disclosure in the formalin-induced pain test.
Figure 15B:
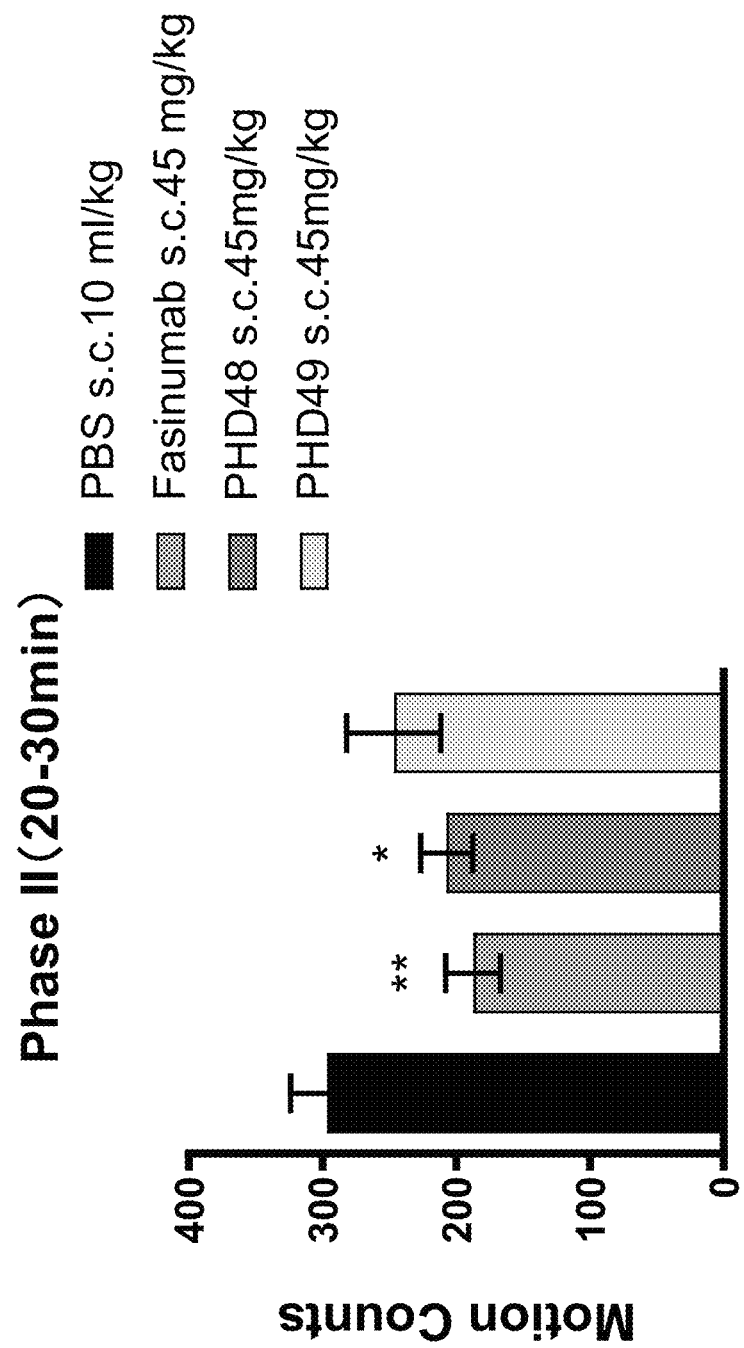

To understand the pain relief effects of the TrkA antibody of the present disclosure (e.g., PHD48), a formalin-induced inflammatory pain mouse model was established (FIG. 14) and it was found that subcutaneous injection of Fasinumab significantly alleviated increase of formalin-mediated motion counts (FIGS. 15A and 15B), which indicates formalin induced pain is mediated by NGF signal pathway. Meanwhile, PHD48 also significantly alleviated increase of formalin-mediated motion counts (FIGS. 15A and 15B), which indicates that the TrkA antibodies of the present disclosure are effective in this pain model.

Example 15. The TrkA Antibody Improved MIA-Induced OA Pain in Mice

Monoiodoacetate (MIA) injection in the knee joint leads to the progressive disruption of cartilage, which, in turn, is associated with the development of pain-like behavior. The pathological changes induced by MIA share many common traits with those observed in human OA, including loss of cartilage and alterations in the subchondral bone.

Figure 16:
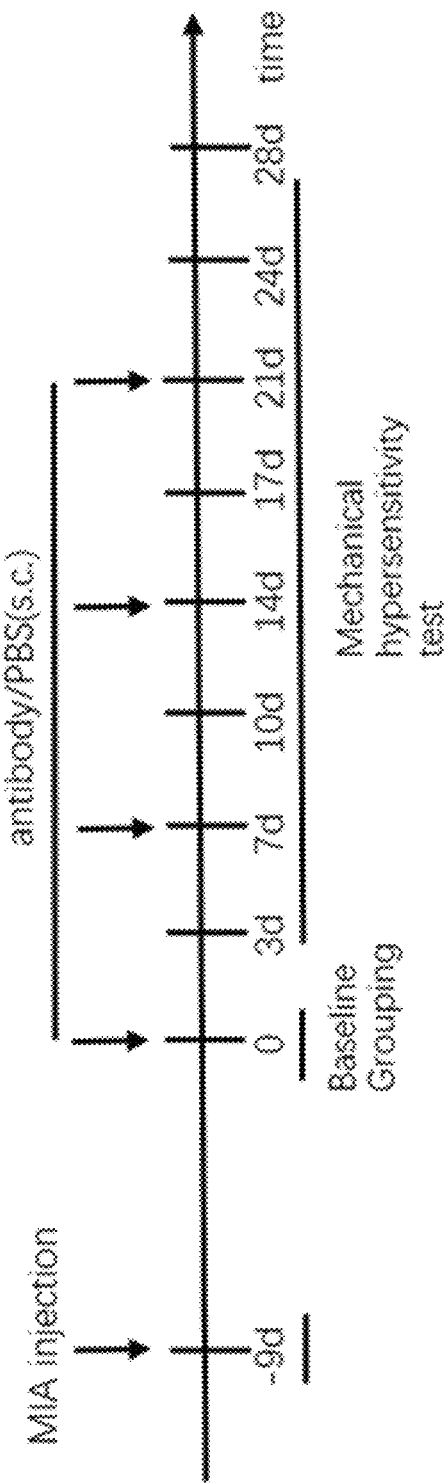
FIG. 16 illustrates the scheme of osteoarthritis (OA) pain induced by MIA injection and mechanical hypersensitivity test.
Figure 17A:
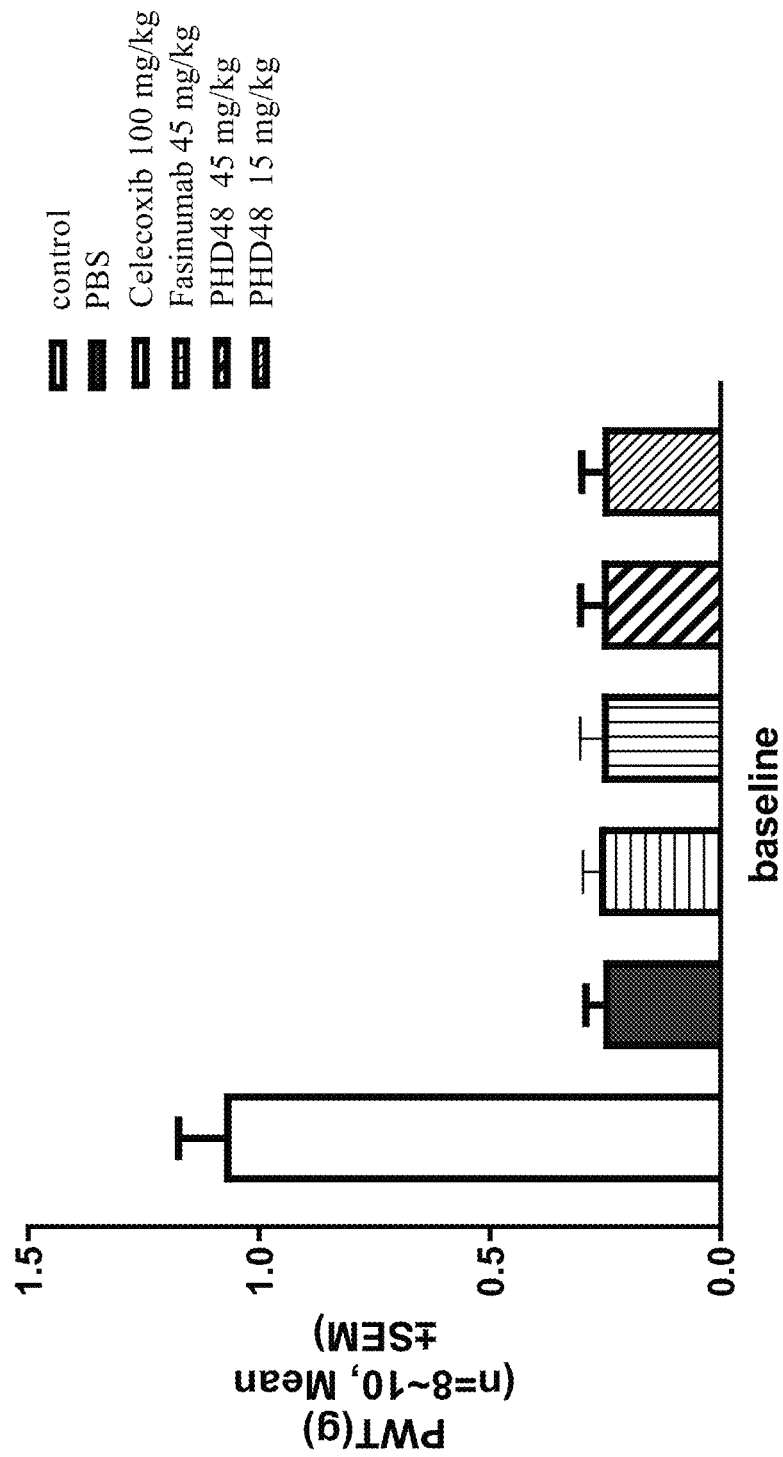
FIG. 17A-17G illustrate the effect of exemplary antibodies of the present disclosure on OA pain induced by MIA injection.
Figure 17B:
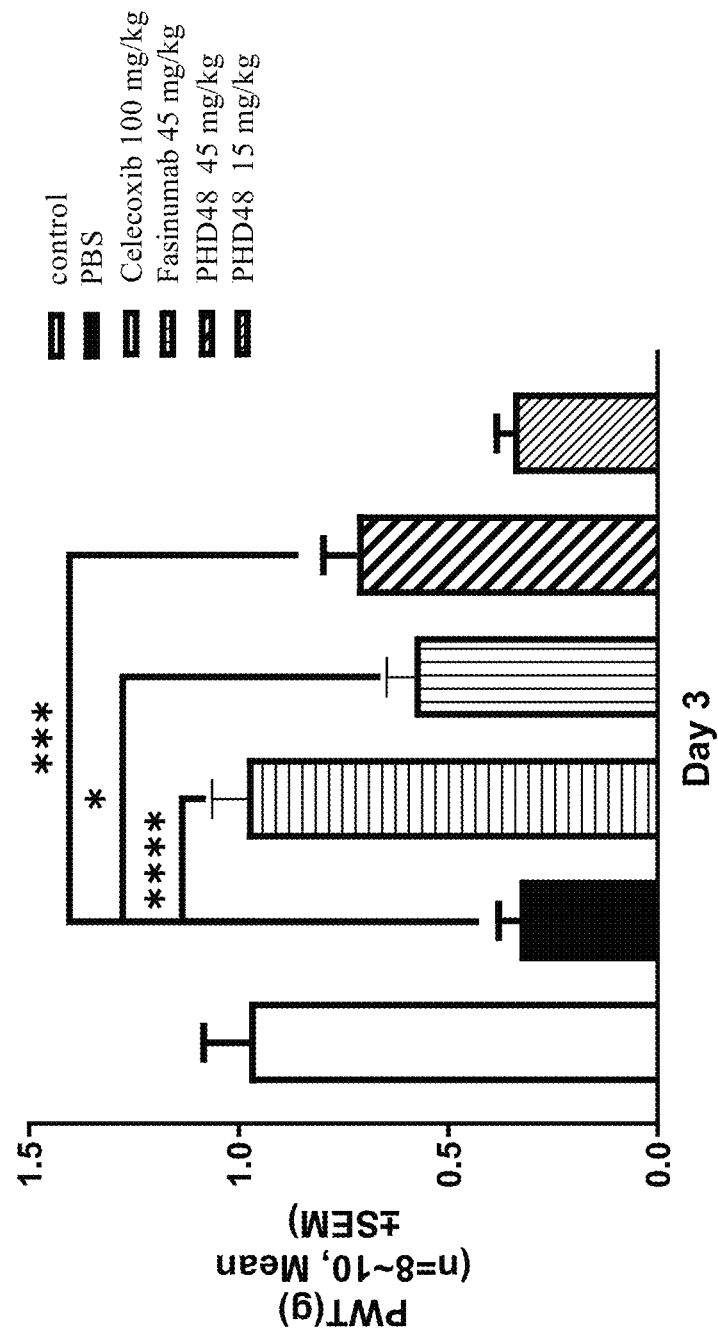
Figure 17C:
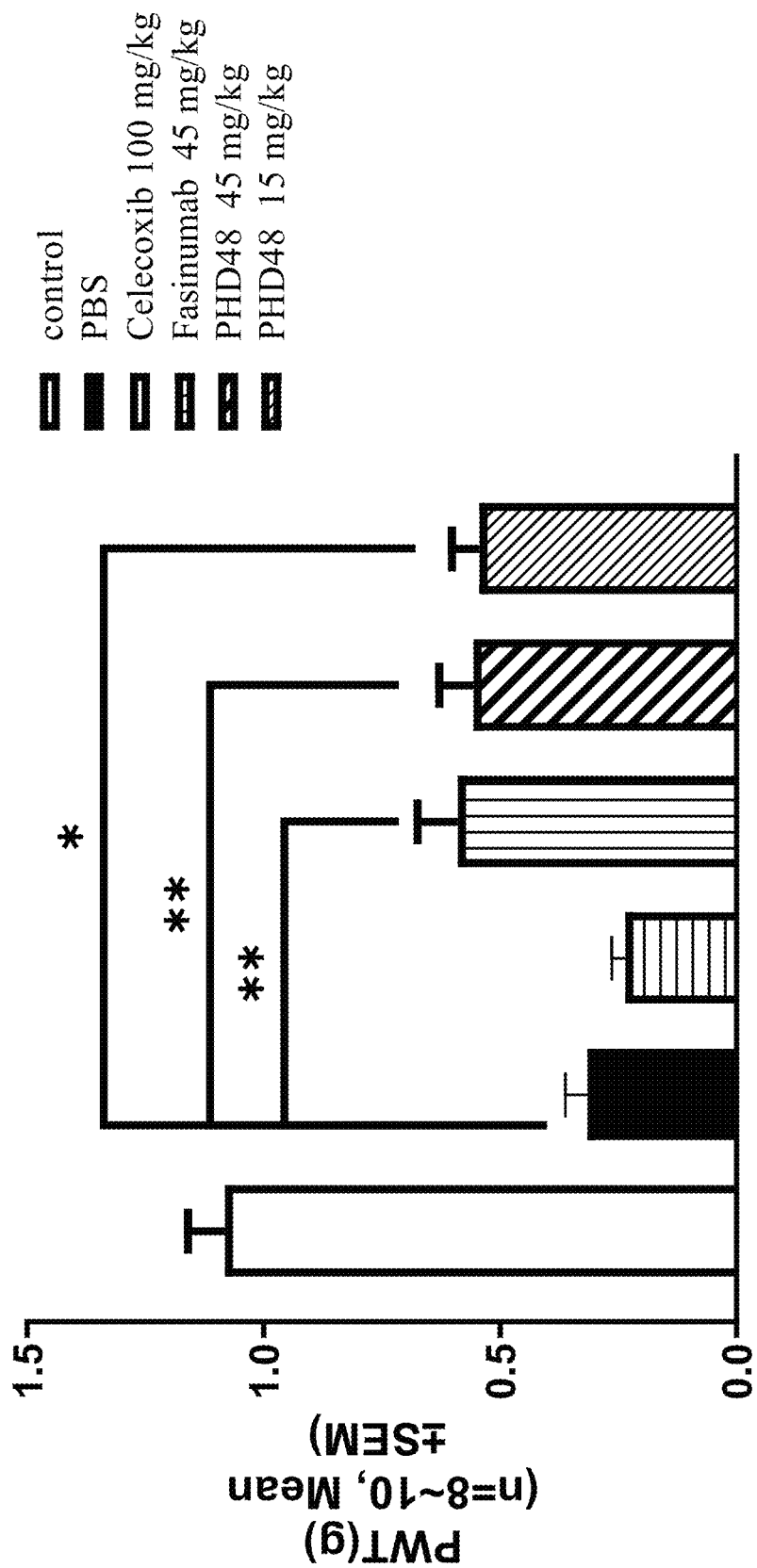
Figure 17D:
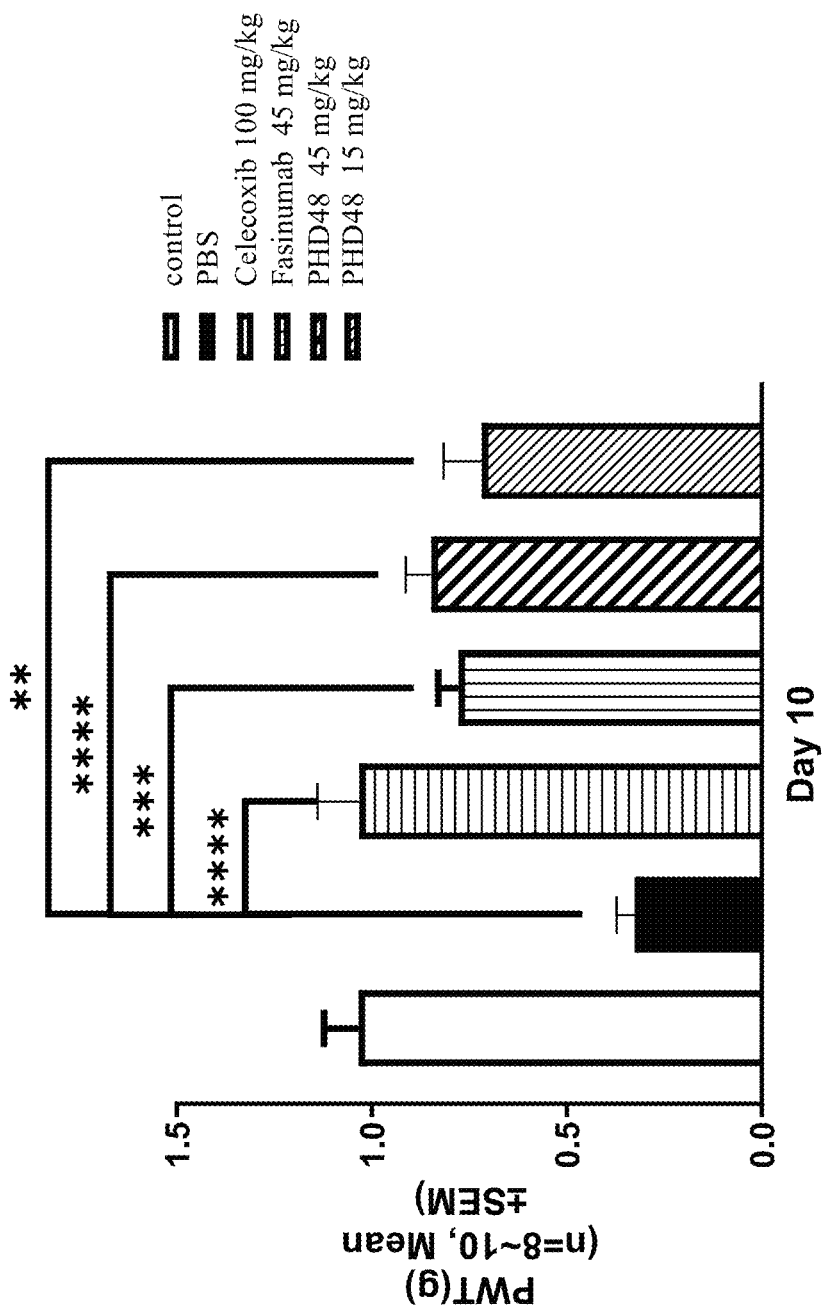
Figure 17E:
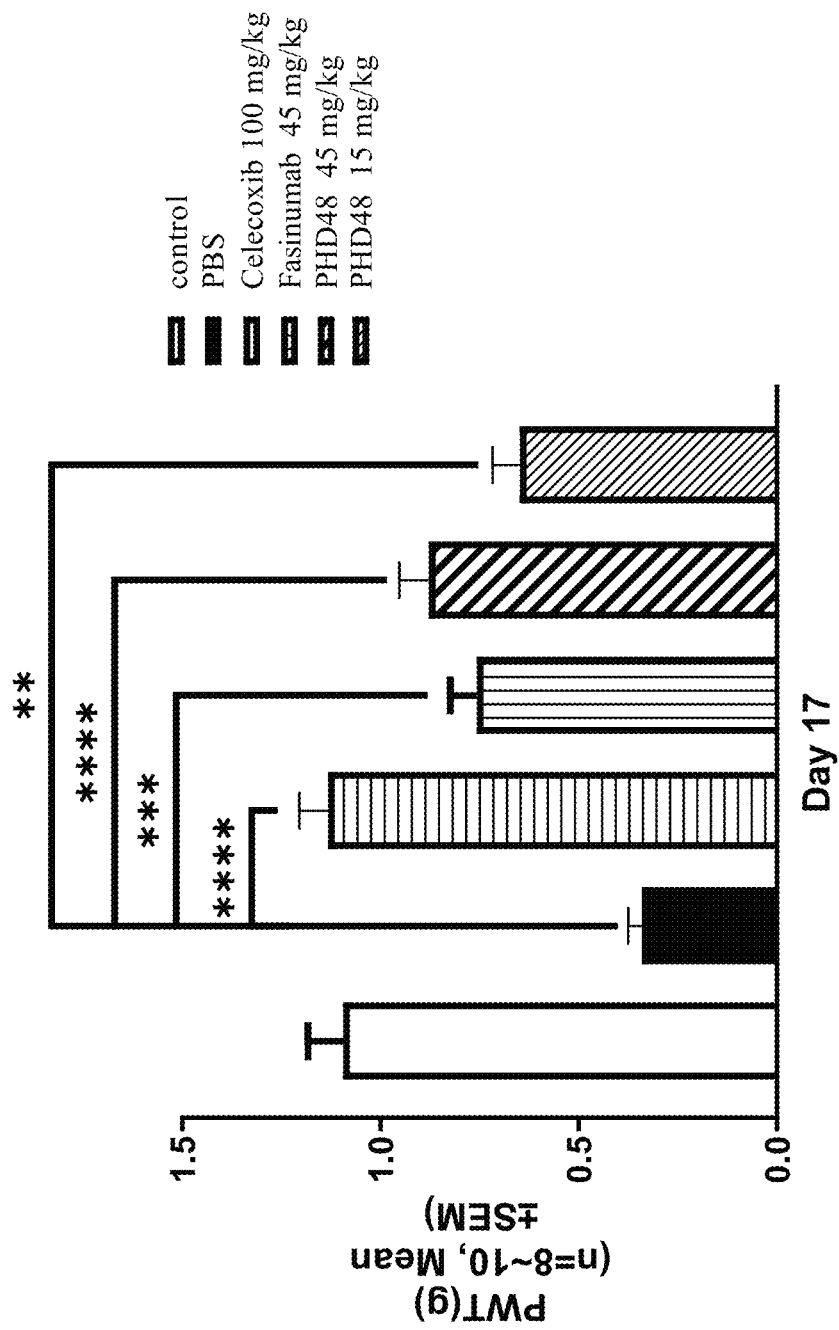
Figure 17F:
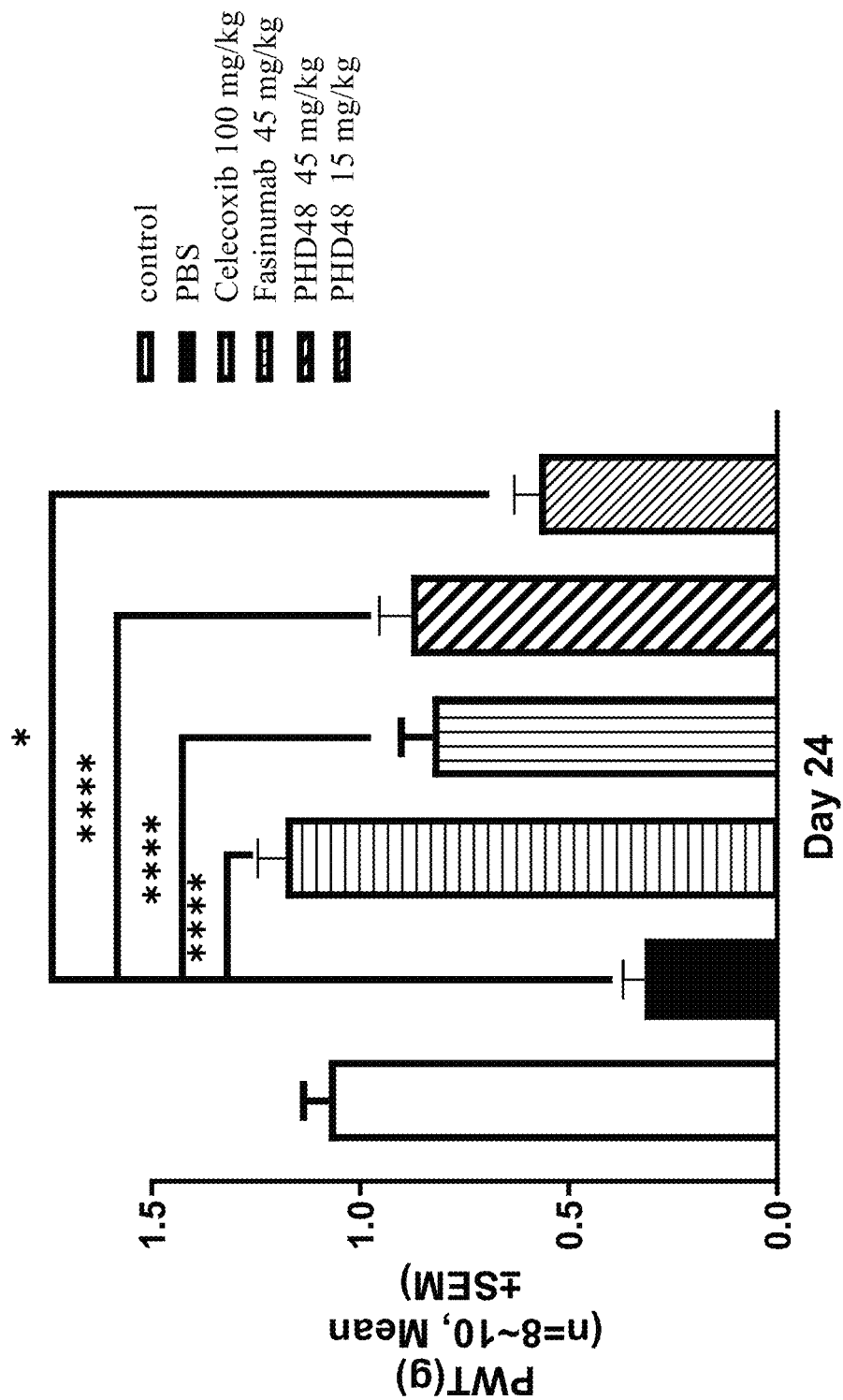
Figure 17G:
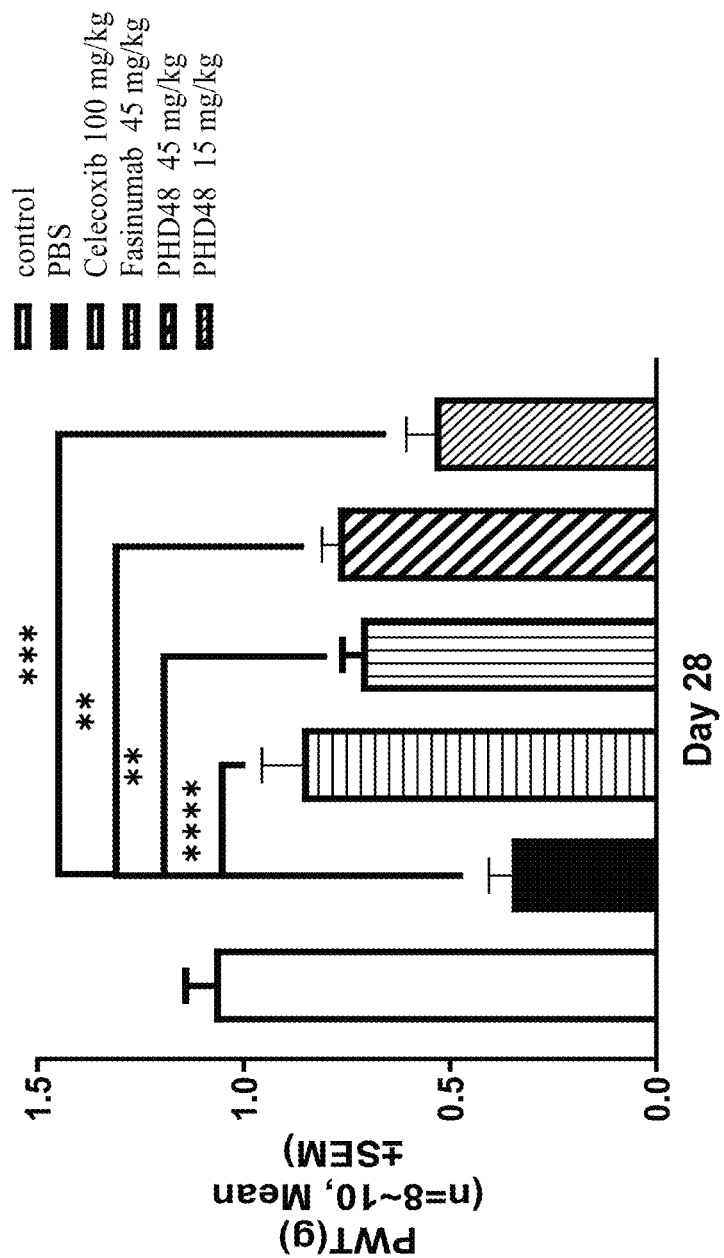

To study the effect of the TrkA antibody of the present disclosure (e.g. PHD48) on OA pain, MIA was injected in the knee joint of mouse to induce the OA pain model (FIG. 16). Except for the control group, animals in the other groups were injected with MIA in the knee joints, and a baseline screen was conducted 9 days after the MIA injection. Mice with successful model criteria (paw withdrawal threshold <0.6 g) were selected in each group, and then the testing drugs were administrated. Celecoxib (TCI, Lot. No., CJDBF-RG) 100 mg/kg, p.o., as the positive control, significantly alleviated mechanical hypersensitivity in MIA-treated mice (FIG. 17A-17G). Subcutaneous injection of Fasinumab also significantly inhibited mechanical hypersensitivity in MIA-treated mice (FIG. 17A-17G), which indicates MIA induced pain is mediated by NGF signal pathway. Meanwhile, treatment with the TrkA antibody of the present disclosure (e.g., PHD48), significantly alleviated mechanical hypersensitivity in MIA-treated mice (FIG. 17A-17G) which means that the TrkA antibodies of the present disclosure have shown promising analgesic potential for OA pain treatment.

While preferred embodiments of the present application have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed:

1. An antibody or an antigen binding fragment thereof, which is capable of specifically binding to TrkA, the antibody or the antigen binding fragment thereof comprises a light chain CDR1, a light chain CDR2, a light chain CDR3, a heavy chain CDR1, a heavy chain CDR2 and a heavy chain CDR3, wherein:

1) the light chain CDR1-3 comprises the amino acid sequence as set forth in SEQ ID NOs: 28, 30, and 32 respectively, and the heavy chain CDR1-3 comprises the amino acid sequence as set forth in SEQ ID NOs: 20, 23, and 26 respectively, or 2) the light chain CDR1-3 comprises the amino acid sequence as set forth in SEQ ID NOs: 88, 30, and 32 respectively, and heavy chain CDR1-3 comprises the amino acid sequence as set forth in SEQ ID NOs: 20, 87, and 26 respectively.

2. The antibody or the antigen binding fragment of claim 1, wherein said antibody is selected from the group consisting of a monoclonal antibody, a chimeric antibody, a humanized antibody, a fully human antibody and a multispecific antibody.

3. The antibody or the antigen binding fragment of claim 1, wherein said antigen binding fragment is selected from the group consisting of a Fab fragment, a Fab' fragment, a F(ab)$_2$ fragment, a Fv fragment, a VHH and an ScFv.

4. The antibody or the antigen binding fragment of claim 1, which comprises a light chain variable region, and said light chain variable region comprises the amino acid sequence as set forth in SEQ ID NOs: 18, 90, or 91.

5. The antibody or the antigen binding fragment of claim 1, which comprises a light chain constant region, and said light chain constant region comprises a human Ig$_K$ constant region or a human Igλ constant region.

6. The antibody or the antigen binding fragment of claim 1, which comprises a heavy chain variable region, and said heavy chain variable region comprises the amino acid sequence as set forth in SEQ ID NOs: 16, 86, 89, or 92.

7. The antibody or the antigen binding fragment of claim 1, which comprises a heavy chain constant region, and said heavy chain constant region comprises a human IgG constant region.

8. The antibody or the antigen binding fragment of claim 1, comprising:
   1) a light chain variable region comprising the amino acid sequence as set forth in SEQ ID NO: 18, and a heavy chain variable region comprising the amino acid sequence as set forth in SEQ ID NO: 16;
   2) a light chain variable region comprising the amino acid sequence as set forth in SEQ ID NO: 90, and a heavy chain variable region comprising the amino acid sequence as set forth in SEQ ID NO: 89;
   3) a light chain variable region comprising the amino acid sequence as set forth in SEQ ID NO: 91, and a heavy chain variable region comprising the amino acid sequence as set forth in SEQ ID NO: 86; or
   4) a light chain variable region comprising the amino acid sequence as set forth in SEQ ID NO: 91, and a heavy chain variable region comprising the amino acid sequence as set forth in SEQ ID NO: 92.

9. A fusion protein comprising the antibody or the antigen binding fragment of claim 1.

10. A protein conjugate, comprising the antibody or the antigen binding fragment of claim 1.

11. An isolated nucleic acid molecule or molecules, encoding for the antibody or the antigen binding fragment of claim 1.

12. A vector or vectors, comprising the isolated nucleic acid molecule or molecules of claim 11.

13. A cell, comprising the isolated nucleic acid molecule or molecules of claim 11.

14. A composition, comprising the antibody or the antigen binding fragment of claim 1, and optionally a pharmaceutically acceptable excipient.

* * * * *